(12) United States Patent
Nomiyama et al.

(10) Patent No.: US 8,980,272 B2
(45) Date of Patent: *Mar. 17, 2015

(54) ANTIBODY TARGETING OSTEOCLAST-ASSOCIATED PROTEIN

(75) Inventors: Hisayuki Nomiyama, Kumamoto (JP);
Toshio Kukita, Fukuoka (JP);
Yoshiharu Hiruma, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 1261 days.

This patent is subject to a terminal disclaimer.

(21) Appl. No.: 11/503,574

(22) Filed: Aug. 11, 2006

(65) Prior Publication Data

US 2007/0081974 A1 Apr. 12, 2007

Related U.S. Application Data

(63) Continuation of application No. PCT/JP2005/002373, filed on Feb. 9, 2005.

(30) Foreign Application Priority Data

Feb. 12, 2004 (JP) ................................ 2004-035216

(51) Int. Cl.
*A61K 39/395* (2006.01)
*C07K 16/18* (2006.01)
*C07K 16/28* (2006.01)
*C12Q 1/68* (2006.01)
*A61K 39/00* (2006.01)

(52) U.S. Cl.
CPC .............. *C12Q 1/6883* (2013.01); *C07K 16/28* (2013.01); *A61K 2039/505* (2013.01); *C07K 2316/96* (2013.01); *C12Q 1/6811* (2013.01); *C12Q 2600/158* (2013.01); *G01N 2800/108* (2013.01); *C07K 2317/34* (2013.01)
USPC ................... 424/141.1; 424/142.1; 424/143.1; 424/139.1; 530/388.1; 530/388.15; 530/388.22; 530/387.9

(58) Field of Classification Search
None
See application file for complete search history.

(56) References Cited

U.S. PATENT DOCUMENTS

| 5,331,573 | A | 7/1994 | Balaji et al. |
| 7,364,736 | B2 | 4/2008 | Boyle et al. |
| 7,420,000 | B2 * | 9/2008 | Petasis ........................... 514/461 |
| 7,449,185 | B2 | 11/2008 | Yamaguchi et al. |
| 2005/0089522 | A1 | 4/2005 | Anderson et al. |
| 2007/0081974 | A1 | 4/2007 | Nomiyama et al. |

FOREIGN PATENT DOCUMENTS

| JP | 06-345667 | 12/1994 |
| WO | WO 01/36463 A2 * | 5/2001 |
| WO | WO 2009/048072 | 4/2009 |

OTHER PUBLICATIONS

Wilson et al., Dev., 2006, vol. 133(24):4871-4879.*
Chiu et al., J. Bone Miner. Res., vol. 27(1):79-92.*
Chiu, et al., J. Bone Miner. Res., 2012, vol. 27(1):79-92.*
Eleveld-Trancikova et al. (2005); "The dendritic cell-derived protein DC-STAMP is highly conserved and localizes to the endoplasmic reticulum"; *Journal of Leukocyte Biology*; 77:337.
Hartgers et al. (2000); "DC-STAMP, a novel multimembrane-spanning molecule preferentially expressed by dendritic cells"; *European Journal of Immunology*; 30:3585.
Kukita et al. (2004); "RANKL-induced DC-STAMP is essential for osteoclastogenesis"; *The Journal of Experimental Medicine*; 200:941.
Yagi et al. (2005); "DC-STAMP is essential for cell-cell fusion in osteoclasts and foreign body giant cells"; *The Journal of Experimental Medicine*; 202:345.
Griffith, Thomas S. et al. "Functional Analysis of TRAIL Receptors Using Monoclonal Antibodies," *Journal of Immunology*, 162: 2597-2605 (1999).
Miyamoto, Takeshi et al. "The Dendritic cell-specific transmembrane protein DC-STAMP is essential for osteoclast fusion and osteoclast bone-resorbing activity," Mod. Rheumatol 16:341-342 (2006).
Itonaga et al. "Effect of osteoprotegerin and osteoprotegerin ligand on osteoclast formation by arthroplasty membrane derived macrophages." *Annals of Rheumatic Diseases* 59:26-31 (2000).
Suda et al. "Modulation of osteoclast differentiation and function by the new members of the tumor necrosis factor receptor and ligand families." *Endocrine Reviews* 20: 345-357 (1999).
Rho et al. "Gene expression profiling of osteoclast differentiation by combined suppression subtractive hybridization (SSH) and cDNA microarray analysis." *DNA and Cell Biology* 21:541-549 (2002).
Boyle et al. "Osteoclast differentiation and activation," *Nature* 423: 337-342 (2003).
Kurihara et al. "IL-6 stimulates osteoclast-like multinucleated cell formation in long term human marrow cultures by inducing IL-1 release." *Journal of Immunology* 144:4226-4230 (1990).
Vignery. "Osteoclasts and giant cells: macrophage-macrophage fusion mechanism." International Journal of Experimental Pathology 81: 291-304 (2000).
Non-Final Rejection dated Aug. 5, 2009 in corresponding U.S. Appl. No. 11/502,767 (10 pgs.)

(Continued)

*Primary Examiner* — Xiaozhen Xie
(74) *Attorney, Agent, or Firm* — Dorsey and Whitney LLP

(57) ABSTRACT

The present invention relates to a method of detecting metabolic bone disorders using a gene expressed at a high level in osteoclasts, a method of screening for a compound effective for treatment and/or prevention of metabolic bone disorders, and a pharmaceutical composition for treatment and/or prevention of metabolic bone disorders. Specifically, the present invention relates to a method of detecting metabolic bone disorders using expression of the human DC-STAMP gene as an indicator, a pharmaceutical composition containing an antibody which is capable of specifically recognizing human DC-STAMP and suppressing formation of osteoclasts, and so forth.

13 Claims, 12 Drawing Sheets

(56) References Cited

OTHER PUBLICATIONS

Response to Non-Final Rejection dated Dec. 3, 2009 in corresponding U.S. Appl. No. 11/502,767 (16pgs).

Ding, Chunming et al. "Quantitative Analysis of Nucleic Acids—The last Few Years of Progress," *Journal of Biochemistry and Molecular Biology*, 27(1): 1-10 (Jan. 2004).

Kruger, Nicholas J. "Detection of Polypeptides on Immunoblots Using Secondary Antibodies or Protein A," *Methods in Molecular Biology*, vol. 32, edited by J.M. Walker, Humana Press Inc., Totowa, NJ, pp. 215-226 (Jan. 1, 1994).

Gegnas, Laura D. "Patent Focus on Agents for Osteoporosis: Sep. 1999-Feb. 2000," *Exp. Opin. Ther. Patents*, 10(6): 833-846 (2000).

Final office action dated Mar. 18, 2010, in corresponding U.S. Appl. No. 11/502,767.

Supplemental European Search Report dated Sep. 17, 2009, in corresponding European Patent Application No. 05710273.7.

First office action dated Apr. 7, 2010, in corresponding European Patent Application No. 05710273.7.

PCT International Search Report dated Mar. 22, 2005, for corresponding PCT Application No. PCT/JP2006/002373.

International Preliminary Report on Patentability dated Sep. 19, 2006, for corresponding PCT Application No. PCT/JP2006/002373.

Staege et al. "Two novel genes FIND and LIND differentially expressed in deactivated and *Listeria*-infected human macrophages," Immunogenetics (2001) 53:105-113.

Elbashir et al. "RNA interference is mediated by 21- and 22-nucleotide RNAs," Genes & Development (2001) 15:188-200.

"Transcription factor purification utilizing protein to protein affinity," Experimental Medicine, Supplementary volume, Biomanual series 5, pp. 215-219 (published by Yodosha Co., Ltd.).

\* cited by examiner

** $P < 0.01$
*** $P < 0.001$

* $P < 0.05$
** $P < 0.01$

Figure 10
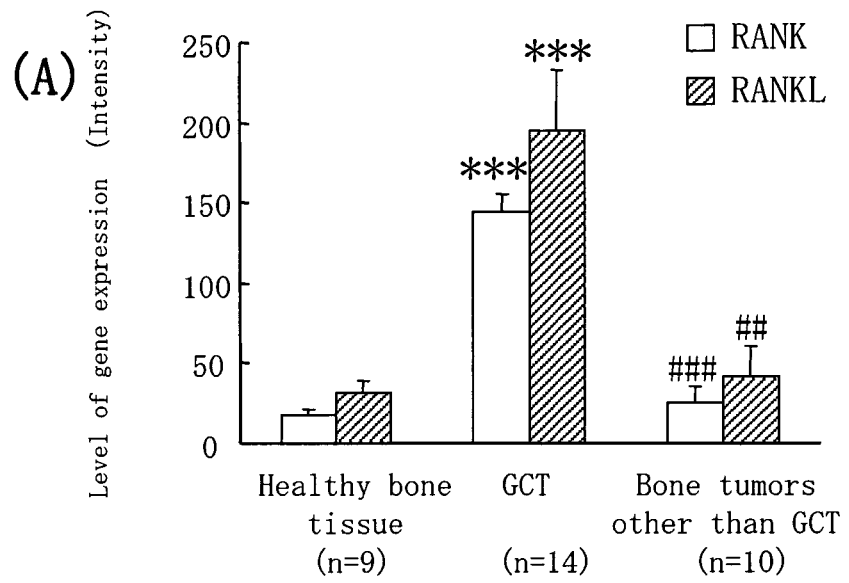
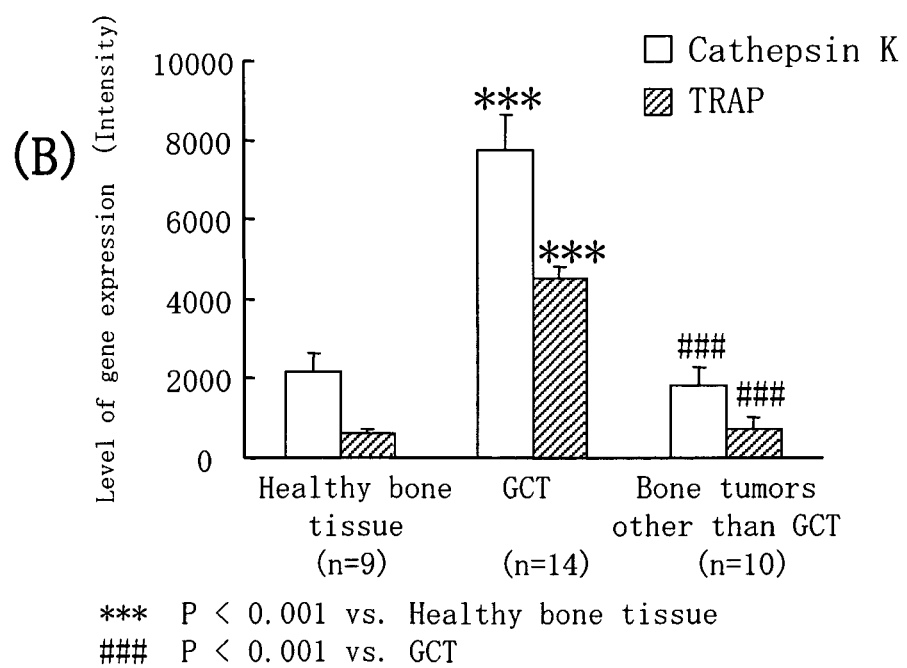

*** $P < 0.001$ vs. Healthy bone tissue
$P < 0.001$ vs. GCT

ANTIBODY TARGETING OSTEOCLAST-ASSOCIATED PROTEIN

RELATED APPLICATION DATA

This application is a Continuation of International Patent Application Serial No. PCT/JP2005/002373, filed Feb. 9, 2005, entitled ANTIBODY TARGETING OSTEOCLAST-ASSOCIATED PROTEIN, which application claims benefit of Japanese Patent Application Serial No. 2004-035216, filed Feb. 12, 2004, entitled ANTIBODY TARGETING OSTEOCLAST-ASSOCIATED PROTEIN, which applications are incorporated herein by reference in their entireties.

TECHNICAL FIELD

The present invention relates to substances useful as agents for treatment and/or prevention of metabolic bone disorders, methods of screening for substances useful as agents for treatment and/or prevention of metabolic bone disorders, methods of detecting metabolic bone disorders, and methods of treating and/or preventing metabolic bone disorders.

BACKGROUND ART

Bone is known to be a dynamic organ which constantly cycles between formation and resorption for reconstruction in order to change its own morphology and to maintain blood calcium levels. Healthy bone maintains an equilibrium between bone formation by osteoblasts, bone resorption by osteoclasts, and its bone mass constant. In contrast, when the equilibrium between bone formation and bone resorption is lost, a metabolic bone disorder such as osteoporosis can develop (Endocrinological Review 13, 66-80, 1992; and Principles of Bone Biology pp. 87-102, 1996, Academic Press, New York).

Many factors involved in regulation of bone metabolism have been reported, including systemic hormones and local cytokines, and they serve together to form and maintain bone (Endocrinological Review 13, 66-80, 1992; and Endocrinological Review 17, 308-332, 1996). A change in bone tissue with aging is widely recognized as a cause of osteoporosis, but the mechanism of its development encompasses various factors, for example, a lower secretion of sex hormones and an abnormality of receptors for the hormones, expression of aging genes, failure to differentiate into osteoclasts and/or osteoblasts and dysfunction of those cells, and thus, as a physiological event due to aging, it is poorly understood. Osteoporosis is largely divided between osteoporosis after menopause due to a lower secretion of estrogen and senile osteoporosis due to aging, but advancement of basic research on the mechanisms of regulation of bone formation and bone resorption is essential to elucidate the mechanism of its development and to develop therapeutic agents.

Osteoclasts are multinucleate cells derived from hematopoietic stem cells, they release chloride and hydrogen ions on the bone surface to which they adhere to acidify the space between the bone surface and the cells themselves (American Journal of Physiology 260, C1315-C1324, 1991). This causes decomposition of calcium phosphate and activation of acid proteases, leading to bone resorption.

Osteoclast precursor cells have been found to be differentiated into osteoclasts by stimulation with RANKL (receptor activator of NF-κB ligand) expressed on the cell membrane of osteoblasts/stromal cells present on the surface of bone (Proceedings of the National Academy of Science of the United States of America 95, 3597-3602, 1998; and Cell 93, 165-176, 1998). It has been shown that RANKL is a membrane-bound factor produced by osteoblasts/stromal cells, its expression is regulated by a bone resorption factor; RANKL induces differentiation of preosteoclastic cells into multinucleate osteoclasts (Proceedings of the National Academy of Science of the United States of America 95, 3597-3602, 1998; and Journal of Bone and Mineral Research 23, S222, 1998). Furthermore, knockout mice devoid of RANKL have been found to develop a typical osteopetrosis, which has verified that RANKL is a physiological inducer for differentiation into osteoclasts (Nature 397, 315-323, 1999).

To treat a bone disorder or shorten the duration of treatment, bisphosphonates, activated vitamin $D_3$, calcitonin and its derivatives, hormone preparations such as estradiol, SERMs (selective estrogen receptor modulators), ipriflavone, vitamin $K_2$ (menatetrenone), calcium preparations and the like are currently used. However, these drugs have not always exhibited a satisfactory therapeutic effect, and thus there has been a desire to develop more potent drugs.

Dendritic cells (referred to as "DC" hereinafter) are specialized antigen-presenting cells of the immune system and distributed throughout the entire body. The dendritic cell-specific transmembrane protein (referred to as "DC-STAMP" hereinafter) is a protein extending across the cell membrane of dendritic cells, that has been cloned from the cDNA library of monocyte-derived DCs (European Journal of Immunology 30, 3585-3590, 2000). One human DC-STAMP cDNA has been reported (GenBank Accession No: NM_030788) and two murine DC-STAMP cDNAs have been reported which are a long sequence cDNA containing the third exon (GenBank Accession No: AB109560) and a splice variant having a short third exon (GenBank Accession No: AB109561), respectively. An amino acid sequence homology of about 74% has been identified between the human DC-STAMP and the murine DC-STAMP. As a result of hydrophobicity analysis for the amino acid sequences, the DC-STAMPs are predicted to have seven transmembrane domains. The murine splice variant having a short third exon is considered to have the seventh transmembrane domain deleted, and is thus denoted by DC-STAMP ΔT7 hereinafter.

DC-STAMP is reported to be more highly expressed following inactivation of mononuclear phagocytes with IL-4, but less highly expressed following their inactivation with dexamethasone (Immunogenetics 53, 105-113, 2001). However, the association of DC-STAMP with differentiation into osteoclasts still remains to be elucidated.

DISCLOSURE OF THE INVENTION

The objects of the present invention are to provide a new method of testing a substance to inhibit specific genes, which are expressed in various metabolic bone disorders such as bone destruction seen in osteoporosis, rheumatoid arthritis, metastasis of cancer cells to bone and the like; and to provide a substance to inhibit osteoclastic activities or an agent to prevent and/or treat metabolic bone disorders.

The present inventors have attempted to elucidate the functions of differentiation into osteoclasts and their maturation and activation in order to identify an agent effective to treat and/or prevent metabolic bone disorders. As a result, it has been found that DC-STAMP is involved in differentiation into osteoclasts and their maturation and activation, and that a lower expression of DC-STAMP leads to a lower differentiation of osteoclasts. The present invention is based on these findings.

Specifically, the present invention comprises:
(1) an antibody capable of specifically binding to DC-STAMP and suppressing formation of osteoclasts;
(2) an antibody capable of specifically binding to at least one protein selected from the group consisting of: a protein having an amino acid sequence shown in SEQ ID NO: 2 in the Sequence Listing, a protein having an amino acid sequence shown in SEQ ID NO: 4, and a protein having an amino acid sequence shown in SEQ ID NO: 6 in the Sequence Listing, and suppressing formation of osteoclasts;
(3) the antibody according to (1) or (2), characterized in that the antibody is a monoclonal antibody;
(4) the antibody according to any one of (1) to (3), characterized in that the antibody is humanized;
(5) the antibody according to any one of (1) to (4), characterized in that the antibody is a complete human antibody;
(6) the antibody according to any one of (1) to (5), characterized in that the antibody is an IgG antibody;
(7) a method of detecting a metabolic bone disorder, comprising the steps of:
1) extracting a total RNA fraction from a test sample taken from a subject;
2) extracting a total RNA fraction from a test sample taken from a healthy person;
3) measuring the expression level of a polynucleotide according to the following a) or b) in the total RNA fraction from step 1) and in the total RNA fraction from step 2), respectively, wherein the polynucleotide is:
a) a polynucleotide having a nucleotide sequence shown in at least one of SEQ ID NOS: 1, 3 and 5 in the Sequence Listing; or
b) a polynucleotide capable of hybridizing, under stringent conditions, with a polynucleotide having a nucleotide sequence complementary to a polynucleotide according to the above a); and
4) analyzing a difference in the expression level of the polynucleotide measured according to step 3) between the total RNA fraction from step 1) and the total RNA fraction from step 2) to detect a metabolic bone disorder in the subject according to step 1);
(8) a method of detecting a metabolic bone disorder, comprising the steps of:
1) measuring the expression level of a protein having an amino acid sequence shown in at least one of: SEQ ID NOS: 2, 4 and 6 in the Sequence Listing in a test sample taken from a subject;
2) measuring the expression level of the at least one protein according to step 1) in a test sample taken from a healthy person; and
3) analyzing a difference in the expression level between the protein measured in step 1) and the protein measured in step 2) to detect a metabolic bone disorder in the subject;
(9) the method according to (7) or (8), characterized in that the metabolic bone disorder is osteoporosis, rheumatoid arthritis and/or cancerous hypercalcemia;
(10) the method according to (7) or (8), characterized in that the metabolic bone disorder is osteoporosis;
(11) the method according to (7) or (8), characterized in that the metabolic bone disorder is rheumatoid arthritis;
(12) the method according to (7) or (8), characterized in that the metabolic bone disorder is cancerous hypercalcemia;
(13) the method according to any one of (7) and (9) to (12), characterized in that the expression level of the polynucleotide is measured by a method selected from northern blotting, dot blotting, slot blotting, RT-PCR, ribonuclease protection assay, or run-on assay;
(14) the method according to any one of (7) and (9) to (12), characterized in that the expression level of the polynucleotide is measured using a gene chip or gene array, wherein the gene chip or gene array is produced from a set of complementary DNAs derived from the test sample or a group of DNAs each having a partial sequence of each DNA member of the set;
(15) the method according to any one of (8) to (12), characterized in that the expression level of the protein is measured using an antibody or a ligand capable of specifically binding to the protein;
(16) the method according to any one of (8) to (12), characterized in that the expression level of the protein is measured by a method selected from western blotting, dot blotting, slot blotting, or enzyme-linked immunosorbent assay (ELISA);
(17) a kit for detecting a metabolic bone disorder, comprising at least one component selected from the group consisting of:
1) an oligonucleotide primer having a length of 15 to 30 contiguous nucleotides for specific amplification of a polynucleotide having a nucleotide sequence shown in at least one of SEQ ID NOS: 1, 3 and 5 in the Sequence Listing;
2) a polynucleotide probe having 15 or more contiguous nucleotides capable of hybridizing, under stringent conditions, with a polynucleotide having a nucleotide sequence shown in at least one of SEQ ID NOS: 1, 3 and 5 in the Sequence Listing, for detection of the polynucleotide; and
3) a solid-phase sample with a polynucleotide having a nucleotide sequence shown in at least one of SEQ ID NOS: 1, 3 and 5 in the Sequence Listing immobilized thereon;
(18) a kit for detecting a metabolic bone disorder, comprising:
1) an antibody capable of specifically binding to a protein having an amino acid sequence shown in at least one of SEQ ID NOS: 2, 4 and 6 in the Sequence Listing, for detection of the protein; and
2) a secondary antibody capable of binding to the antibody according to 1);
(19) the kit according to (17) or (18), characterized in that the metabolic bone disorder is osteoporosis, rheumatoid arthritis or cancerous hypercalcemia;
(20) the kit according to (17) or (18), characterized in that the metabolic bone disorder is osteoporosis;
(21) the kit according to (17) or (18), characterized in that the metabolic bone disorder is rheumatoid arthritis;
(22) the kit according to (17) or (18), characterized in that the metabolic bone disorder is cancerous hypercalcemia;
(23) a pharmaceutical composition for treatment of a metabolic bone disorder, characterized in that the pharmaceutical composition contains at least one of the antibodies according to (1) to (6);
(24) a pharmaceutical composition for treatment of a metabolic bone disorder, characterized in that the pharmaceutical composition contains at least one of the antibodies according to (1) to (6) and at least one component selected from the group consisting of: bisphosphonates, activated vitamin $D_3$, calcitonin and its derivatives, hormone preparations such as estradiol, SERMs (selective estrogen receptor modulators), ipriflavone, vitamin $K_2$ (menatetrenone), calcium preparations, PTH (parathyroid hormone) preparations, non-steroidal anti-inflammatory agents, anti-TNFα antibodies, anti-PTHrP (parathyroid hormone-related protein) antibodies, IL-1 receptor antagonists, anti-RANKL antibodies and OCIF (osteoclastogenesis inhibitory factor);
(25) a pharmaceutical composition for treatment of a metabolic bone disorder, comprising an oligonucleotide having a nucleotide sequence complementary to a nucleotide sequence shown in any one of SEQ ID NOS: 1, 3 and 5 in the Sequence Listing, or to a partial sequence thereof;

(26) the pharmaceutical composition according to any one of (23) to (25), characterized in that the metabolic bone disorder is osteoporosis, rheumatoid arthritis or cancerous hypercalcemia;

(27) the pharmaceutical composition according to any one of (23) to (25), characterized in that the metabolic bone disorder is osteoporosis;

(28) the pharmaceutical composition according to any one of (23) to (25), characterized in that the metabolic bone disorder is rheumatoid arthritis;

(29) the pharmaceutical composition according to any one of (23) to (25), characterized in that the metabolic bone disorder is cancerous hypercalcemia;

(30) a method of screening for a substance effective to treat and/or prevent a metabolic bone disorder, comprising the steps of:
1) extracting a total RNA fraction from a mammalian cell culture cultured in a medium containing a test substance;
2) extracting a total RNA fraction from a mammalian cell culture cultured in the absence of the test substance;
3) measuring the expression level, in the total RNA fraction from step 1) and in the total RNA fraction from step 2), respectively, of at least one polynucleotide selected from the group consisting of the following polynucleotides or fragments thereof, wherein the polynucleotides are:
a polynucleotide having a nucleotide sequence shown in SEQ ID NO: 1 in the Sequence Listing; a polynucleotide having a nucleotide sequence shown in SEQ ID NO: 3; and a polynucleotide having a nucleotide sequence shown in SEQ ID NO: 5; and
4) analyzing a difference in the expression level of the polynucleotide measured according to step 3) between the total RNA fraction from step 1) and the total RNA fraction from step 2) to determine the effect of the test substance on treatment and/or prevention of a metabolic bone disorder;

(31) a method of screening for a substance effective to treat and/or prevent a metabolic bone disorder, comprising the steps of:
1) extracting a total RNA fraction from a test sample taken from a mammal to which a test substance has been administered;
2) extracting a total RNA fraction from a test sample taken from a mammal to which the test substance has not been administered;
3) measuring the expression level, in the total RNA fraction from step 1) and in the total RNA fraction from step 2), respectively, of at least one polynucleotide selected from the group consisting of the following polynucleotides or fragments thereof, wherein the polynucleotides are:
a polynucleotide having a nucleotide sequence shown in SEQ ID NO: 1 in the Sequence Listing; a polynucleotide having a nucleotide sequence shown in SEQ ID NO: 3; and a polynucleotide having a nucleotide sequence shown in SEQ ID NO: 5; and
4) analyzing a difference in the expression level of the polynucleotide measured according to step 3) between the total RNA fraction from step 1) and the total RNA fraction from step 2) to determine the effect of the test substance on treatment and/or prevention of a metabolic bone disorder;

(32) a method of screening for a substance effective to treat and/or prevent a metabolic bone disorder, comprising the steps of:
1) measuring the expression level, in a mammalian cell culture cultured in a medium containing a test substance, of at least one protein selected from the group consisting of the following proteins or polypeptide fragments thereof, wherein the proteins are:
a protein having an amino acid sequence shown in SEQ ID NO: 2 in the Sequence Listing; a protein having an amino acid sequence shown in SEQ ID NO: 4; and a protein having an amino acid sequence shown in SEQ ID NO: 6;
2) measuring the expression level, in a mammalian cell culture cultured in a medium free of the test substance, of any one of the proteins according to step 1) using an antibody or a ligand capable of specifically binding to the protein; and
3) analyzing a difference in the expression level between the protein measured in step 1) and the protein measured in step 2) to determine the effect of the test substance on treatment and/or prevention of a metabolic bone disorder;

(33) a method of screening for a substance effective to treat and/or prevent a metabolic bone disorder, comprising the steps of:
1) measuring the expression level, in a test sample taken from a mammal to which a test substance has been administered, of at least one protein selected from the group consisting of the following proteins or polypeptide fragments thereof, wherein the proteins are:
a protein having an amino acid sequence shown in SEQ ID NO: 2 in the Sequence Listing; a protein having an amino acid sequence shown in SEQ ID NO: 4; and a protein having an amino acid sequence shown in SEQ ID NO: 6;
2) measuring the expression level, in a test sample taken from a mammal to which the test substance has not been administered, of any one of the proteins according to step 1) or polypeptide fragments thereof;
3) analyzing a difference in the expression level between the protein measured in step 1) and the protein measured in step 2) to determine the effect of the test substance on treatment and/or prevention of a metabolic bone disorder;

(34) the method according to (30) or (31), characterized in that the expression level of the polynucleotide is measured by a method selected from northern blotting, dot blotting, slot blotting, RT-PCR, ribonuclease protection assay, or run-on assay;

(35) the method according to (30) or (31), characterized in that the expression level of the polynucleotide is measured using a gene chip or gene array, wherein the gene chip or gene array is produced from a set of complementary DNAs derived from the mammalian animal tissue or mammalian animal cells, or a group of DNAs each having a partial sequence of each DNA member of the set; and

(36) the method according to (32) or (33), characterized in that the expression level of the protein is measured using an antibody or a ligand capable of specifically binding to the protein.

BRIEF DESCRIPTION OF THE DRAWINGS

FIG. 10 provides graphs showing expression profiles of genes for human RANK, RANKL, cathepsin K and TRAP in giant cell tumor;

BEST MODE FOR CARRYING OUT THE INVENTION

Figure 1:
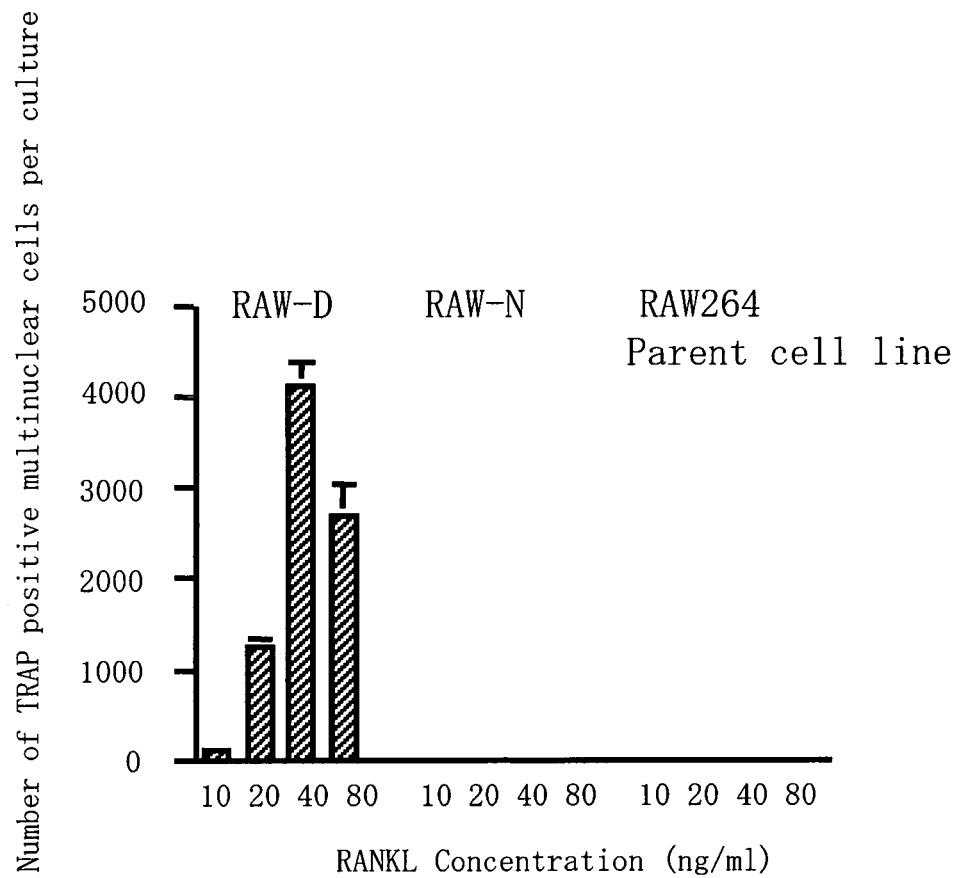
FIG. 1 is a graph showing differentiation of each type of subcloned RAW264 cells into osteoclasts by stimulation with RANKL.

The expression "hybridization under stringent conditions" means hybridization in a commercially available solution, ExpressHyb Hybridization Solution (from Clontech Laboratories Inc.) at 68° C., or hybridization under hybridization conditions on a DNA-fixed filter in the presence of 0.7-1.0 M NaCl at 68° C., followed by washing with a 0.1-2×SSC solution (a 1×SSC solution contains 150 mM NaCl and 15 mM sodium citrate) at 68° C., or hybridization under conditions equivalent thereto.

1. DC-STAMP

The present inventors have found that DC-STAMP is specifically expressed in giant cell tumor. In addition, the present inventors have also found that DC-STAMP is expressed at a higher level when a monocyte-derived cell strain is differentiated into osteoclasts.

The DC-STAMP used in the present invention may be a product directly purified from monocytes, dendritic cells or bone marrow cells of human or non-human mammalian origin (e.g., guinea pig, rat, mouse, chicken, rabbit, pig, sheep, cow, monkey, etc.), a cell membrane fraction prepared from the above cells, a synthetic DC-STAMP made in vitro, or a genetically-engineered product formed in host cells. Specifically, in gene manipulation, a DC-STAMP protein can be obtained by first integrating a DC-STAMP gene into a vector capable of expressing it, then synthesizing DC-STAMP from the vector in a solution containing enzymes necessary for transcription and translation, substrates and energy-supplying materials, or transforming the vector into various species of host cells of prokaryotic or eukaryotic origin to express DC-STAMP.

The nucleotide sequence of the cDNA for the human DC-STAMP is registered as Accession No: NM_030788 with GenBank, and shown in SEQ ID NO: 1 in the Sequence Listing; its amino acid sequence is shown in SEQ ID NO: 2 in the Sequence Listing. The long nucleotide sequence containing the third exon of the cDNA for the murine DC-STAMP is registered as Accession No: AB109560_ with GenBank, and shown in SEQ ID NO: 3 in the Sequence Listing; its amino acid sequence is shown in SEQ ID NO: 4 in the Sequence Listing. The nucleotide sequence having the short third exon of the splice variant cDNA for the murine DC-STAMP is registered as Accession No: AB109561 with GenBank, and shown in SEQ ID NO: 5 in the Sequence Listing; its amino acid sequence is shown in SEQ ID NO: 6 in the Sequence Listing. A cDNA for DC-STAMP can be produced, for example, by carrying out polymerase chain reaction (referred to as "PCR" hereinafter) using a cDNA library expressing DC-STAMP as the template and primers capable of specifically amplifying the DC-STAMP cDNA (Saiki, R. K., et al., Science, (1988) 239, 487-49), which is called the PCR technique.

In addition, cDNA for DC-STAMP includes a polynucleotide which can hybridize under stringent conditions with a polynucleotide having a nucleotide sequence complementary to at least one nucleotide sequence shown in SEQ ID NOS: 1, 3 and 5 in the Sequence Listing and which encodes a protein with a biological activity comparable to DC-STAMP. Furthermore, cDNA for DC-STAMP includes a polynucleotide which is a splicing variant transcribed from the locus for human or murine DC-STAMP or a polynucleotide capable of hybridizing therewith under stringent conditions, and which encodes a protein with a biological activity comparable to DC-STAMP.

Also, DC-STAMP includes a protein having an amino acid sequence formed by substitution, deletion or addition of one or more amino acids in at least one amino acid sequence shown in SEQ ID NOS: 2, 4 and 6 in the Sequence Listing and having a biological activity comparable to DC-STAMP. Furthermore, DC-STAMP includes a protein having an amino acid sequence encoded by a splicing variant transcribed from the locus for human or murine DC-STAMP, or an amino acid sequence formed by substitution, deletion or addition of one or more amino acids therein, and having a biological activity comparable to DC-STAMP.

2. Detection of Metabolic Bone Disorders

Analysis of a group of test samples from various human bone tissues for expression level of the DC-STAMP gene shows that the gene is expressed at a significantly higher level in giant cell tumor (GCT) which is a bone tumor abundant in osteoclastic multinuclear giant cells characterized by clinical findings of osteolytic bone destruction (Bullough et al., Atlas of Orthopedic Pathology 2nd edition, pp. 17.6-17.8, Lippincott Williams & Wilkins Publishers (1992)).

It has been also found that DC-STAMP is expressed at a higher level when a monocyte-derived cell strain is differentiated into osteoclasts.

Accordingly, DC-STAMP is believed to be associated with human conditions, such as GCT, which increase bone resorption. In other words, measurement of the expression level of DC-STAMP in different types of cells and/or different tissues enables determination of the state of metabolic bone disorders which may develop due to over-expression of DC-STAMP. Herein, metabolic bone disorders include, but are not limited to, osteoporosis (osteoporosis after menopause, senile osteoporosis, secondary osteoporosis due to the use of a steroid or immunosuppressant, and osteoporosis associated with rheumatoid arthritis), bone destruction caused by rheumatoid arthritis, cancerous hypercalcemia, bone destruction caused by multiple myeloma or metastasis of cancer to bone, loss of teeth due to dental periostitis, osteolysis around artificial joints, bone destruction due to chronic osteomyelitis, Paget's disease of bone, renal osteodystrophy and osteogenesis imperfecta.

The "test sample" used to examine the expression level of DC-STAMP refers to a specimen from a tissue, such as blood, bone marrow, bone, body fluid, prostate, testis, penis, bladder, kidney, oral cavity, pharynx, lip, tongue, gingiva, nasopharynx, esophagus, stomach, small intestine, large intestine, colon, liver, gallbladder, pancreas, nose, lung, soft tissue, skin, breast, uterus, ovary, brain, thyroid, lymph node, muscle, fat tissue or the like, or from an excretion or the like, but it is preferably blood or bone marrow in the present invention.

(1) The Method of Detecting a Metabolic Bone Disorder Utilizing the Expression Level of the DC-STAMP Gene The method of detecting a metabolic bone disorder utilizing the expression level of the DC-STAMP gene is specifically a method comprising the steps of:

1) extracting a total RNA fraction from a test sample taken from a subject;

2) extracting a total RNA fraction from a test sample taken from a healthy person;

3) measuring the expression level of the DC-STAMP gene in the total RNA fraction from step 1) and in the total RNA fraction from step 2), respectively; and 4) analyzing a difference in the expression level of the gene measured according to step 3) between the total RNA fraction from step 1) and the total RNA fraction from step 2) to detect a metabolic bone disorder in the subject according to step 1).

The steps will be described specifically below.

a) The step 1) of extracting a total RNA fraction from a test sample taken from a subject In extraction of the total RNA fraction from the test sample, a human tissue (obtained according to a procedure compliant with a suitable ethical laboratory standard) may be suspended directly in a solvent for RNA extraction (for example, phenol or the like which contains a component to inactivate ribonucleases), or its cells may be recovered by a method of scraping the tissue carefully to leave the cells of the tissue intact, or treating the tissue with a protease such as trypsin to extract the cells gently therefrom, and then subjected immediately to the step of RNA extraction.

The RNA may be extracted by any suitable method including ultracentrifugation in guanidine thiocyanate/cesium chloride, guanidine thiocyanate/hot phenol, guanidine hydrochloride, and acidic guanidine thiocyanate/phenol/chloroform (Chomczynski, P. and Sacchi, N., Anal. Biochem. (1987), 162, 156-159), but preferably by acidic guanidine thiocyanate/phenol/chloroform. Additionally, a commercially available reagent, such as a reagent for RNA extraction (for example, ISOGEN (made by Nippon Gene Co., Ltd.) or TRIZOL reagent (made by Gibco BRL)), may be used in accordance with the protocol provided with the reagent.

Preferably, the resulting total RNA fraction may be further purified into the mRNA only as needed. The choice of purification method is not limited, but the mRNA may be purified, for example, by adsorbing the mRNA to a biotinylated oligo (dT) probe, capturing the mRNA on streptavidin-attached paramagnetic particles via binding of biotin to streptavidin, washing the particles and then eluting the mRNA. Another method may be employed in which the mRNA is adsorbed to an oligo(dT)-bound cellulose column and then eluted. However, the mRNA purification step is not essential for the inventive method, the total RNA fraction may be used in a subsequent step if expression of a polynucleotide of interest can be detected.

b) The step 2) of extracting a total RNA fraction from a test sample taken from a healthy person In the present invention, a healthy person means a person that is not afflicted with a metabolic bone disorder. It may be determined if a person is healthy or not by measuring the DC-STAMP level in the person and seeing if the level is, or is not, within a predetermined numerical range of the normal DC-STAMP level. Also it may be determined if a subject is healthy or not by preliminary examination of the correlation between DC-STAMP levels and the level of formation of a metabolic bone disorder, and measuring the expression level of DC-STAMP in a test sample taken from the subject. A total RNA fraction from a healthy person may be prepared according to the above-mentioned step 1).

c) The step 3) of measuring the expression level of the DC-STAMP gene in the total RNA fraction from step 1) and in the total RNA fraction from step 2), respectively Herein, the expression level of the DC-STAMP gene is represented by the expression level of a polynucleotide having a nucleotide sequence shown in SEQ ID NO: 1 in the Sequence Listing, or of a polynucleotide capable of hybridizing, under stringent conditions, with a polynucleotide having a nucleotide sequence complementary to the nucleotide sequence shown in SEQ ID NO: 1 in the Sequence Listing.

The expression level of the DC-STAMP gene may be measured by a method using an immobilized sample or by one of several other methods, as described below.

(a) Measurements Using Immobilized Samples (i) Immobilized Samples

The immobilized sample includes, for example, the following:

(i-1) Gene chips

Gene chips can be used which are formed by immobilizing anti-sense oligonucleotides synthesized based on EST (expressed sequence tag) sequences or mRNA sequences. These chips include, but are not limited to, gene chips made by Affymetrix Inc. (Lipshutz, R. J. et al., Nature Genet. (1999) 21, supplement, 20-24), and may be prepared based on any known method. If mRNA from human cells is to be analyzed, the gene chip is preferably of human origin, such as a human U95 or U133 set made by Affymetrix Inc. However, it is not limited to these but may be derived, for example, from a closely related animal species.

(i-2) Arrays or Membrane Filters Formed by Immobilizing cDNAs or RT-PCR Products Prepared from Human Total RNA or Specific-Tissue Total RNA:

These cDNAs or RT-PCR products are cloned products obtained by performing reverse transcription or PCR with primers prepared on the basis of sequence information such as from a database of human ESTs. The cDNAs or RT-PCR products may be prepared from total RNA, which is expressed at different levels in persons suffering from a metabolic bone disorder and persons without the disorder, and can be selected in advance by means of the subtraction technique (Diatchenki, L. et al., Proc. Natl. Acad. Sci. USA, (1996) 93, 6025-6030), the differential display technique (Liang, P. et al., Nucleic Acids Res., (1992) 23, 3685-3690) or the like. Arrays or membrane filters may be commercial products (for example, IntelliGene made by Takara Bio Inc.), or they may be prepared by immobilizing the above-described cDNAs or RT-PCR products with a commercially available spotter (for example, GMS417 Arrayer made by Takara Bio Inc.).

(ii) Preparation and Analysis of Probes

Labeled probes are prepared not by labeling a particular mRNA clone, but by labeling all the expressed mRNAs. The starting material for preparation of probes may be unpurified mRNAs, but is desirably poly(A)+ RNAs purified by a method described above. The preparation, detection and analysis of labeled probes is described below, the choice of method depending on the different immobilized samples.

(ii-1) Gene Chips Made by Affymetrix Inc.

Biotin-labeled cRNA probes are prepared according to a protocol (a technical manual for expression analysis by Affymetrix Inc.) provided with a gene chip made by Affymetrix Inc. Then, the probes are hybridized and analyzed using an analytic instrument (GeneChip Fluidics Station 400) made by Affymetrix Inc. according to a protocol (the technical manual for expression analysis) provided with the gene chip made by Affymetrix Inc., through detection and analysis of light emission from avidin.

(ii-2) Arrays

In preparation of cDNAs from poly(A)$^+$RNAs by reverse transcription, it is necessary to label the cDNAs to detect them. If they are to be labeled with a fluorescent dye, d-UTP or the like labeled with the fluorescent dye (for example, Cy3 or Cy5) is added into the mixture to label the cDNAs. At this time, if poly(A)$^+$RNAs from a test sample taken from a subject and poly(A)$^+$RNAs from a test sample taken from a healthy person are labeled with different dyes, respectively, the poly(A)$^+$RNAs from both test samples may be mixed in a subsequent hybridization. If a commercially available array from Takara Bio Inc. is used, for example, hybridization and washing are carried out according to a protocol provided by the company, and then fluorescent signals are detected by a fluorescent signal detector (for example, a GMS418 array scanner made by Takara Bio Inc. or the like) and analyzed. However, the choice of array used here is not limited to commercial products but may be made in house or specially commissioned.

(ii-3) Membrane Filters

To prepare cDNAs from poly(A)$^+$RNAs with a reverse transcriptase, labeled probes are prepared by adding a radioactive isotope (for example, d-CTP or the like), then hybridized as usual, for example, using an Atlas System (made by Clontech Laboratories Inc.) which is a commercially available filter microarray, and washed; this is followed by detection and analysis using an analytic instrument (for example, an Atlas Image made by Clontech Laboratories Inc.).

In any method according to the above (ii-1) to (ii-3), probes derived from each human tissue are hybridized with the same lot of immobilized samples. The conditions of hybridization are the same, except for the use of different probes. If the different probes are labeled with different fluorescent dyes, a mixture of the two different probes can be hybridized with the same immobilized sample at once to read fluorescence intensities (Brown, P. O. et al., Nature Genet., (1999) 21, supplement, 33-37).

(b) Other Methods of Measurement

Other methods of measurement include, but are not limited to, subtraction cloning (Experimental Medicine, Separate Volume, New Handbook on Genetic Engineering, Yodosha Co; Ltd. (1996), 32-35), differential display (Basic Experimental Biochemistry No. 4, Nucleic Acids and Genes II; Applications, Tokyo Kagaku Dozin Co., Ltd. (2001), 125-128), and methods using a reporter gene (chloramphenicol acetyltransferase, for example, pCAT3-Basic Vector from Promega Corporation; β-galactosidase, for example, pβgal-Basic from Promega Corporation; secretory alkaline phosphatase, for example, pSEAP2-Basic from Clontech; and green fluorescent protein, for example, pEGFP-1 from Clontech Laboratories Inc.).

d) The step 4) of analyzing a difference in the expression level of the gene measured according to step 3) between the total RNA fraction from step 1) and the total RNA fraction from step 2) to detect a metabolic bone disorder in the subject according to step 1)

When a difference in expression level of DC-STAMP is examined between a test sample from a healthy person and that from a subject, and if the latter has a significantly higher expression level, then the subject is liable to suffer from a metabolic bone disorder, which thus may be detected. The term "a significantly higher expression level" means that the subject test sample has a significantly higher average difference value for the DC-STAMP gene than for the healthy test sample, for example, when a gene chip from Affymetrix Inc. is used together with microarray Suite Ver. 3.0 from Affymetrix Inc. as analytic tool. Also, to detect a metabolic bone disorder, the DC-STAMP gene expression level in a subject may be measured to check if the level is, or is not, within a predetermined numerical range of the normal level, and if the level is above the normal range, the subject may be determined to suffer from a metabolic bone disorder. In addition, it may be determined if a subject is healthy or not by making a preliminary examination of the correlation between expression levels of the DC-STAMP gene and the level of formation of a metabolic bone disorder in healthy people, and measuring the expression level of the DC-STAMP gene in a test sample taken from the subject.

(2) The Method of Detecting a Metabolic Bone Disorder Utilizing the Expression Level of DC-STAMP (Expression Level of the Protein)

A method of detecting a metabolic bone disorder utilizing the expression level of DC-STAMP is specifically a method comprising the steps of:

1) measuring the expression level of DC-STAMP in a test sample taken from a subject;

2) measuring the expression level of the protein according to step 1) in a test sample taken from a healthy person; and 3) analyzing a difference in the level of expression between the protein measured in step 1) and the protein measured in step 2) to detect a metabolic bone disorder in the subject.

The steps will be described specifically below:

1) The Step 1) of Measuring the Expression Level of DC-STAMP in a Test Sample Taken from a Subject (a) Preparation of a Sample for Protein Assay from a Test Sample A test sample optionally may be centrifuged at a high speed to remove insoluble matter, and then used to prepare an ELISA/RIA or western blotting sample.

The ELISA/RIA sample may be, for example, an extract itself obtained from blood or bone marrow, or optionally a dilution thereof in a buffer. A western blotting sample (for electrophoresis) may be prepared by mixing, for example, an extract itself obtained from blood or bone marrow, or optionally a dilution thereof, in a buffer with a sample buffer containing 2-mercaptoethanol (made by Sigma Co., for example) for electrophoresis on SDS-polyacrylamide. In dot/slot blotting, the sample may be, for example, an extract itself obtained from blood or bone marrow, or optionally a dilution in a buffer, and it is adsorbed directly onto a membrane with a blotting device or the like.

(b) Immobilization of a Sample

To specifically detect the protein in a sample prepared as described above, the sample may not be immobilized, but may be precipitated by immunoprecipitation, a ligand-binding method or the like, or may be immobilized as it is. Membranes that can be used for immobilizing the protein used in western blotting, dot blotting or slot blotting include a nitrocellulose membrane (made by Bio-Rad Laboratories Inc., for example), nylon membrane (for example, Hibond-ECL from Amersham Pharmacia Biotech), cotton membrane (for example, Blot Absorbent Filter from Bio-Rad Laboratories Inc.) or polyvinylidene difluoride (PVDF) membrane (made by Bio-Rad Laboratories Inc., for example).

To detect and quantify the protein by the ELISA/RIA technique, the sample or a dilution thereof (for example, diluted with phosphate buffered saline (referred to as "PBS") containing 0.05% sodium azide) is placed in a special 96-well plate (for example, Immunoplate Maxisorp from Nalge Nunc International) and left standing from 4° C. to room temperature overnight or at 37° C. for 1-3 hours, thereby adsorbing the protein onto the bottom of the wells for immobilization.

An antibody against DC-STAMP can be obtained by immunizing an animal with DC-STAMP or any polypeptide forming a part of the amino acid sequence of DC-STAMP, collecting the antibody produced in vivo and purifying it, according to a standard method (for example, see Experimental Biochemistry New Lecture Series 1: Proteins 1, pp. 389-397, 1992). Moreover, a monoclonal antibody can be obtained by fusing antibody-forming cells capable of producing an anti-DC-STAMP antibody with myeloma cells to establish a hybridoma, according to a known method (for example, Kohler and Milstein, Nature, (1975) 256, 495-497; Kennet, R. ed., Monoclonal Antibody, (1980) 365-367, Prenum Press, N.Y.).

The DC-STAMP used as the antigen can be obtained by expression of the DC-STAMP gene in host cells by genetic engineering. Specifically, a vector capable of expressing the DC-STAMP gene may be created and transfected into host cells to express the gene and then DC-STAMP, which can then be purified. Alternatively, the host cells themselves having DC-STAMP expressed therein, or membrane fragments thereof, may be used as the antigen.

(c) Measurements of the Level of Expression of DC-STAMP

The level of expression of DC-STAMP is indicated by the level of expression of a protein having an amino acid sequence shown in SEQ ID NO: 2 in the Sequence Listing.

This expression level can be measured using the above-described anti-DC-STAMP antibody by a known method such as western blotting or dot/slot blotting.

2) The Step 2) of Measuring the Level of Expression of the Protein According to Step 1) in a Test Sample Taken from a Healthy Person The level of expression of DC-STAMP in a test sample taken from a healthy person is measured by a similar method to that in step 1).

3) The Step 3) of Analyzing a Difference in the Expression Levels Between the Protein Measured in Step 1) and the Protein Measured in Step 2) to Detect a Metabolic Bone Disorder in the Subject A difference in the expression levels of DC-STAMP between a test sample from a healthy person and a test sample from a subject is analyzed to see if the subject's test sample expresses DC-STAMP at a significantly higher level; a test sample with a higher expression level of DC-STAMP would be determined to be from a subject liable to suffer from or suffering a metabolic bone disorder.

Also, a DC-STAMP level in a subject may be measured to check if the level is, or is not, within a predetermined normal level numerical range, and if the level is above the normal range, the subject may be determined to suffer from a metabolic bone disorder to detect the metabolic bone disorder. In addition, it may be determined if a subject is healthy or not by preliminary examination of the correlation between the expression levels of DC-STAMP and the levels of bone metabolism in healthy people, and measuring the expression level of DC-STAMP in a test sample taken from the subject.

3. Assay of the DC-STAMP Gene and DC-STAMP

The DC-STAMP gene and DC-STAMP are expressed specifically in Giant Cell Tumor and at a higher level when a monocyte-derived cell strain is differentiated into osteoclasts.

(1) Functional Analysis of the DC-STAMP Gene and DC-STAMP Utilizing Over-Expression of DC-STAMP To examine the function of DC-STAMP, a full-length cDNA is first obtained from a cDNA library derived from cells expressing DC-STAMP, according to a known method such as colony hybridization. The full-length cDNA is introduced into human cells or non-human mammalian cells (for example, cells from guinea pig, rat, mouse, chicken, rabbit, pig, sheep, cow, monkey, or the like) to express it at a high level and thus examine the effect of the high expression level on the cells.

To express cDNA in individual animals, the resultant full-length cDNA is integrated into a viral vector and administered to them. The cDNA is integrated into a viral vector, for example, a DNA virus, such as retrovirus, adenovirus, adeno-associated virus, herpesvirus, vaccinia virus, poxvirus or poliovirus, or a RNA virus for gene transfer into the animals. Particularly preferable viruses include retrovirus, adenovirus, adeno-associated virus and vaccinia virus.

A non-virus-mediated gene transfer may include direct injection of an expression plasmid into a muscle (DNA vaccination), the liposome method, lipofection, microinjection, calcium phosphate transfection and electroporation, particularly preferred are DNA vaccination and the liposome method.

Full-length cDNA may be transferred into cultured cells, such as monocyte-derived cells, lymph node-derived cells, myocytes, hepatocytes, adipocytes or dermal cells which are of human or non-human mammalian origin (e.g., guinea pig, rat, mouse, chicken, rabbit, pig, sheep, cow, monkey, etc.), for expression at a high level and to examine the effect of the high-level expression on the functions of each type of cells, such as on the function of bone metabolism, including the differentiation into, and maturation of, osteoclasts, or on the cell morphology.

In transfer of the full-length cDNA into the animal or cells, a suitable promoter and a sequence associated with phenotypic expression are integrated into the vector, which will then be used to transform the host cells. Expression vectors used for vertebrate animal cells generally have a promoter located upstream of the gene to be expressed, splice junctions for RNA, a polyadenylation site, a transcription termination sequence and others, and optionally a replication origin. Examples of expression vectors include, but are not limited to, pSV2dhfr having the SV40 early promoter (Subramani, S. et al., Mol. Cell. Biol., (1981) 1, 854-864), and pCI-neo (from Promega Corporation), retroviral vectors pLNCX, pLNSX, pLXIN, pSIR (from Clontech Laboratories Inc.), and cosmid vector (Takara Bio Inc.) each of which has the CMV early promoter. The expression vector may be transferred into murine monocyte-derived RAW264.7 cells (ATCC Cat. No. TIB-71), RAW264 cells (ECACC Cat. No. 85062803), or RAW-D cells (Watanabe et al., J. Endocrinol., (2004) 180, 193-201); a dihydrofolate reductase-deficient strain (Urlaub, G. and Chasin, L. A., Proc. Natl. Acad. Sci. USA (1980) 77, 4126-4220) of simian COS cells (Gluzman, Y., Cell, (1981) 23, 175-182; ATCC: CRL-1650) or Chinese hamster ovarian cells (CHO cells; ATCC: CCL-61); human fetal kidney-derived 293 cells (ATCC: CRL-1573) or the like, by means of a method including, but not limited to, the diethylaminoethyl (DEAE)-dextran method (Luthman, H. and Magnusson, G., Nucleic Acids Res., (1983) 11, 1295-1308), phosphate calcium-DNA co-precipitation (Graham, F. L. and van der Eb, A. J., Virology, (1973) 52, 456-457) and pulse electroporation (Neumann, E. et al., EMBO J., (1982) 1, 841-845). Thus, a desired transformant can be obtained.

Moreover, transgenic animals expressing a target gene at a high level can be created from healthy animals by genetic manipulation to examine the effects of high level expression on cell morphology.

(2) Functional Analysis of DC-STAMP Utilizing a Lower Level of Expression of DC-STAMP The function of DC-STAMP can be also analyzed by suppressing DC-STAMP expression and examining the effects of a lower level of expression on differentiation into, and maturation of, osteoclasts, or on the cell morphology.

A suppressor for DC-STAMP expression may be an antisense nucleic acid, a siRNA or the like which acts against the DC-STAMP gene. An inhibitor for DC-STAMP function may be an antibody capable of specifically binding to DC-STAMP.

Suppression of DC-STAMP expression or inhibition of DC-STAMP function can be applied to examine of the effects thereof on the function of each type of cells, specifically, function related to bone metabolism, such as differentiation into, and maturation, of osteoclasts, or on cell morphology. In addition, knockout animals can be created from animals suffering from, or free of, a metabolic bone disorder to examine the resulting state of the cells or tissue.

4. A Kit for Detection of the DC-STAMP Gene and/or DC-STAMP

The DC-STAMP gene and/or DC-STAMP can be detected with a kit containing at least one component selected from the group consisting of the following:

1) an oligonucleotide primer having a length of 15 to 30 contiguous nucleotides for specific amplification of at least one polynucleotide selected from: a polynucleotide having a nucleotide sequence shown in SEQ ID NO: 1 in the Sequence Listing, a polynucleotide having a nucleotide sequence shown in SEQ ID NO: 3, and a polynucleotide having a nucleotide sequence shown in SEQ ID NO: 5;

2) a polynucleotide probe having 15 or more contiguous nucleotides capable of hybridizing, under stringent conditions, with at least one polynucleotide selected from: a polynucleotide having a nucleotide sequence shown in SEQ ID NO: 1 in the Sequence Listing, a polynucleotide having a nucleotide sequence shown in SEQ ID NO: 3, and a polynucleotide having a nucleotide sequence shown in SEQ ID NO: 5, for detection of the polynucleotide;

3) a solid-phase sample with at least one polynucleotide selected from: a polynucleotide having a nucleotide sequence shown in SEQ ID NO: 1 in the Sequence Listing, a polynucleotide having a nucleotide sequence shown in SEQ ID NO: 3, and a polynucleotide having a nucleotide sequence shown in SEQ ID NO: 5, immobilized thereon;

4) an antibody capable of specifically binding to at least one protein selected from: a protein having an amino acid sequence shown in SEQ ID NO: 2 in the Sequence Listing, a protein having an amino acid sequence shown in SEQ ID NO: 4, and a protein having an amino acid sequence shown in SEQ ID NO: 6, for detection of the protein; and 5) a secondary antibody capable of binding to an antibody according to 4).

The primer according to the above 1) can be easily designed in a standard method, for example, using commercially available software for primer design (for example, Wisconsin GCG package Version 10.2) and used for amplification, based on a nucleotide sequence of the DC-STAMP gene (a nucleotide sequence(s) as provided by SEQ ID NOS: 1, 3 and/or 5 in the Sequence Listing). The probe according to the above 2) is a polynucleotide capable of specifically hybridizing with DC-STAMP having a nucleotide length of 100-1500, preferably 300-600. The primer and the probe may be labeled with a suitable label (for example, enzyme label, radioactive label, fluorescent label or the like), and may be added to a linker.

The solid-phase sample according to the above 3) may be prepared by immobilizing the probe according to the above 2) on a solid phase such as a glass plate, nylon membrane and the like. Methods for preparing the solid-phase sample have been described already in subsection "(1) The method of detecting a metabolic bone disorder utilizing the expression level of the DC-STAMP gene" in the section "2. Detection of metabolic bone disorders", and such immobilized samples include gene chips, cDNA arrays, oligo arrays and membrane filters.

The kit of the invention may further contain a thermostable DNA polymerase, dNTPs (a cocktail of dATP, dCTP, dGTP and dTTP) and a buffer. The thermostable DNA polymerase may be exemplified by Taq DNA polymerase, LA Taq DNA polymerase (made by Takara Shuzo Co., Ltd.), Tth DNA polymerase and Pfu DNA polymerase. The buffer may be selected depending on the DNA polymerase used here and may optionally contain $Mg^{2+}$ and the like.

The antibodies according to the above 4) and 5) may be prepared by a method described in subsection "(2) The method of detecting a metabolic bone disorder utilizing the expression level of DC-STAMP (expression level of the protein)" in section "2. Detection of metabolic bone disorders", or in section "6. Production of anti-DC-STAMP antibodies", described later. The antibodies may be labeled with a suitable label (for example, enzyme label, radioactive label, fluorescent label or the like).

The kit of the invention may be used for detection of the DC-STAMP gene and/or DC-STAMP as well as determination of the presence or absence of a metabolic bone disorder and for screening to identify a suppressor of the pathological progress of a metabolic bone disorder.

5. The Method of Screening for a Suppressor of Differentiation into Osteoclasts

In one aspect of the present invention, a method of screening for a suppressor of differentiation into osteoclasts is provided by measuring the expression level of the DC-STAMP gene and/or DC-STAMP.

In one aspect of the present invention, a method of screening a therapeutic and/or preventive substance for metabolic bone disorders may be provided by identifying a substance capable of inhibiting DC-STAMP's activity of enhancing differentiation into osteoclasts.

A "test substance" refers to a substance to be tested for its activity as a suppressor of differentiation into osteoclasts. The test substance can be a compound, microbial metabolite, an extract from plant or animal tissues, derivatives thereof or a mixture thereof. Nucleic acids or derivatives thereof designed to lower the expression level of DC-STAMP (including antisense oligonucleotides, ribozymes, dsRNAs and siRNAs) may be used as the test substance. The test substance may be given at any suitable dose or in any suitable concentration, or at multiple doses prepared, for example, by serial dilution. It may be given in any suitable phase, such as solid or liquid, or as a solution in a suitable buffer, or in a form combined with an additive, such as a stabilizer. If cell culture is used for screening, the cells can be cultured in a medium. The cells may be added to the medium at the start of the culture or during the culture, and also in several aliquots. The period over which the culture is exposed to the test substance may be set, as appropriate, but is preferably from 30 minutes to 2 weeks, more preferably from 30 minutes to 48 hours. If the test substance is given to individual animals, it may be given by oral administration, intravenous injection, intraperitoneal injection, transdermal infusion, subcutaneous injection or by other routes, depending on the physical and/or other properties of the test substance. The interval of time from the administration of the test substance taking the test sample may be set as appropriate.

The cultured cells used in a screening method of the present invention may be healthy mammalian cells, or cells capable of abnormal proliferation, such as cancer cells, as long as they can express DC-STAMP, including, for example, but not limited to, murine monocyte-derived RAW264.7 cells (ATCC Cat. No. TIB-71), RAW264 cells (ECACC Cat. No. 85062803), and RAW-D cells (Watanabe et al., J. Endocrinol., (2004) 180, 193-201); and murine bone marrow-derived primary culture cells. The cultured cells may originate from mammalian species. preferably including, but not being limited to, human, mouse or other animals (e.g., guinea pig, rat, chicken, rabbit, pig, sheep, cow, monkey, etc.). It is more preferable that the cultured cells are mammalian cells overexpressing DC-STAMP, such as RAW264.7 cells, RAW264 cells and RAW-D cells, which all have the DC-STAMP gene introduced therein together with a promoter region for overexpression of DC-STAMP.

The screening method of the invention also includes a method of administering a test substance to individual mammalian animals, rather than culturing cells with the test substance, removing an organ or tissue from the animals, and detecting expression of the DC-STAMP gene in the animal's cells. The organ or tissue from which the gene expression is to be detected has only to express DC-STAMP, but it is preferably a tissue developing a metabolic bone disorder, more preferably bone marrow. A mammalian species used here may be a non-human animal, preferably mouse, rat or guinea pig, more preferably mouse or rat. An animal model having a metabolic bone disorder may be an animal having had an ovary removed, an animal having had a testis removed, a cancer-bearing animal having tumor cells implanted into hypoderm, intraderm, left ventricle, bone marrow, vein, peritoneum or elsewhere, an animal having had a sciatic nerve removed, an animal model for adjuvant arthritis, an animal model for collagen-induced arthritis, an animal model for glucocorticoid-induced osteoporosis, senescence accelerated mice (SAM P6 mice, Matsushita et al., Am. J. Pathol. 125, 276-283 (1986)), an animal having had the thyroid/parathyroid removed, an animal receiving a continuous infusion of parathyroid hormone-related peptides (PTHrP), knockout mice having lost osteoclast inhibitory factor (OCIF) (Mizuno et al., Biochem. Biophys. Res. Commun., (1998) 247, 610-615) or the like. Additionally, an animal model having lost teeth due to periodontal disease or an animal created to overexpress DC-STAMP may be used. Test substances selected by screening may be administered to the above-described animal models to measure the parameters that vary with metabolic bone disorder, such as the number of osteoclasts, bone density and bone strength in bone tissue, or blood $Ca^{2+}$ level, and thereby evaluate their therapeutic and/or preventive effect on metabolic bone disorder.

The cells for culture used in the present invention may be cultured under any conditions so long as they can express DC-STAMP by addition of RANKL and TNF-α in the absence of a test substance. For instance, the cells may be cultured under known conditions provided that they can express DC-STAMP. The animals used to detect DC-STAMP expression in an organ or a tissue removed therefrom may be raised also under any conditions whereby the organ or tissue can express DC-STAMP in the absence of a test substance.

The effect of a test substance on DC-STAMP expression may be studied either by measuring the level of expression of the DC-STAMP gene or by measuring the level of expression of DC-STAMP which is the translation product of the DC-STAMP gene. A test substance capable of suppressing the expression of the DC-STAMP gene and/or DC-STAMP may be considered to be a substance having a therapeutic and/or preventive effect on metabolic bone disorders, preferably osteoporosis, rheumatoid arthritis and/or cancerous hypercalcemia.

Extraction of the total RNA from the cultured cells, measurement of the expression level of the DC-STAMP gene or measurement of the expression level of DC-STAMP may be carried out in accordance with a method described in the section of "2. Detection of metabolic bone disorders". In culturing mammalian cells, appropriate levels of RANKL and TNF-α may be added optionally to the medium with the test substance, or even without the substance in the case of a control culture.

(1) Methods Using the DC-STAMP Gene

This screening method includes methods using mammalian cultured cells and those using mammalian subjects, which will be described below, respectively.

(a) Methods Using Mammalian Cultured Cells (i) A method comprising the following steps of (i-1) to (i-3):

(i-1) extracting total RNA from a mammalian cell culture cultured in a medium containing a test substance;

(i-2) detecting a difference in expression level of the DC-STAMP gene between the total RNA in step (i-1) and total RNA from a mammalian cell culture cultured in the absence of the test substance; and (i-3) analyzing the difference in expression level of the gene described in step (i-2) to determine the effect of the test substance on treatment and/or prevention of a metabolic bone disorder.

(ii) A method comprising the following steps of (ii-1) to (ii-4):

(ii-1) extracting total RNA from a mammalian cell culture cultured in a medium containing a test substance;

(ii-2) extracting total RNA from a mammalian cell culture cultured in a medium free of the test substance;

(ii-3) measuring the expression level of the DC-STAMP gene in the total RNA in step ii-1) and in the total RNA in step ii-2), respectively; and (ii-4) analyzing a difference in expression level of the gene measured according to step (ii-3) between the total RNA in step (ii-1) and the total RNA in step (ii-2) to determine the effect of the test substance on treatment and/or prevention of a metabolic bone disorder.

(b) Methods Using Mammalian Subjects (i) A method comprising the following steps of (i-1) to (i-3):

(i-1) extracting a total RNA from a test sample taken from a mammalian subject to which a test substance has been administered;

(i-2) measuring a difference in the expression level of the DC-STAMP gene between the total RNA in step (i-1) and a total RNA from a test sample taken from a mammalian subject to which the test substance has not been administered; and (i-3) analyzing the difference in expression level of the gene described in step (i-2) to determine the effect of the test substance on treatment and/or prevention of a metabolic bone disorder.

(ii) A method comprising the following steps of (ii-1) to (ii-4):

(ii-1) extracting total RNA from a test sample taken from a mammalian subject to which the test substance has been administered;

(ii-2) extracting a total RNA from a test sample taken from a mammalian subject to which the test substance has not been administered;

(ii-3) measuring the expression level of the DC-STAMP gene in the total RNA in step (ii-1) and in the total RNA in step (ii-2), respectively; and (ii-4) analyzing the difference in the expression level of the gene described in step (ii-3) to determine the effect of the test substance on treatment and/or prevention of a metabolic bone disorder.

(2) Methods Using DC-STAMP

A screening method based on measurement of the expression level of DC-STAMP includes methods using mammalian cultured cells and those using animal subjects, which will include the steps below, respectively.

(a) Methods Using Mammalian Cultured Cells (i) A method comprising the following steps of (i-1) and (i-2):

(i-1) measuring the expression level of DC-STAMP in a mammalian cell culture cultured in a medium containing a test substance; and (i-2) analyzing a difference in expression level between the protein measured in step (i-1) and the protein in a mammalian cell culture cultured in a medium free of the test substance to determine the effect of the test substance on treatment and/or prevention of a metabolic bone disorder.

(ii) A method comprising the following steps of (ii-1) to (ii-3):

(ii-1) measuring the expression level of DC-STAMP protein in a mammalian cell culture cultured in a medium containing a test substance;

(ii-2) measuring the expression level of the protein according to step (ii-1) in a mammalian cell culture cultured in a medium free of the test substance; and (ii-3) detecting a difference in expression level between the protein measured in step (ii-1) and the protein measured in step (ii-2) to determine the effect of the test substance on treatment and/or prevention of a metabolic bone disorder.

(iii) A method comprising the following steps of (iii-1) to (iii-3):

(iii-1) immobilizing the total protein taken from a mammalian cell culture cultured in a medium containing a test substance;

(iii-2) measuring the expression level of DC-STAMP protein in the immobilized protein; and (iii-3) analyzing a difference in expression level between DC-STAMP detected in step (iii-2) and the protein in a total protein taken from a mammalian cell culture cultured in a medium free of the test substance to determine the effect of the test substance on treatment and/or prevention of a metabolic bone disorder.

(iv) A method comprising the following steps of (iv-1) to (iv-5):

(iv-1) immobilizing the total protein taken from a mammalian cell culture cultured in a medium containing a test substance;

(iv-2) immobilizing the total protein taken from a mammalian cell culture cultured in a medium free of the test substance;

(iv-3) measuring the expression level of DC-STAMP protein in the immobilized protein described in step (iv-1) using an antibody or a ligand capable of specifically binding to the protein;

(iv-4) measuring the expression level of DC-STAMP in the immobilized protein described in step (iv-2) using an antibody or a ligand capable of specifically binding to the protein;

(iv-5) analyzing a difference in expression level between the protein measured in step (iv-3) and the protein measured in step (iv-4) to determine the effect of the test substance on treatment and/or prevention of a metabolic bone disorder.

(b) Methods Using Mammalian Subjects (i) A method comprising the following steps of (i-1) and (i-2):

(i-1) measuring the expression level of DC-STAMP protein in a test sample taken from a mammalian subject to which a test substance has been administered; and (i-2) analyzing a difference in expression level between DC-STAMP measured in step (i-1) and the protein in a test sample taken from a mammalian subject to which the test substance has not been administered to determine the effect of the test substance on treatment and/or prevention of a metabolic bone disorder.

(ii) A method comprising the following steps of (ii-1) to (ii-3):

(ii-1) measuring the expression level of DC-STAMP protein in a test sample taken from a mammalian subject which a test substance has been administered, using an antibody or a ligand capable of specifically binding to the protein;

(ii-2) measuring the expression level of the protein in a test sample taken from a mammalian subject to which the test substance has not been administered; and (ii-3) analyzing a difference in expression level between DC-STAMP protein measured in step (ii-1) and the protein measured in step (ii-2) to determine the effect of the test substance on treatment and/or prevention of a metabolic bone disorder.

(iii) A method comprising the following steps of (iii-1) to (iii-3):

(iii-1) immobilizing the total protein in a test sample taken from a mammalian subject to which a test substance has been administered;

(iii-2) measuring the expression level of DC-STAMP protein in the immobilized protein; and (iii-3) analyzing a difference in expression level between DC-STAMP protein detected in step (iii-2) and the protein in a test sample taken from a mammalian subject to which the test substance has not been administered to determine the effect of the test substance on treatment and/or prevention of a metabolic bone disorder.

(iv) A method comprising the following steps of (iv-1) and (iv-5):

(iv-1) immobilizing the total protein in a test sample taken from a mammalian subject to which a test substance has been administered;

(iv-2) immobilizing the total protein in a test sample taken from a mammalian subject to which the test substance has not been administered;

(iv-3) detecting the expression level of DC-STAMP protein in the immobilized protein described in step (iv-1), using an antibody or a ligand capable of specifically binding to the protein;

(iv-4) detecting the expression level of DC-STAMP protein in the immobilized protein described in step (iv-2), using an antibody or a ligand capable of specifically binding to the protein; and (iv-5) analyzing a difference in expression level between the protein detected in step (iv-3) and the protein detected in step (iv-4) to determine the effect of the test substance on treatment and/or prevention of a metabolic bone disorder.

(3) Other Methods

A test substance can be given to animal subjects that over-express DC-STAMP to measure, over time, the incidence of metabolic bone disorder, severity thereof and/or survival rate etc. and to compare those with the counterparts for animals that over-express DC-STAMP but to which the test substance has not been given. If the animals that over-express DC-STAMP and have been given the test substance have a significantly lower incidence, a significantly lower severity and/or a survival rate that is higher by about 10%, preferably about 30% or more, and more preferably about 50% or more, the test substance may be selected as a compound effective to treat and/or prevent metabolic bone disorder.

6. Production of Anti-DC-STAMP Antibodies (1) Preparation of Antigens

An antigen for preparation of an anti-DC-STAMP antibody may be DC-STAMP or a polypeptide having a partial sequence of at least 6 contiguous amino acids thereof, or a derivative thereof further having any amino acid sequence or a carrier added thereto.

DC-STAMP used herein may be purified directly from blood cells or bone marrow cells, or may be in the form of a cell membrane fraction prepared therefrom. Also, the DC-STAMP may be synthesized in vitro or produced in host cells by genetic manipulation.

Prokaryotic hosts for this purpose include, for example, *Escherichia coli* and *Bacillus subtilis*. Transformation of the host cells with a target gene requires a plasmid vector containing a replicon i.e., a replication origin from a species compatible with the host, and a regulator element. The vector preferably has a sequence allowing the transformant to be selected by an expression trait (phenotype).

For instance, a K12 strain or the like is often used as an *E. coli* strain, and a pBR322 or pUC line is generally used as the vector. However, the bacterial strain and the vector used herein are not limited to these, but may include various known strains and vectors.

The promoter for *E. coli* used here may be tryptophan (trp) promoter, lactose (lac) promoter, tryptophan-lactose (tac) promoter, lipoprotein (lpp) promoter, polypeptide chain elongation factor Tu (tufb) promoter or the like, and any one of these may be used for production of the protein.

A preferred *B. subtilis* is, for example, the 207-25 strain, a vector that can be used therewith is pTUB228 (Ohmura, K. et al., (1984) J. Biochem. 95, 87-93) or the like. If a DNA encoding the signal peptide of an α-amylase from *B. subtilis* is linked to the vector, the protein may be excreted out of the cells.

Eukaryotic host cells include cells from vertebrate animals, insects, yeasts and so forth, and vertebrate cells often used include, for example, but are not limited to, murine monocyte-derived RAW264.7 cells (ATCC Cat. No. TIB-71), RAW264 cells (ECACC Cat. No. 85062803), and RAW-D cells (Watanabe et al., J. Endocrinol., (2004) 180, 193-201); dihydrofolate reductase-deficient strains (Urlaub, G. and Chasin, L. A., Proc. Natl. Acad. Sci. USA (1980) 77, 4126-4220) of simian COS cells (Gluzman, Y., Cell, (1981) 23, 175-182; ATCC CRL-1650), murine fibroblasts NIH3T3 (ATCC No. CRL-1658), and Chinese hamster ovarian cells (CHO cells; ATCC: CCL-61); and the like.

Expression promoters used for vertebrate animal cells generally have a promoter located upstream of the gene to be expressed, splice junctions for RNA, a polyadenylation site, a transcription termination sequence etc., and optionally a replication origin. Examples of the expression vector include, but are not limited to, pCDNA3.1 (from Invitrogen) having the cytomegalovirus early promoter, and pSV2dhfr having the SV40 early promoter (Subramani, S. et al., Mol. Cell. Biol., (1981) 1, 854-864).

Given COS or NIH3T3 cells as host cells, for example, the expression vector used herein will have the SV40 replication origin, the ability to self-replicate in the COS or NIH3T3 cells, and also a transcription promoter, a transcription termination signal and splice junctions for RNA. The expression vector may be incorporated into the COS or NIH3T3 cells by means of the diethylaminoethyl(DEAE)-dextran method (Luthman, H. and Magnusson, G., Nucleic Acids Res., (1983) 11, 1295-1308), phosphate calcium-DNA co-precipitation (Graham, F. L. and van der Eb, A. J., Virology, (1973) 52, 456-457), pulse electroporation (Neumann, E. et al., EMBO J., (1982) 1, 841-845) or the like to create desired transformed cells. If CHO cells are used as host cells, they may be co-transfected, together with the expression vector, with a vector which may express the neo gene to function as a G418 antibiotic-resistance marker, such as pRSVneo (Sambrook, J. et al. (1989): "Molecular Cloning A Laboratory Manual" Cold Spring Harbor Laboratory, NY) or pSV2neo (Southern, P. J. and Berg, P., J. Mol. Appl. Genet., (1982) 1, 327-341) and then screened to select G418 resistant colonies to obtain transformed cells capable of stably producing a desired polypeptide.

The resulting transformant may be cultured in accordance with a standard method to thereby produce the desired polypeptide within the cells, on the cell membrane, or excreted out of the cells. The medium used for the culture may be appropriately selected from different media commonly used for the host cells employed, and for example, in the case of COS cells, RPMI1640 medium or Dulbecco-modified Eagle medium (referred to as "DMEM" hereinafter) may be used, which optionally may be supplemented with a serum component such as fetal calf serum.

The recombinant protein produced within the transformant cells, on the cell membrane thereof, or excreted out of the cells can be isolated and purified by various known separation techniques which take advantage of the physical and/or chemical properties of the protein. Specifically, these techniques may include, for example, conventional protein treatment with a precipitant, ultrafiltration, different modes of chromatography, such as molecular sieve chromatography (gel filtration), adsorption chromatography, ion exchange chromatography, affinity chromatography and high performance chromatography (HPLC), dialysis and a combination thereof. Additionally, fusion of the expressed recombinant protein to 6 histidine residues enables efficient purification thereof on a nickel affinity column. A large amount of the desired polypeptide can be produced easily in a high yield and at a high purity by a combination of these techniques. If the protein is produced on the cell membrane, it can be separated and crudely purified by preparation of a cell membrane fraction.

(2) Production of Anti-DC-STAMP Monoclonal Antibodies

Antibody capable of specifically binding to DC-STAMP includes monoclonal antibodies capable of specifically binding to DC-STAMP, which are obtained as described below.

Production of a monoclonal antibody generally requires the following steps of:

(a) purification of a biopolymer for use as the antigen;

(b) immunization of an animal by injection of the antigen, subsequent sampling of the blood to assay its antibody titer and set the time of spleen removal, and preparation of antibody-forming cells;

(c) preparation of myeloma cells (hereinafter referred to as "myeloma"):

(d) cell fusion between the antibody-forming cells and the myeloma;

(e) screening a group of hybridomas producing the antibody of interest;

(f) division into a single cell clone;

(g) culture of the hybridoma or breeding of an animal implanted with the hybridoma, optionally, in order to scale-up production of a monoclonal antibody; and (h) examination of the monoclonal antibody thus produced for bioactivity and thus specificity, or testing thereof for properties as a labeled reagent and the like.

The method of preparing the monoclonal antibody will be described below in detail following the above steps, but it may comprise a modified version, not being limited to the description given. For instance, antibody-forming cells other than spleen cells may be used with myeloma.

(a) Purification of an Antigen

The antigen may be DC-STAMP prepared as described above, or a fragment thereof. It may be also a cell membrane fraction prepared from recombinant somatic cells expressing DC-STAMP or the recombinant somatic cells themselves expressing DC-STAMP, or a partial peptide of the protein of the invention chemically synthesized by a method well-known to those skilled in the art.

(b) Preparation of Antibody-Forming Cells

The antigen provided in step (a) is mixed with an adjuvant, such as Freund's complete or incomplete adjuvant, or potassium alum and then used as an immunogen to immunize an experimental animal. Any animal known to be used for creating a hybridoma suitably can be used as the experimental animal. Specifically, the animal may be mouse, rat, goat, sheep, cow, horse or the like. However, a mouse or rat is preferred as the animal for immunization for reasons such as the greater availability of myeloma cells to fuse with antibody-forming cells removed from such animals. The choice of mouse or rat line actually used is not particularly limited, mouse lines include A, AKR, BALBc, BDP, BA, CE, C3H, 57BL, C57BR, C57L, DBA, FL, HTH, HT1, LP, NZB, NZW, RF, R III, SJL, SWR, WB, and 129, whilst rat lines include Low, Lewis, Spraque, Daweley, ACI, BN and Fischer. These mice and rats are commercially available from breeders/distributors of experimental animals, for example, CLEA Japan, Inc., Charles River Laboratories Japan, Inc., Japan SLC, Inc., or The Jackson Laboratories. Particularly preferred lines of animal for immunization are the BALB/c mouse, or Low rat, taking in to consideration that they are suitable for fusion with myeloma cells, as described later. Also, mice having a lower biofunction to eliminate autoantibodies, that is, autoimmune disease-affected mice are preferable, taking account of antigenic homology between human and mouse. The mice or rats are preferably aged 5 to 12 weeks, more preferably 6 to 8 weeks, at the time of immunization.

The animal may be immunized with DC-STAMP or a recombinant version thereof by any known method described in detail, for example, in Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Spigfield, Ill. (1964); and so forth. A suitable method of immunization used in the present invention is exemplified below. First of all, a cell membrane fraction as antigen, or cells expressing the antigen, are given to the animal intradermally or intraperitoneally. However, preferably a higher level of immunity may be attained by a combination of both routes of dosing. Specifically, intradermal dosing in the early stage and intraperitoneal dosing in the late stage, or as the last dose only, are especially effective to attain a higher level of immunity. The schedule of antigen dosing may vary depending on the different animal species that are to be immunized, different individual animals and the like, but may be set preferably from 3 to 6 doses of antigen at a dose interval of 2 to 6 weeks, more preferably from 3 to 4 doses at a dose interval of 2 to 4 weeks. If the number of doses is too high, the antigen will be wasted, and if the dose interval is too long, the animal will be aged and have a lower cellular activity, neither of these situations is preferable. The dose level of antigen may vary depending on different animal species, different individual animals and the like, but may be generally from 0.05 to 5 ml, preferably about 0.1 to about 0.5 ml. A booster may be given 1 to 6 weeks after the above antigen dosing, preferably 2 to 4 weeks after, and more preferably 2 to 3 weeks after. If the booster is given after 6 weeks or before 1 week, its effect will be poor. The booster dose of antigen may vary depending on the different animal species, different body sizes and the like, but in mice, for example, it may be generally from 0.05 to 5 ml, preferably 0.1 to 0.5 ml, and more preferably about 0.1 to about 0.2 ml. An unnecessarily high dose will not only decrease the immune effect, but also be harmful to the immunized animal.

Spleen cells or lymphocytes including antibody-forming cells are removed aseptically from the immunized animal 1 to 10 days after the booster, preferably 2 to 5 days, and more preferably 2 to 3 days. At this point, if samples from selected animal subjects are assayed for antibody titer to select an individual animal with a suitably enhanced antibody titer as the supplier of the antibody-forming cells, the subsequent procedure can be carried out more efficiently.

The method of assaying antibody titers used here includes various known techniques such as RIA, ELISA, fluorescent antibody and passive hemagglutination techniques. The RIA or ELISA techniques are more preferable in terms of detection sensitivity, rapidness, accuracy, potentiality of automated operations and the like.

The assay of antibody titers according to the present invention, for example, by ELISA, may be conducted under a procedure as described below. Firstly, a pure or partially pure antigen is adsorbed to a solid surface, such as a 96-well plate for ELISA; the remaining exposed portion of the solid surface is then blocked with a protein, for example, bovine serum albumin (hereinafter referred to as "BSA"), which is unrelated to the antigen; the solid surface is rinsed; and it is contacted with serially-diluted samples of a first antibody (for example, murine serum) to bind the monoclonal antibody in the samples to the antigen. Secondly, an enzyme-labeled antibody as a second antibody against the above-mentioned murine antibody is added to bind to the murine antibody; the solid surface is rinsed; a substrate for the enzyme is added to produce a colour change due to decomposition of the substrate; a change in optical density caused by the colour change is determined; and the antibody titer is calculated from the change in optical density.

Isolation of the antibody-forming cells from the spleen cells or lymphocytes may be carried out according to a known method (for example, Kohler et al., Nature, (1975) 256, 495; Kohler et al., Eur. J. Immunol., (1977) 6, 511; Milstein et al., Nature, (1977) 266, 550; Walsh, Nature, (1977) 266, 495). For instance, as for spleen cells, a general method may be employed where the cells are disrupted, filtered through a stainless mesh and suspended in Eagle's minimum essential medium (MEM) to isolate the antibody-forming cells.

(c) Preparation of Myeloma Cells (Hereinafter Referred to as "Myeloma")

The choice of myeloma cells for use in cell fusion is not particularly limited, but may be selected appropriately from among the known cell strains. However, for convenience in selection of the hybridoma from fused cells, it is preferable to use a HGPRT (Hypoxanthine-guanine phosphoribosyl transferase)-deficient strain for which a selection process is established. HGPRT-deficient strains include X63-Ag8(X63), NS1-Ag4/1(NS1), P3×63-Ag8.U1(P3U1), X63-Ag8.653 (X63.653), SP2/0-Ag14(SP2/0), MPC11-45.6TG1.7 (45.6TG), FO, S149/5XXO, BU.1 derived from mice;

210.RSY3.Ag.1.2.3(Y3) derived from rats; and U266AR (SKO-007), GM1500.GTG-A12(GM1500), UC729-6, LICR-LOW-HMy2(HMy2) and 8226AR/NIP4-1(NP41) derived from humans. These strains can be obtained, for example, from the American Type Culture Collection (ATCC) and the like.

The cell strain is subcultured in a suitable medium, for example, a 8-azaguanine medium (a medium prepared by adding glutamine, 2-mercaptoethanol, gentamicin and fetal calf serum, hereinafter referred to as "FCS", into RPMI-1640 medium to prepare an intermediate medium, into which 8-azaguanine is then added), Iscove's modified Dulbecco's medium (hereinafter referred to as "IMDM") or Dulbecco's modified Eagle medium (hereinafter referred to as "DMEM"), and then subcultured in a normal medium (for example, ASF104 medium containing 10% FCS from Ajinomoto Co., Inc.) for 3 to 4 days before cell fusion, so as to obtain a cell count of at least $2 \times 10^7$ on the day of cell fusion.

(d) Cell Fusion

The fusion between the antibody-forming cells and the myeloma cells may be carried out under such conditions as will keep the cells above an extremely low survival rate, according to a known method (Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Spigfield, Ill. (1964); and others). Such methods include, for example, a chemical method of fusion by mixing the antibody-forming cells and the myeloma cells in a highly concentrated solution of a polymer, such as polyethylene glycol, and a physical method of fusion by means of electric stimulation. A specific example of the chemical method is described below. If a polyethylene glycol is used in the highly concentrated polymer solution, it may have a molecular weight of 1,500-6,000, preferably 2,000-4,000. In a solution of this polymer, the antibody-forming cells and the myeloma cells may be mixed at a temperature of 30 to 40° C., preferably 35 to 38° C., for 1 to 10 minutes, preferably 5 to 8 minutes.

(e) Selection of a Group of Hybridomas

Methods of selecting hybridomas produced by the cell fusion are not particularly limited, but HAT (hypoxanthine-aminopterin-thymidine) selection (Kohler et al., Nature, 256, 495 (1975); Milstein et al., Nature 266, 550 (1977)) is typically used. This method is effective to obtain hybridomas from a HGPRT-deficient strain of myeloma cells incapable of surviving in the presence of aminopterin. Thus, the non-fused cells and the hybridomas are cultured in HAT medium to allow only the hybridomas resistant to aminopterin to survive and grow selectively.

(f) Division into a Single Cell Clone (Cloning)

Methods of cloning a hybridoma include known methods, such as the methylcellulose technique, soft agarose technique and limiting dilution (see, for example, Barbara, B. M. and Stanley, M. S.: Selected Methods in Cellular Immunology, W.H. Freeman and Company, San Francisco (1980)). The cloning method includes limiting dilution, where a dilution made to contain a single hybridoma cell in a well of a multi-well plate is cultured; the soft agar technique where the cells are cultured in a soft agar medium to harvest the resulting colonies; a technique where single cells are removed individually using a micromanipulator and then each is cultured; and "sorter cloning" where single cells are separated out using a cell sorter. Of these techniques, limiting dilution is particularly suitable. In this technique, a feeder is first seeded on the microplate, the feeder may be a rat fetus-derived fibroblast strain, or spleen cells, thymus cells or ascites cells, all from normal mice. A dilution of the hybridoma cells at 0.2 to 0.5 cells/0.2 ml of the medium is prepared in advance. This dilution of the suspended hybridoma cells is placed in each well at 0.1 ml/well, and cultured for about two weeks, while about one third of the volume of the medium is replaced with fresh medium after particular intervals of time (for example, every three days), to permit growth of the hybridoma clone.

In wells in which there is a detectable antibody titer, the hybridoma is cloned repeatedly two to four times, for example, by limiting dilution, and if the hybridoma in a well has a stable, detectable antibody titer, it is selected as a hybridoma strain capable of producing an anti-DC-STAMP monoclonal antibody.

(g) Culture of the Hybridoma to Prepare a Monoclonal Antibody

The hybridoma thus selected may be cultured to provide a monoclonal antibody efficiently. However, it is desirable to screen the hybridoma for production of the monoclonal antibody of interest prior to culture. The screening may be conducted by a known method of screening.

The assay of antibody titers according to the present invention, for example, by ELISA, may be conducted under a procedure as described below. Firstly, pure or partially pure DC-STAMP, or DC-STAMP-expressing cells are adsorbed to a solid surface, such as a 96-well plate for ELISA; the remaining exposed portion of the solid surface is then blocked with a protein, for example, bovine serum albumin (hereinafter referred to as "BSA"), which is not related to the antigen; the solid surface is rinsed; and it is contacted with serially-diluted samples of a first antibody (for example, a supernatant of the hybridoma culture) to bind the anti-DC-STAMP antibody in the samples to the antigen. Secondly, an enzyme-labeled antibody, as a second antibody against the murine antibody, is added to bind to the murine antibody; the solid surface is rinsed; a substrate for the enzyme is added to produce a colour change due to decomposition of the substrate; the change in optical density caused by the colour change is determined; and the antibody titer is calculated from the change in optical density. This screening may be conducted after or before the above-described cloning of the hybridoma.

The hybridoma obtained following the above procedure may be stored in a frozen state in liquid nitrogen or in a deep freezer at a temperature below −80° C.

The cloned hybridoma is transferred from HT medium to a normal medium for culture. It is cultured on a large scale by rotary culture in a large culture bottle or by spinner culture. The supernatant of the large scale culture is subjected to a purification treatment known to those skilled in the art, such as gel filtration, to obtain monoclonal antibody capable of specifically-binding to the protein of the invention. In addition, the hybridoma may be injected into the peritoneum of the same line of mice (for example, BALB/c as described above) or of Nu/Nu mice and grown there to produce an ascites containing a large amount of the monoclonal antibody of the invention. A mineral oil such as 2, 6, 10, 14-tetramethylpentadecane (pristane) may be given 3 to 7 days before the intraperitoneal injection to produce a larger amount of ascites. An immunosuppressor, for example, may be injected in advance into the peritoneum of the same line of mice as the hybridoma to inactivate the T cells, and 20 days later a suspension of $10^6$-$10^7$ cells of the cloned hybridoma in a serum-free medium (0.5 ml) may be administered into the peritoneum to allow the abdomen typically to swell and accumulate ascites and the ascites can be removed from the mouse. This process can provide the monoclonal antibody in a concentration about 10 times higher than that achieved in culture.

The monoclonal antibody provided by any one of the methods described above may be purified, for example, according to the methods described in Weir, D. M.: Handbook of Experimental Immunology Vol. I, II, III, Blackwell Scientific Publications, Oxford (1978). The methods include salting-out using ammonium sulfate, gel filtration, ion-exchange chromatography and affinity chromatography. One of the methods, salting-out using ammonium sulfate may be repeated 3 to 4 times, preferably 3 to 6 times to purify the monoclonal antibody. However, this method provides a very low yield of the purified monoclonal antibody. Therefore, the monoclonal antibody may be first purified crudely by salting-out using ammonium sulfate once or twice and further treated by at least one method, preferably two methods, selected from gel filtration, ion-exchange chromatography, affinity chromatography, etc., to provide the monoclonal antibody at a high purity in a high yield. A combination of salting-out using ammonium sulfate with another method and their order may be illustrated by: (i) salting-out using ammonium sulfate-ion exchange chromatography-gel filtration, (ii) salting-out using ammonium sulfate-ion exchange chromatography-affinity chromatography, (iii) salting-out using ammonium sulfate-gel filtration-affinity chromatography, and the like, but the combination (iii) is most preferable to provide monoclonal antibody at a high purity in a high yield.

To readily purify the monoclonal antibody, a commercial monoclonal antibody purification kit (for example, MabTrap GII kit from Amersham Pharmacia Biotech) is also available.

The resulting monoclonal antibody has a high antigen specificity for DC-STAMP.

(h) Assay of the Monoclonal Antibody

The isotype and subclass of the resultant monoclonal antibody can be determined as described below. These may be identified by the Ouchterlony, ELISA or RIA techniques. The Ouchterlony technique is simple, but if the monoclonal antibody sample is at a low concentration, it must be concentrated for the assay. On the other hand, in the ELISA or RIA technique, the supernatant of the untreated culture may be reacted with an antigen-adsorbed solid phase, which may then be treated with a secondary antibody corresponding to an individual isotype or subclass of immunoglobulin to identify the isotype and subclass of the monoclonal antibody. A simpler assay can also be conducted using a commercial identification kit (for example, Mouse Typer kit from Bio-Rad Laboratories Inc.).

Further, the antibody protein may be quantitated by Folin-Lowry assay or by calculation from the optical density at 280 nm (1.4 of $OD_{280}$ is equivalent to immunoglobulin at 1 mg/ml).

(3) Creation of a Humanized Anti-DC-STAMP Antibody

Immunoglobulin G (simply referred to as "IgG" hereinafter) is composed of two light polypeptide chains (hereinafter referred to as "light chain") with a molecular weight of about 23,000 and two heavy polypeptide chains (hereinafter referred to as "heavy chain") with a molecular weight of about 50,000. Both heavy chains and light chains have a structure consisting of repeating domains having an amino acid sequence of about 110 conserved residues, where the domains are basic units (hereinafter referred to as "domain") forming a three-dimensional IgG structure. The heavy and light chains are composed of four and two contiguous domains, respectively. In both heavy and light chains, the amino terminal domain has an amino acid sequence which is more variable among different antibody molecules than that in the other domains, and therefore it is called the variable domain (hereinafter referred to as "V domain"). In the amino terminal of IgG, both V domains of the heavy and light chains are associated complementarily to form a variable region. The other domains form the constant region as a whole. The constant region has a sequence characteristic of an individual animal species. For instance, the constant region of murine IgG is different from that of human IgG and thus murine IgG is recognized as foreign by the human immune system which induces a human anti-mouse antibody response (hereinafter referred to as "HAMA") (Schloff et al., Cancer Res., (1985) 45, 879-85). Consequently, a murine antibody can not be given again to that human. To administer such antibody into a human, it must be modified so as not to induce the HAMA response whilst maintaining the antibody specificity.

The results of X-ray crystallographic analysis reveal that such a domain generally takes an elongated cylindrical structure having bilayered anti-parallel β-sheets each composed of three to five β-chains. In the variable region, the V domains of the heavy and light chains have three loops clustered, respectively, to form an antigen-binding site. Each loop is called a complementarity-determining region (hereinafter referred to as "CDR") which is the most variable region in the amino acid sequence. The portion of the variable region outside the CDRs generally serves to maintain the structure of the CDRs and is thus called the "framework". Kabatt et al. collected a large amount of data on the primary sequences in the variable region of heavy and light chains, and made a list to divide the respective primary sequences into CDR and framework, based on how they are conserved (Sequences Of Immunological Interest, 5th edition, NIH publication, No. 91-3242, E. A. Kabatt et al.). The frameworks were also divided into subgroups which have common amino acid sequence characteristics, respectively. Furthermore, corresponding frameworks were identified between humans and mice.

Some methods of creating a humanized antibody have been devised as described below, based on these studies on the structural characteristics of IgG.

In an early stage of the study, a chimeric antibody was proposed in which a variable region from a murine antibody was linked to a constant region from a human antibody (see Proc. Natl. Acad. Sci. U.S.A. 81, 6851-6855, (1984)). However, such chimeric antibody still has many non-human amino acid residues, and thus the HAMA response may be induced if the antibody is administered to a human for a long period of time (Begent et al., Br. J. Cancer, (1990) 62, 487).

In order to further decrease the number of non-human mammalian amino acid residues which may induce the HAMA response, a method to integrate only the mammalian CDR portion into a human antibody was proposed (see Nature, 321, 522-525, (1986)), but generally, grafting of only CDRs has been found to be inadequate to maintain the activity of the immunoglobulin against the antigen.

In 1987, Chothia et al. found, from the data of X-ray crystallographic analysis, that:

(a) the amino acid sequence of a CDR comprises a site for its direct binding to the antigen and a site for maintenance of the CDR structure, and possible three-dimensional structures taken by CDR are classified into a plurality of typical patterns (canonical structures); and (b) the class of a canonical structure is determined by the CDR itself, as well as by the type of amino acid located at a specific position in the framework portion (J. Mol. Biol., (1987) 196, 901-917).

Based on the findings, it was suggested that CDR grafting into a human antibody may require the CDR sequence and the amino acid residues from the framework (see National Publication of International Patent Application No. 1992-502408).

Generally, a non-human mammalian antibody having CDRs to be grafted is defined as a "donor", while a human antibody which is to be grafted with the CDRs is defined as an "acceptor", and these definitions will be also used here.

In carrying out CDR grafting, the structure of CDR must be conserved as much as possible to maintain the activity of the immunoglobulin molecules. To attain this purpose, the following two points must be considered:

(a) which subgroup does the acceptor to be selected belong to, and, (b) which amino acid residue should be removed from the framework of the donor?

Queen et al., presented a design procedure whereby an amino acid residue in the framework of the donor should be grafted into the acceptor together with the CDR sequences if the amino acid residue satisfies at least one of the following criteria (see National Publication of International Patent Application No. 1992-502408):

(a) an amino acid in the framework of the acceptor is rarely seen at the position, and the corresponding amino acid in the donor is commonly seen at the same position in the acceptor;

(b) the amino acid is very close to one of the CDRs;

(c) the amino acid is expected to have a side-chain atom about 3 Å or less away from the CDR in the three-dimensional immunoglobulin model and is expected to be capable of interacting with the antigen or CDR in the humanized antibody to be created.

The DNA encoding the heavy chain or light chain of the anti-DC-STAMP monoclonal antibody according to the present invention may be obtained by preparing mRNA from the hybridoma cells producing the anti-DC-STAMP monoclonal antibody, converting the mRNA to cDNA with a reverse transcriptase, and isolating the DNA encoding the heavy chain or light chain of the antibody.

The mRNA may be extracted by guanidine thiocyanate-hot phenol, guanidine thiocyanate-guanidine hydrochloride or the like, but preferably guanidine thiocyanate-cesium chloride. The mRNA from the cells may be prepared either by first preparing total RNA, and then purifying it from the total RNA using a carrier for poly(A)$^+$RNA purification, such as oligo (dT) cellulose or oligo(dT) latex beads, or by purifying it directly from the cell lysate using the carrier. The total RNA may be prepared by techniques such as alkaline sucrose density-gradient centrifugation (Dougherty, W. G. and Hiebert, E., Virology, (1980) 101, 466-474), guanidine thiocyanate-phenol, guanidine thiocyanate-cesium trifluoride, and phenol-SDS, but preferably by the technique using guanidine thiocyanate and cesium chloride (Chirgwin, J. M. et al., Biochemistry (1979) 18, 5294-5299).

Using the resultant poly(A)$^+$RNA as template, a single strand cDNA may be synthesized by enzymatic reverse transcription, and then a double strand cDNA may be synthesized from the single strand cDNA. The method of synthesizing the double strand cDNA may include a S I nuclease process (Efstratiadis, A., et al., Cell, (1976) 7, 279-288), Gubler-Hoffman process (Gubler, U. and Hoffman, B. J., Gene, (1983) 25, 263-269), and Okayama-Berg process (Okayama, H. and Berg, P., Mol. Cell. Biol., (1982) 2, 161-170), but preferably in the present invention, the polymerase chain reaction is used (hereinafter referred to as "PCR") using single-stranded cDNA as template, the so-called RT-PCR process (Saiki, R. K., et al., Science, (1988) 239, 487-49).

The double strand cDNA thus produced may be integrated into a cloning vector to produce a recombinant vector, which may then be introduced into a microbe such as $E.$ $coli$ to transform it and the transformant can be selected using tetracycline resistance, ampicillin resistance or the like as a marker. $E.$ $coli$ may be transformed by the Hanahan process (Hanahan, D., J. Mol. Biol., (1983) 166, 557-580), that is, by addition of the recombinant DNA vector to competent cells, which are prepared from $E.$ $coli$ in the presence of calcium chloride, magnesium chloride or rubidium chloride. If the plasmid is a vector, it is necessary for it to have a drug-resistance gene. In addition, cloning vectors other than plasmids, for example, λ phage or the like, may be used.

The different methods as described below may be employed, for example, to select a strain having cDNA encoding each subunit of the anti-DC-STAMP monoclonal antibody of interest from the transformant obtained as described above. If the cDNA of interest has been specifically amplified by the above RT-PCR process, that procedure of the method may be omitted.

(3-1) The Method Using the Polymerase Chain Reaction

If the entire amino acid sequence of the protein of interest or a part thereof is known, oligonucleotide primers having a sense strand and an anti-sense strand, respectively, corresponding to a part of the amino acid sequence, may be synthesized, and then used together for carrying out the polymerase chain reaction (Saiki, R. K., et al., Science, (1988) 239, 487-49) to amplify a DNA fragment encoding the subunit of the heavy or light chain of the anti-DC-STAMP antibody of interest. The template DNA used here may be, for example, cDNA synthesized by enzymatic reverse transcription from the mRNA of a hybridoma which produces the anti-DC-STAMP monoclonal antibody.

The resultant DNA fragment may be integrated directly into a plasmid vector using a commercially available kit or the like, or it may be labeled with $^{32}$P, $^{35}$S, or biotin or the like, and used as probe in colony hybridization or plaque hybridization to select a target clone.

The partial amino acid sequence of each subunit in the anti-DC-STAMP monoclonal antibody according to the present invention may be examined by isolating the subunit by a known method such as electrophoresis or column chromatography, and analyzing the N-terminal amino acid sequence of the subunit with an automatic protein sequencer (for example, PPSQ-10 made by Shimadzu Corporation) or the like.

A cDNA encoding each subunit in the anti-DC-STAMP monoclonal antibody protein from the transformant strain of interest thus obtained may be harvested according to a known process (Maniatis, T., et al. (1982) in "Molecular Cloning A Laboratory Manual" Cold Spring Harbor Laboratory, N.Y.). The process may be carried out, for example, by separating a fraction corresponding to the vector DNA from the cells, and cutting out the DNA region encoding the subunit of interest from the plasmid DNA.

(3-2) Screening Method Using Synthetic Oligonucleotide Probes

If the entire amino acid sequence of the protein of interest or a part thereof is known (the partial sequence may be for any region of the protein if it is a specific sequence having multiple contiguous amino acids), an oligonucleotide corresponding to the amino acid sequence may be synthesized (the oligonucleotide may have a nucleotide sequence predicted by referring to the frequency of codon usage, or include multiple nucleotide sequences composed of various possible nucleotide sequences in combination, in the latter case, fewer nucleotide sequences are needed if inosine is incorporated), and hybridized as a probe (labeled with $^{32}$P, $^{35}$S, or biotin or the like) to a nitrocellulose filter onto which the DNA of the transformant strain has been immobilized via denaturation to screen the resulting positive strains.

The sequence of the DNA thus obtained may be determined, for example, by Maxam-Gilbert chemical modification (Maxam, A. M. and Gilbert, W., Methods in Enzymology, (1980) 65, 499-576), dideoxynucleotide chain termination (Messing, J. and Vieira, J., Gene (1982)19, 269-276) or the like.

Recently, automated nucleotide sequence determination systems using fluorescent dyes have been also used widely (for example, the Sequence Robot "CATALYST 800" and Model 373A DNA sequencer, both made by Perkin Elmer Japan Co., Ltd.)

The DNA nucleotide sequence can be determined in an efficient, safe procedure by using such a system. The nucleotide sequence of a DNA according to the present invention, which is determined as described above, and the data concerning the N-terminal amino acid sequences of the heavy and light chains may be used to determine the entire amino acid sequence of the heavy and light chains in a monoclonal antibody of the invention.

The heavy chain and light chain of immunoglobulin both consist of a variable region and a constant region, and the variable region further consists of complementarity determining regions (hereinafter referred to as "CDR", three regions each for the heavy and light chains) and framework regions (four regions each for the heavy and light chains) adjacent thereto.

Of these regions, the constant region has an amino acid sequence independent of the antigen type and common to antibodies belonging to the same subclass of immunoglobulin. In contrast, the variable region, especially at the CDRs, has an amino acid sequence unique to each type of antigen, but comparative study of the data on amino acid sequences of many different antibodies has revealed that both the position of the CDRs and the sequence length of the framework are very similar in the subunits of different antibodies that belong to the same subgroup (Kabat, E. A. et al., in "Sequence of Proteins of Immunological Interest Vol. II": U.S. Department of Health and Human Services, (1991)). Therefore, if the respective amino acid sequences of the heavy and light chains, for example, in the anti-DC-STAMP monoclonal antibody, are compared with the data for known corresponding amino acid sequences, the CDRs and frameworks as well as the constant region in the respective amino acid sequences can be located. In this context, $FRH_1$, the framework region closest to the N-terminus of the heavy chain, is known to have a sequence length which may be shorter than the common length (30 amino acids), for example, it may be as little as 18 amino acids (Kabat et al. described above). Accordingly, in the antibody of the present invention, so long as the function as an anti-DC-STAMP antibodies is retained, the framework region closest to the N-terminus of the heavy chain may have a sequence length from 18 amino acids to 30 amino acids, preferably of 30 amino acids.

In addition, a peptide having the same amino acid sequence as the CDR in the heavy or light chain, which is determined as described above, or having a partial amino acid sequence thereof with contiguous amino acids may be modified artificially so as to substantially adopt a conformation which the CDR forms in the anti-DC-STAMP antibody molecule to provide a single peptide with the ability to bind DC-STAMP (see, e.g., U.S. Pat. No. 5,331,573). Thus, such a modified peptide having the same amino acid sequence as a CDR or having a partial amino acid sequence thereof with contiguous amino acids is included in the molecules of the present invention.

In order to create a variant having an amino acid sequence with a deletion of one or more amino acids therein, cassette mutagenesis (Kishimoto Toshimitsu, Ed., New Experimental Biochemistry Lecture Series No. 2, Nucleic Acids III: Recombinant DNA Technology, 242-251) or the like may be used.

These various DNAs may be also produced by chemical synthesis of nucleic acids in accordance with a standard method, for example, phosphite triester process (Hunkapiller, M. et al., Nature (1984) 310, 105-111) or the like. Codons themselves for a desired amino acid are known and may be selected arbitrarily. They may be selected conventionally, for example, taking account of their frequency used in the host. Such codons in the nucleotide sequence may be partially modified in a usual manner by site-specific mutagenesis (Mark, D. F. et al., Proc. Natl. Acad. Sci. USA (1984) 81, 5662-5666) or the like, where synthetic oligonucleotides encoding a desired modification are used as primer.

The ability of a DNA to hybridize with DNA encoding the heavy chain or light chain of the anti-DC-STAMP monoclonal antibody of the invention, or not, may be examined using a probe DNA labeled with [$\alpha$-$^{32}$P]dCTP or the like, for example, according to the random primer technique (Feinberg, A. P. and Vogelstein, B., Anal. Biochem. (1983) 132, 6-13), nick translation (Maniatis, T. et al., in "Molecular Cloning A Laboratory Manual" Cold Spring Harbor Laboratory, NY. (1982)) or the like. The experimental procedure will be followed as described below.

The DNA to be examined is adsorbed, for example, to a nitrocellulose or nylon membrane or the like, optionally denatured with alkali or the like, and immobilized by heat, UV light or the like. The membrane is immersed in a pre-hybridization solution containing 6×SSC (1×SSC contains 0.15M sodium chloride and 0.015M trisodium citrate), 5% Denhart solution and 0.1% sodium dodecyl sulfate (SDS), and kept at 55° C. for at least 4 hours, and the probe prepared as described above is added to the pre-hybridization solution so that the final specific activity is $1 \times 10^6$ cpm/ml, the membrane is incubated at 60° C. overnight. Thereafter, the membrane is washed with 6×SSC at ambient temperature for 5 minutes several times, and further with 2×SSC for 20 minutes, and subjected to autoradiography.

In this way, a DNA capable of hybridizing with the DNA encoding the heavy chain or light chain of the humanized anti-DC-STAMP antibody of the invention can be isolated from any cDNA library or genome library (Maniatis, T. et al., in "Molecular Cloning A Laboratory Manual" Cold Spring Harbor Laboratory, NY., (1982)).

Each of the DNAs thus obtained may be integrated into an expression vector, and the expression vector may be then introduced into prokaryotic or eukaryotic host cells to express the gene of interest in the host cells. The expression of the gene may be attained by a method described in "(1) Preparation of antigens" in "6. Production of anti-DC-STAMP antibodies".

A fraction containing the anti-DC-STAMP antibody protein produced within or exported out of the transformant cells may be separated and purified by various known methods of protein separation which take advantage of the physical and/or chemical properties of the protein or the like. These methods may be exemplified specifically by ordinary treatment with a protein precipitant, ultrafiltration, various modes of chromatography such as molecular sieve chromatography (gel filtration), adsorption chromatography, ion-exchange chromatography, affinity chromatography and high performance liquid chromatography (HPLC), dialysis and a combination thereof.

In order to humanize an anti-DC-STAMP monoclonal antibody, the amino acid sequence of the variable region to be humanized must be designed so that the predetermined entire CDR sequence and amino acid residues forming a part of the FR sequence may be grafted into the human antibody. The design can follow any of the methods described below.

In conventional design for humanization, the guiding principles of selection of subgroups for the acceptor is to select:

(a) use of the native combinations in the heavy and light chains of a known human antibody having a native amino acid sequence; or (b) use of heavy and light chains which are derived from different human antibodies, while the heavy and light chains conserve the respective combinations in the subgroups they belong to, and have high amino acid sequence identities to those of the heavy and light chains in the donor, or of heavy and light chains having consensus sequences. In the present invention, the above guiding principles may be followed, but a different approach may be employed comprising:

(c) selecting FRs in heavy and light chains having the highest identities to the FRs in the donor from the library of primary sequences in a human antibody, without consideration of combinations in the subgroups they belong to. This approach to selection allows the donor and acceptor to have at least 70% amino acid identity in the FR portions. In this way, fewer amino acid residues from the donor may be grafted and the HAMA response may be thereby induced to a lesser degree.

The three-dimensional structure of an antibody molecule can be predicted with a limited accuracy from its primary sequence (thereafter, such prediction is referred to as "molecular modelling"). This prediction can not identify well the role of amino acid residues occurring only rarely in the subgroup to which the donor belongs. It is generally difficult to determine, according to the method by Queen et al., which of the amino acid residues in the donor and the acceptor should be selected for these positions. Using selection approach (c), the need to make such determinations may be avoided.

The present inventors provide a novel method of identifying amino acids derived from FR in the donor which play an important role in maintenance of the structure and function of CDR in the donor, and have further improved the method of antibody humanization.

Once human acceptor molecular species have been selected for the light and heavy chains, respectively, amino acid residues to be grafted from the FR in the donor may be selected as described below.

When the amino acid sequences of the donor and the acceptor are aligned and different amino acid residues are present in the corresponding positions of the FR in the donor and the acceptor, it is necessary to determine which amino acid residues should be selected for these positions. In this selection, it is necessary not to vary the three-dimensional structure of the CDR derived from the donor.

Queen et al., suggested in National Publication of International Patent Application No. 1992-502408 that an amino acid residue in the FR should be grafted into the acceptor together with the CDR sequences if the amino acid residue satisfies at least one of the following requirements:

1) an amino acid in the human FR region of the acceptor is rarely seen at the position, and the corresponding amino acid in the donor is commonly seen at the same position in the acceptor;

2) the amino acid is very close to one of the CDRs;

3) the amino acid is expected to have a side-chain atom about 3 Å or less away from CDR in the three-dimensional immunoglobulin model and to be capable of interacting with the antigen or CDR in the humanized antibody to be created.

Since the residue described in 2) frequently shows the property described in 3), the requirement 2) is omitted in the present invention, but two additional requirements are set. Thus, in the present invention, an amino acid residue in the FR of the donor to be grafted together with the CDR sequences should satisfy at least one of the following requirements:

a) an amino acid in the FR of the acceptor is rarely seen at the position, and the corresponding amino acid in the donor is commonly seen at the same position;

b) the amino acid is expected to interact with a constituent atom of an amino acid of the CDR in the three-dimensional structure model and also with the antigen or the CDR loop to be grafted;

c) the position is occupied by a residue that determines the canonical class; or d) the position is on the contact surface between the heavy and light chains.

In requirement a), an amino acid found at a frequency of 90% or more at the position in antibodies of the same subclass is defined as "common", and an amino acid found at a frequency of less than 10% is defined as "rare", according to the table by Kabat as described above.

In the requirement c), whether or not "the position is occupied by a residue that determines the canonical class" may be determined unambiguously according to the table by Chothia as described above.

To check the requirements b) and d), it is necessary to perform molecular modelling in advance for the variable region of the antibody. Any commercial software for molecular modelling may be used in this case, but preferably AbM is used (Oxford Molecular Limited).

In the present invention, the accuracy of structural prediction provided by molecular modelling is determined with reference to experimental results of X-ray crystallographic analysis on the variable regions of various antibodies, since the accuracy of prediction by molecular modelling is limited within a certain range.

In the present invention, if the diatomic distance in the three-dimensional structure of the variable region, which has been constructed by molecular modelling software such as AbM, is shorter than the sum of the van der Waals radius of each of the two atoms plus 0.5 Å, the atoms are assumed to be in contact with each other by van der Waals forces. If the diatomic distance between two polar atoms in the main and side chains such as amide nitrogen, carbonyl oxygen, and the like, is shorter than 2.9 Å, i.e., the average hydrogen bond distance, plus 0.5 Å, they are assumed to have a hydrogen bond between them. Further, if the diatomic distance between two oppositely charged atoms is shorter than 2.85 Å plus 0.5 Å, an ion pair is assumed to be formed between them.

On the other hand, experimental results of X-ray crystallographic structural analysis on the variable regions of various antibodies demonstrate that the positions in the FR which are seen to be in contact with CDR with a high frequency, independently of the subgroup involved, are Nos. 1, 2, 3, 4, 5, 23, 35, 36, 46, 48, 49, 58, 69, 71 and 88 in the light chain, and Nos. 2, 4, 27, 28, 29, 30, 36, 38, 46, 47, 48, 49, 66, 67, 69, 71, 73, 78, 92, 93, 94 and 103 in the heavy chain (the figures represent numbers locating respective amino acids as defined in the publication by Kabat et al., and such figures will be used hereinafter). If the same standards as used in molecular modelling are applied to these positions, amino acid residues at these positions are recognized to be in contact with amino acid residues in CDR in two thirds of known antibody variable regions. On these findings, the requirement b) "the amino acid is expected to interact with a constituent atom of an amino acid of the CDR in the three-dimensional structure model and also with the antigen or the CDR loop to be grafted" means the following requirement.

If the position of the FR at which the FR is predicted to come into contact with the CDR in molecular modelling coincides with any one of the positions at which the FR is observed to be in contact with the CDR with a high frequency in experimental X-ray crystallographic analysis, the amino acid residue at the position of the donor should be grafted preferentially. In other cases, the requirement b) is not considered.

The requirement d) "the position is on the contact surface between the heavy and light chains" means the following requirement. Experimental results of X-ray crystallographic analysis of the variable regions of various antibodies demonstrate that amino acid residues at positions 36, 38, 43, 44, 46, 49, 87 and 98 in the light chain, and amino acid residues at positions 37, 39, 45, 47, 91, 103 and 104 in the heavy chain make contact between the heavy and light chains with a high frequency. If a position predicted to make contact between the heavy and light chains in molecular modelling coincides with any one of the positions described above, the amino acid residue at the position of the donor should be grafted preferentially. In other cases, the requirement d) is not considered.

A DNA encoding the variable regions of heavy and light chains in the humanized anti-DC-STAMP antibody according to the present invention can be produced by the methods described below.

For instance, multiple polynucleotide fragments constituting partial nucleotide sequences of the DNA and having a length of 60 to 70 nucleotides may be synthesized chemically so that they are aligned alternately on the sense and antisense sides, then each annealed and ligated using DNA ligase to produce a desired DNA comprising DNA encoding the variable regions of heavy and light chains in the humanized anti-DC-STAMP antibody.

Another method is also available in which a DNA encoding the total amino acid sequence of the variable region in the acceptor is isolated from human lymphocytes, and a region encoding the CDR is substituted with nucleotides by a method well known to those skilled in the art to incorporate restriction site sequences. Then, the region is cleaved with appropriate restriction enzymes, a nucleotide sequence encoding the CDR in the donor is synthesized, and it is ligated using DNA ligase to produce a desired DNA encoding the variable regions of heavy and light chains in the humanized anti-DC-STAMP antibody.

Furthermore, in the present invention, the overlap extension PCR method (see Holton et al., Gene, 77, 61-68 (1989)) described below may preferably be used to produce a desired DNA encoding the variable regions of heavy and light chains in the humanized anti-DC-STAMP antibody.

Specifically, two different DNAs encoding two different amino acid sequences intended to be connected with each other are called (A) and (B) for convenience. A sense primer (hereinafter referred to as (C)), of 20 to 40 nucleotides, to be annealed on the 5'-side of (A), and an antisense primer (hereinafter referred to as (D)), of 20 to 40 nucleotides, to be annealed on the 3'-side of (B), are synthesized chemically. In addition, 20 to 30 nucleotides on the 3'-side of (A) and 20 to 30 nucleotides on the 5'-side of (B) are ligated to synthesize a chimeric sense primer (hereinafter referred to as (E)) and an antisense primer complementary to that primer (hereinafter referred to as (F)). A suitable vector DNA containing (A) as the substrate is subjected to PCR using the sense primer (C) and the chimeric antisense primer (F) to produce a DNA containing (A) with the 20 to 30 5'-terminal nucleotides of (B) added to the 3'-terminus of (A) (the resulting DNA is referred to as (G)). Similarly, a suitable vector DNA containing (B) as the substrate is subjected to PCR using the antisense primer (D) and the chimeric sense primer (E) to produce a DNA containing (B) with the 20 to 30 3'-terminal nucleotides of (A) added to the 5'-terminus of (B) (the resulting DNA is referred to as (H)). In the resulting (G) and (H), the 40 to 60 3'-side nucleotides of (G) and the 40 to 60 5'-side nucleotides of (H) have complementary nucleotide sequences. When (G) and (H) are amplified, respectively, and then mixed to perform PCR, the first denaturation gives rise to a single strand of (G) and (H) in combination, and subsequent annealing recovers most of the starting DNA, but a portion of the DNA is annealed in the complementary nucleotide sequence regions to form a double-stranded hetero-DNA. Subsequent extension fills in the overhanging single-stranded portion to provide a chimeric DNA in which (A) and (B) are connected (the DNA is hereinafter referred to as (I)). Further, (I) as substrate is subjected to PCR using the sense primer (C) and the antisense primer (D) to amplify (I). In the present invention, the above-described ligation can be carried out by using a DNA encoding the CDR regions of heavy and light chains of an anti-human DC-STAMP murine monoclonal antibody, a DNA encoding FR regions of a human immunoglobulin IgG, and a DNA encoding the secretion signal for a human immunoglobulin IgG as (A) and (B) as the case may be.

Codons for a desired amino acid are known and may be selected arbitrarily. They may be selected conventionally, for example, taking account of their frequency of use in the host that is to be used. Such codons in the nucleotide sequence may be partially modified in a conventional manner by site-specific mutagenesis (Mark, D. F. et al., Proc. Natl. Acad. Sci. USA (1984) 81, 5662-5666) or the like, where synthetic oligonucleotides encoding a desired modification are used as the primer. Accordingly, in chemical synthesis of the primers, they may be designed in advance so as to introduce subsequently a point mutation to provide a desired DNA encoding the variable regions of heavy and light chains in the anti-DC-STAMP antibody.

Integration of any one of the DNAs of the invention thus obtained into an expression vector will allow transformation of prokaryotic or eukaryotic host cells. Further, introduction of a suitable promoter and a sequence for a selectable trait into the vector will allow the host cells to express the gene.

Recombinant anti-DC-STAMP antibodies may be produced without difficulty at a high yield and with high purity by the methods described above.

(4) Creation of Complete Human Anti-DC-STAMP Antibodies

A complete human antibody means a human antibody having gene sequences of an antibody derived solely from a human chromosome. A complete human anti-DC-STAMP antibody can be created by a method using human antibody-producing mice into which a human chromosome fragment containing genes for human antibody H and L chains has been transferred (Tomizuka, K. et al., Nature Genetics, (1977) 16, 133-143; Kuroiwa, Y. et al., Nuc. Acids Res., (1998) 6, 3447-3448; Yoshida, H et al., Animal Cell Technology: Basic and Applied Aspects, (1999) 10, 69-73 (Kitagawa, Y., Matuda, T. and Iijima, S. eds.), Kluwer Academic Publishers; Tomizuka, K. et al., Proc. Natl. Acad. Sci. USA, (2000) 97, 722-727), and by a method for obtaining a phage display-derived human antibody screened from a human antibody library (Wormstone, I. M. et al., Investigative Ophthalmology & Visual Science., (2002) 43 (7), 2301-8; Carmen, S. et al., Briefings in Functional Genomics and Proteomics, (2002) 1 (2), 189-203; Siriwardena, D. et al., Ophthalmology, (2002) 109 (3), 427-431; and so forth).

The specific binding of the resultant human anti-DC-STAMP antibody to DC-STAMP may be appropriately verified, for example, by the ELISA technique as used in evaluation of antibody titers when mice are immunized.

7. Pharmaceutical Agents Containing an Anti-DC-STAMP Antibody

An antibody capable of neutralizing the bioactivity of DC-STAMP may be obtained from anti-DC-STAMP antibodies produced by the method described in section "6. Production of anti-DC-STAMP antibodies" described above. An antibody capable of neutralizing the bioactivity of DC-STAMP may be used as therapeutic agent for metabolic bone disorders caused by abnormal differentiation into osteoclasts, because the antibody inhibits the in vivo bioactivity of DC-STAMP, i.e., differentiation into and/or maturation of osteoclasts.

The neutralizing activity of the anti-DC-STAMP antibody for the in vitro bioactivity of DC-STAMP may be assayed, for example, by its ability to suppress osteoclastic differentiation of cells overexpressing DC-STAMP. For instance, a murine monocyte-derived cell strain, such as RAW264.7 cells, RAW264 cells, or RAW-D cells, overexpressing DC-STAMP may be cultured, then supplied with different levels of the anti-DC-STAMP antibody, and stimulated with RANKL and TNF-α to measure suppression of differentiation of the cells into osteoclasts. Also, a primary cell culture from bone marrow may be supplied with different levels of the anti-DC-STAMP antibody, and stimulated with RANKL and TNF-α to measure suppression of differentiation of the cells into osteoclasts. Furthermore, in a pit assay experiment (Takada et al., Bone and Mineral, (1992) 17, 347-359) using cells from femur and/or tibia, the cells from femur and/or tibia may be supplied with different levels of the anti-DC-STAMP antibody and the formation of pits on ivory pieces observed to measure suppression of osteoclast bone resorption. The therapeutic effect in vivo of the anti-DC-STAMP antibody on metabolic bone disorder in laboratory animals may be examined, for example, by administering the anti-DC-STAMP antibody to transgenic animals overexpressing DC-STAMP and measuring a change in the osteoclasts.

An antibody capable of neutralizing the bioactivity of DC-STAMP thus obtained is useful as a pharmaceutical agent, especially in a pharmaceutical composition to treat diseases such as osteoporosis, rheumatoid arthritis and cancerous hypercalcemia, which are attributable to metabolic bone disorder; or as an antibody for immunological diagnosis of these diseases.

An anti-DC-STAMP antibody may be given, for example, alone or in combination with at least one therapeutic agent for treating bone diseases in order to treat metabolic bone disorder. As an example, an anti-DC-STAMP antibody may be also given together with a therapeutically effective amount of a therapeutic agent against a metabolic bone disorder. The therapeutic agent suitably administered together with the anti-DC-STAMP antibody may include, but is not limited to, bisphosphonates, activated vitamin $D_3$, calcitonin and its derivatives, hormone preparations such as estradiol, SERMs (selective estrogen receptor modulators), ipriflavone, vitamin $K_2$ (menatetrenone), and calcium preparations. Depending on the condition of the metabolic bone disorder and/or the extent of therapy required, two, three or more different agents may be given, or supplied as a formulation having these agents combined therein. These agents and the anti-DC-STAMP antibody may be also supplied as a combined formulation. Further, these agents may be supplied as a therapeutic kit, the agents being contained therein. Also, these agents may be supplied separately from the anti-DC-STAMP antibody.

When the therapy is in the form of gene therapy, the gene for the anti-DC-STAMP antibody may be inserted downstream of the same promoter together with, or separately from, a gene for a proteinaceous therapeutic agent of bone disease, and they may be integrated into different vectors or into the same vector.

Conjugation of an anti-DC-STAMP antibody or a fragment thereof with a therapeutic agent for bone disease can be used to make a targeted drug conjugate as described in M. C. Garnet, "Targeted drug conjugates: principles and progress", Advanced Drug Delivery Reviews, (2001) 53, 171-216. The antibody molecule or fragments thereof may be used for this purpose, unless the fragment completely loses its ability to recognize osteoclasts, Fab, F(ab')2 and Fv are exemplary fragments. The above antibody or fragments thereof can be also used for this purpose in the present invention. The mode of conjugation of the anti-DC-STAMP antibody or a fragment thereof with a therapeutic agent for bone disease may be any of the various forms described in M. C. Garnet, "Targeted drug conjugates: principles and progress", Advanced Drug Delivery Reviews, (2001) 53, 171-216; G. T. Hermanson, "Bioconjugate Techniques", Academic Press, California (1996); Putnam and J. Kopecek, "Polymer Conjugates with Anticancer Activity", Advances in Polymer Science (1995) 122, 55-123; and so forth. Specifically, the anti-DC-STAMP antibody and the therapeutic agent for bone disease may be chemically conjugated directly, or via a spacer, such as an oligopeptide, or conjugated via a suitable drug carrier. Examples of drug carriers include liposomes and aqueous polymers. More specifically, the drug carrier may be used, for example, for encapsulation of both the antibody and the therapeutic agent for bone disease into a liposome, for conjugation of the antibody with the liposome, by chemical bonding of the therapeutic agent of bone disease directly, or via a spacer, such as an oligopeptide, with an aqueous polymer (a compound with a molecular weight of about 1,000 to 100,000), or conjugation of the antibody with an aqueous polymer. The antibody (or fragment thereof), the therapeutic agent for bone disease, and/or the drug carrier, such as a liposome, or aqueous polymer, may bound to each other according to the methods described in G. T. Hermanson, "Bioconjugate Techniques", Academic Press, California (1996); Putnam and J. Kopecek, "Polymer Conjugates with Anticancer Activity" Advances in Polymer Science (1995) 122, 55-123, or the like, which are all well known to those skilled in the art. Encapsulation of the therapeutic agent for bone disease into the liposome may be carried out according to the methods described in D. D. Lasic, "Liposomes: From Physics to Applications", Elsevier Science Publishers B. V., Amsterdam (1993), or the like, which are well known to those skilled in the art. Attachment of the therapeutic agent for bone disease to an aqueous polymer may be carried out according to the methods described in D. Putnam and J. Kopecek, "Polymer Conjugates with Anticancer Activity", Advances in Polymer Science (1995) 122, 55-123, or the like, which are well known to those skilled in the art. The antibody (or fragment thereof) and a proteinaceous therapeutic agent for bone disease (or fragment thereof) may form a fusion protein according to genetic engineering methods well known to those skilled in the art, in addition to the above-described methods.

The present invention also provides a pharmaceutical composition containing a therapeutically effective amount of an anti-DC-STAMP antibody and a pharmaceutically acceptable diluent, carrier, solubilizer, emulsifier, preservative and/or adjunct.

The present invention also provides a pharmaceutical composition containing a therapeutically effective amount of an anti-DC-STAMP antibody, a therapeutically effective amount of at least one therapeutic agent for bone disease and a pharmaceutically acceptable diluent, carrier, solubilizer, emulsifier, preservative and/or adjunct. The therapeutic agent for bone disease may include, but is not limited to, bisphosphonates, activated vitamin $D_3$, calcitonin and its derivatives, hormone preparations such as estradiol, SERMs (selective estrogen receptor modulators), ipriflavone, vitamin $K_2$ (menatetrenone), calcium preparations, PTH (parathyroid hormone) preparations, non-steroidal anti-inflammatory agents, anti-TNFα antibodies, anti-PTHrP (parathyroid hormone-related protein) antibodies, IL-1 receptor antagonists, anti-RANKL antibodies and OCIF (osteoclastogenesis inhibitory factor).

Substances used for formulation of the inventive pharmaceutical composition preferably should be non-toxic to recipients of the pharmaceutical composition, preferably in terms of amounts and concentrations to be given.

The pharmaceutical composition of the invention may contain substances included in the formulation to change, or maintain the pH, osmotic pressure, viscosity, transparency, color, isotonicity, color, sterility, stability, solubility, rate of slow release, absorption and permeability. The substances used for formulation may include, but are not limited to, the following: amino acids such as glycine, alanine, glutamine, asparagine, arginine or lysine; antimicrobials; antioxidants such as ascorbic acid, sodium sulfate or sodium hydrogen sulfite; buffers such as phosphate, citrate, borate buffer, bicarbonate and tris-HCl; bulking agents such as mannitol and glycine and chelating agents such as ethylenediamine tetraacetic acid (EDTA), complexing agents such as caffeine, polyvinyl pyrrolidine, β-cyclodextrin and hydroxypropyl-β-cyclodextrin; fillers such as glucose, mannose or dextrin; other carbohydrates such as monosaccharides and disaccharides; colorants; flavors; diluents; emulsifiers; hydrophilic polymers such as polyvinyl pyrrolidine; low molecular weight peptides; salt-forming paired ions; preservatives such as benzalkonium chloride, benzoic acid, salicylic acid, thimerosal, phenethyl alcohol, methyl paraben, propyl paraben, chlorexidine, sorbic acid or hydrogen peroxide; solvents such as glycerin, propylene glycol and polyethylene glycol; sugar alcohols such as mannitol and sorbitol; suspending agents; surface active agents such as sorbitan esters, polysorbate such as polysorbate 20 or polysorbate 80, triton, tromethamine, lecithin and cholesterol; stability enhancers such as sucrose and sorbitol; elasticity enhancers such as sodium chloride, potassium chloride, mannitol and sorbitol; transport agents; diluents; excipients; and/or pharmaceutical adjuncts. These substances used in formulation may be added at 0.01 to 100 times, preferably at 0.1 to 10 times, the weight of the anti-DC-STAMP antibody. The pharmaceutical composition may be formulated by those skilled in the art, as appropriate, depending on the disease against which it is to be used, the administration route used therefor and the like.

The excipient or carrier used in the pharmaceutical composition may be liquid or solid. A suitable excipient or carrier may be water or physiological saline used for injection, artificial cerebrospinal fluid or other substances typically used for parenteral administration. The carrier may be neutral physiological saline or physiological saline containing serum albumin. The pharmaceutical composition may contain tris buffer at pH 7.0-8.5 or acetate buffer at pH 4.0-5.5, which may contain sorbitol or other compounds. A pharmaceutical composition according to the present invention includes a pharmaceutical composition containing the anti-DC-STAMP antibody, as well as a pharmaceutical composition containing the anti-DC-STAMP antibody and at least one therapeutic agent for bone disease. A pharmaceutical composition of the present invention is provided as a suitable formulation, having a selected composition and a required purity, which may be in the form of a lyophilized product or liquid. A pharmaceutical composition containing an anti-DC-STAMP antibody, or a pharmaceutical composition containing an anti-DC-STAMP antibody and at least one therapeutic agent for metabolic bone disorder may be a lyophilized product, formed with the help of a suitable excipient such as sucrose.

A pharmaceutical composition of the present invention may be prepared for parenteral administration or for oral administration for absorbtion in the gastrointestinal tract. The composition and a concentration of the formulation may be determined by the method of administration. The affinity of an anti-DC-STAMP antibody contained in a pharmaceutical composition of the invention for DC-STAMP is high. This may be represented by the dissociation constant for DC-STAMP (the value of Kd). A high affinity (a lower Kd), means that the antibody is effective in a human subject at a low dose. The dosage level of a pharmaceutical composition of the invention for a human subject may be determined based on the value of Kd. The dosage level for a human subject may be a single dose of about 0.1 to 100 mg/kg given once per 1 to 30 days when a humanized anti-DC-STAMP antibody is the active agent.

A pharmaceutical composition of the present invention may be a dosage form such as an injection (including drops), suppository, intranasal agent, sublingual tablet, transdermal absorption agent or the like.

8. Search for Directly Interacting Substances

Another aspect of the present invention includes an approach to drug design based on the conformation of the DC-STAMP protein in order to provide a substance capable of suppressing DC-STAMP activity. This approach, known as rational drug design, is utilized to search for a compound that can inhibit or enhance effectively a function such as enzymatic activity, or binding to a ligand, cofactor or DNA. One such well known example is a protease inhibitor which is now on the market as an anti-HIV agent. The three-dimensional structure of DC-STAMP in the present invention may be analyzed by means of generally well-known techniques such as X-ray crystallographic analysis and nuclear magnetic resonance. In addition, a substance capable of suppressing the function of DC-STAMP may be designed taking advantage of computer assisted drug design (CADD) to search for such a substance. Such known examples include a low molecular-weight compound which is a promising novel genome-based drug to treat rheumatoid arthritis and inhibits the action of AP-1 (WO patent application 99/58515). In this way, a substance capable of suppressing the function of DC-STAMP may be identified which can bind directly to DC-STAMP or inhibit the interaction of DC-STAMP with another factor.

Yet another aspect relates to a polypeptide capable of associating with DC-STAMP of the present invention, i.e., a partner protein for DC-STAMP. Thus, the present invention relates to a method of screening for a partner protein which regulates the activity of DC-STAMP.

One aspect of the screening method includes a step of exposing test protein samples to DC-STAMP and selecting a protein capable of binding to DC-STAMP. In this method, for instance, purified DC-STAMP is used and a protein is allowed to bind thereto, and the bound protein is purified by affinity means. As a specific example, DC-STAMP can be fused with a sequence of six histidine molecules that act as an affinity tag, the resulting fusion product is incubated with a cell extract (an eluate fraction preliminarily prepared by charging the cell extract into a nickel-agarose column and passing the extract through the column) at 4° C. for 12 hours, and then the mixture is applied to another nickel-agarose support and further incubated at 4° C. for 1 hour. The nickel-agarose support is washed well with wash buffer and 100 mM imidazole is added to release/purify the protein derived from the cell extract which is capable of specifically binding to DC-STAMP, which protein will be characterized structurally. In this way, it is possible to purify a protein capable of binding directly to DC-STAMP, and a protein incapable of binding directly to DC-STAMP but capable of indirectly binding thereto by complexing as a subunit with another protein directly binding thereto (Experimental Medicine, Separate Volume, Biological Technology Manual Series 5: "Method of Study on Transcription Factor", 215-219, Yodosha Co, Ltd.).

Other methods may include cloning by far western blotting (Experimental Medicine, Separate Volume, "New Handbook on Genetic Engineering", 76-81, Yodosha Co, Ltd.) or a two hybrid system method using yeast or mammalian cells (Experimental Medicine, Separate Volume, "New Handbook on Genetic Engineering", 66-75, Yodosha Co, Ltd.; "Checkmate Mammalian Two Hybrid System" made by Promega Corporation), but are not limited thereto.

If a cDNA for the partner protein that interacts directly or indirectly with DC-STAMP is provided in this way, then it is useful for functional screening of a substance capable of inhibiting interaction between DC-STAMP and the partner protein. Specifically, for instance, a fusion protein of DC-STAMP with glutathione-5-transferase is prepared, and attached to a microplate covered with an anti-glutathione-5-transferase antibody, and then contacted with a biotinylated partner protein to detect its conjugation therewith using streptavidin-bonded alkaline phosphatase. In adding the biotinylated partner protein, each test substance is also added to find/select a substance which may enhance or inhibit the conjugation of the fusion protein to the partner protein. In this method, a substance that acts directly either on the fusion protein or the partner protein can be identified.

If conjugation of the fusion protein with the partner protein is indirect via some third party factor, then the above assay can be carried out further, for example, in the presence of such cell extract as may contain the factor. In this case, a substance that may act on the factor may be selected.

If the resultant partner protein enhances the function of DC-STAMP, candidate substances useful as therapeutic agents for a metabolic bone disorder, for example, osteoporosis, may be identified according to the test procedure described above in which an expression vector with the DC-STAMP gene is used. Alternatively, if the resultant partner protein suppresses the function of DC-STAMP, a polynucleotide having a nucleotide sequence encoding such a suppressive factor may be used for gene therapy of metabolic bone disorder.

Such a polynucleotide may be obtained, for example, by analyzing the amino acid sequence of the identified inhibitor, synthesizing an oligonucleotide probe comprising a nucleotide sequence encoding the amino acid sequence, and screening a cDNA or genome library therewith. If a peptide inhibiting the function of DC-STAMP is derived from an artificial randomly generated peptide library, a DNA comprising a nucleotide sequence encoding the amino acid sequence of the peptide can be synthesized chemically.

In gene therapy, a gene encoding the inhibitor thus obtained can be integrated, for example, into a viral vector and a patient can then be infected with a non-virulent virus containing the recombinant viral vector. In the patient, an anti-osteoclastic factor may be produced to suppress differentiation into osteoclasts and thereby treat metabolic bone disorder.

To introduce a gene therapy agent into cells, gene transfer using a viral vector, or non-viral gene transfer, is available (Nikkei Science, April, 1994, pp. 20-45; Experimental Medicine, Extra Number, 12 (15) (1994); Experimental Medicine, Separate Volume, "Basic Technology of Gene Therapy", Yodosha Co, Ltd. (1996)).

For the purpose of gene transfer by a viral vector, a DNA encoding an inhibitor for DC-STAMP or a variant of the DNA is integrated, for example, into a DNA or RNA virus, such as retrovirus, adenovirus, adeno-associated virus, herpesvirus, vaccinia virus, poxvirus, poliovirus or Sindbis virus. Of the viruses, retrovirus, adenovirus, adeno-associated virus, or vaccinia virus are particularly preferred. Non-virus-mediated gene transfer may include direct injection of an expression plasmid into a muscle (DNA vaccination), the liposome method, lipofection, microinjection, calcium phosphate transfection and electroporation; DNA vaccination and the liposome method are particularly preferred.

To allow a gene therapeutic agent to act as drug, in vivo processes for administering DNA directly into the body are available, as well as the ex vivo process of removing a certain cell type from the human body, introducing DNA into the cells in vitro, and returning the cells into the body (Nikkei Science, April, 1994, pp. 20-45; The Pharmaceuticals Monthly, 36(1), 23-48 (1994); Experimental Medicine, Extra Number, 12 (15) (1994)).

For instance, when gene therapeutic agent is given by an in vivo process, it is given via a suitable route of administration, such as intravenously, intra-arterially, subcutaneously, intradermally or intramuscularly, depending on the disease type, symptoms and so forth. When a gene therapeutic agent is given by the in vivo process, typically it may be in the form of an injection, optionally containing a conventional carrier. Further, when it is in the form of liposome or membrane-fused liposome (Sendai virus-liposome or the like), it may be formulated into suspension, lyophilizate, centrifugally-concentrated lyophilizate or the like.

A complement to the nucleotide sequence given in SEQ ID NO: 1 in the Sequence Listing, or a complement to a partial sequence thereof may be used in so-called antisense therapy. Antisense molecules may be used in the form of a DNA typically comprising 15 to 30 mers complementary to a portion of a nucleotide sequence selected from the nucleotide sequences given in SEQ ID NOS: 1, 3 and 5 in the Sequence Listing, or a stable DNA derivative thereof such as a phosphorothioate, methylphosphonate or morpholino derivative, or a stable RNA derivative such as 2'-O-alkyl RNA. The antisense molecules may be incorporated into cells to express them therein by any method known in the art to which the present invention belongs, such as microinjection, liposome encapsulation or use of a vector having an antisense sequence. Such antisense therapy is useful to treat diseases caused by an excessive increase in activity of the protein which is encoded by the nucleotide sequence given in SEQ ID NO: 1 in the Sequence Listing.

Also, double-stranded short RNA (siRNA) can be used (Genes and Developments, 15th/Jan./2001, 15, 2, pp. 188-200). For instance, siRNA against the DC-STAMP gene may be prepared and introduced into cells, according to the method described in the aforementioned document, to treat disease due to metabolic bone disorder caused by over-expression of DC-STAMP.

A pharmaceutically useful composition containing the antisense oligonucleotide and/or siRNA may be prepared by a known method including mixing of the active agent with a pharmaceutically acceptable carrier. Carriers for a pharmaceutical agent containing an antisense oligonucleotide and methods of producing the agent are exemplified in "Applied Antisense Oligonucleotide Technology" (1988, Wiley-Liss, Inc.). A pharmaceutical formulation containing the antisense oligonucleotide and/or siRNA may be prepared by mixing the active agent with pharmacologically acceptable excipient(s) and/or diluent(s), and administered orally in the form of tablet, capsule, granule, powder, syrup or the like, or parenterally in the form of injection, suppository, patch, topical drug or the like. These formulations may be produced by well-known processes using additives such as: excipients (including, for example, sugar derivatives such as lactose, sucrose, glucose, mannitol and sorbitol; starch derivatives such as corn starch, potato starch, a starch and dextrin; cellulose derivatives such as crystalline cellulose; organic excipients such as acacia gum, dextran and pullulan; and inorganic excipients, such as silicate derivatives such as light silicic acid anhydride, synthetic aluminum silicate, calcium silicate and magnesium metasilicate aluminate; phosphates such as calcium hydrogen phosphate; carbonates such as calcium carbonate; and sulfates such as calcium sulfate); lubricants (including, for example, stearic acid and metal stearates such as calcium stearate and magnesium stearate; talc; colloidal silica; waxes such as bees wax and whale wax; boric acid; adipic acid; sulfates such as sodium sulfate; glycols; fumaric acid; sodium benzoate; DL leucine; lauryl sulfates such as sodium lauryl sulfate and magnesium lauryl sulfate; silicic acids such as silicic acid anhydride and hydrated silicic acid; and the above-described starch derivatives); binders (including, for example, hydroxypropylcellulose, hydroxypropylmethylcellulose, polyvinylpyrrolidone, macrogol and compounds as shown in above-described excipients); disintegrants (including, for example, chemically-modified starches and celluloses represented by cellulose derivatives such as low substituted hydroxypropylcellulose, carboxymethylcellulose, calcium carboxymethylcellulose and internally cross-linked sodium carboxymethylcellulose; and carboxymethylstarch, sodium carboxymethylstarch, cross-linked polyvinylpyrrolidone and the like); emulsifiers (including, for example, colloidal clays such as bentonite and bee gum; metal hydroxides such as magnesium hydroxide and aluminum hydroxide; anionic surfactants such as sodium lauryl sulfate and calcium stearate; cationic surfactants such as benzalkonium chloride; and non-ionic surfactants such as polyoxyethylene alkyl ether, polyoxyethylene sorbitan fatty esters and sucrose fatty esters); stabilizers (including p-hydroxybenzoic esters such as methylparaben and propylparaben; alcohols such as chlorobutanol, benzylalcohol and phenylethylalcohol; benzalkonium chloride; phenols such as phenol and cresol; thimerosal; dehydroacetic acid; and sorbic acid); flavoring agents (including, for example, commonly used sweeteners, acidulants and perfumes); diluents and others.

Colloid dispersions can be used in addition to the forms described above in order to administer the pharmaceutical agents to patients. Colloid dispersions are expected to enhance the stability of a compound in vivo and efficiently transport the compound into particular organs, tissues or cells. The choice of commonly-used colloid dispersions is not limited, and they may include lipid-based dispersions encompassing polymer composites, nanocapsules, microspheres, beads, and emulsifiers in oil/water systems, micelles, mixed micelles and liposomes, preferably multiple liposomes or artificial lamellar vesicles capable of efficiently transporting the compound into particular organs, tissues or cells (Mannino et al., Biotechniques, (1988) 6, 682; Blume and Cevc, Biochem. et Biophys. Acta, (1990) 1029, 91; Lappalainen et al., Antiviral Res., (1994) 23, 119; Chonn and Cullis, Current Op. Biotech., (1995) 6, 698).

Unilamellar liposomes in the range of from 0.2-0.4 µm in size may encapsulate a significant proportion of an aqueous buffer containing macromolecules. The compound may be encapsulated in an aqueous environment within the lamella and transported into brain cells while maintaining biologically activity (Fraley et al., Trends Biochem. Sci., (1981) 6, 77). Liposomes are typically composed of lipid, particularly phospholipid, above all, phospholipid with a high phase transfer temperature, which are commonly conjugated with at least one kind of steroid, particularly cholesterol. Examples of lipids useful for production of liposomes include phosphatidyl compounds, such as phosphatidyl glycerol, phosphatidyl choline, phosphatidyl serine, sphingolipids, phosphatidyl ethanolamine, cerebrosides and gangliosides. Particularly useful lipids are diacyl phosphatidyl glycerols, where the lipid portion contains 14-18 carbon atoms, especially 16-18 carbon atoms, and are saturated (the 14-18 carbon chain has no double bond therein). Representative phospholipids include phosphatidyl choline, dipalmitoyl phosphatidyl choline, and distearoyl phosphatidyl choline.

Targeting of colloidal dispersions containing liposomes may be either passive or active. Passive targeting is achieved by use of the intrinsic property of liposomes migrating to distribute among the cells of the reticuloendothelial system in organs containing sinusoidal capillaries. In contrast, active targeting is achieved, for example, by binding a particular ligand to liposomes, which ligand includes a viral protein coat (Morishita et al., Proc. Natl. Acad. Sci. USA, (1993) 90, 8474), monoclonal antibody (or a suitable binding site thereof) and sugar, glycolipid or protein (or a suitable oligopeptide fragment thereof), or by varying liposome composition or modifying liposomes to allow the liposomes to distribute into organs or cell types other than native localized sites. The surface of the dispersed colloids which are to be targeted may be modified in various ways. In delivery systems using targeted liposomes, the lipid bilayer of the liposomes may take up the lipid portion of a targeting ligand to keep the ligand in close association with the lipid bilayer. The lipid chain may be linked with the targeting ligand through various linkers. A targeting ligand capable of binding to a particular cell-surface molecular species predominantly present on the cells to which delivery of the oligonucleotide of the invention is desired may be: for example, (1) a hormone, a growth factor or an appropriate oligopeptide fragment thereof that can bind to a particular cell receptor predominantly expressed by the cells to which the delivery is desired, or (2) a polyclonal or monoclonal antibody or an appropriate fragment thereof (for example, Fab or F(ab')2) capable of binding specifically to an antigenic epitope predominantly present on the target cells. Also, two or more bioactive agents may be conjugated within the same liposomes for suitable dosage. Such a substance may be added to the colloidal dispersion to enhance intracellular stability and/or targeting of the drug content.

The colloidal dispersion may be given at various doses depending on symptoms, age etc., but at a unit dose of at least 1 mg (suitably 30 mg) and at most 2,000 mg (suitably 1,500 mg) in case of oral dosage, and of at least 0.1 mg (suitably 5 mg) and at most 1,000 mg (suitably 500 mg) in case of injection, to be specific, injection subcutaneously, intramuscularly or intravenously.

The present invention will be now described in detail and specifically with reference to the Examples, but is not limited thereto. In the following Examples, the respective techniques for genetic manipulation were performed according to the methods described in Molecular Cloning (Sambrook, J., Fritsch, E. F. and Maniatis, T., Ed., Cold Spring Harbor Laboratory Press, 1989) unless otherwise stated, or according to the manufacturer's instructions when commercial reagents or kits are used.

REFERENCE EXAMPLE 1

Establishment of RAW-D Cells and RAW-N Cells
a) Isolation of RAW-D Cells and RAW-N Cells by Limiting Dilution Culture Stimulation of murine monocyte-derived cell strain RAW264.7 with soluble RANKL is known to strongly induce gene expressions for markers of differentiation into osteoclasts, such as tartrate resistant acid phosphatase (hereinafter referred to as "TRAP") and cathepsin K (Hsu et al., Proc. Natl. Acad. Sci. USA, (1999) 96, 3540-3545). Consequently, stimulation of RAW264.7 cells with RANKL is believed to induce their differentiation into osteoclasts. It was thus attempted to obtain cells subcloned from the parent strain RAW264 cells, designated RAW264.7 cells, which would be more sensitive to RANKL and TNF-α, or more differentiation by these stimuli (Watanabe et al., J. Endocrinol., (2004) 180, 193-201). RAW264 cells can be purchased from The European Collection of Cell Cultures (Catalog No. 85062803). The RAW264 cells were subjected to limiting dilution in the normal manner, using α-MEM medium containing 10% fetal calf serum and plated on a 96-well plate in 100 µl aliquots. They were cultured for 10-14 days and the colonies formed were harvested. Each colony was prepared at $4.5 \times 10^4$ cells/ml in α-MEM medium containing 10% fetal calf serum. The preparation was plated on a 96-well plate at 150 µl/well, and the following were added: human RANKL (from PeproTech Inc.) to a final concentration of 20 ng/ml and human TNF-α (from PeproTech Inc.) to a final concentration of 1 ng/ml. The cells were cultured for 3 days and then stained for TRAP with a Leukocyte Acid Phosphatase kit (from Sigma Co.) according to the protocol provided therewith to check for formation of TRAP positive multinuclear osteoclasts. This series of cloning procedures through limiting dilution culture was repeated twice for each colony.

As a result, RAW-D cells capable of efficiently differentiating to osteoclasts following stimulation with RANKL and TNF-α were obtained, as well as RAW-N cells totally incapable of differentiating to osteoclasts following stimulation with RANKL and TNF-α.

b) Study by TRAP Staining on the Tendencies of RAW-D Cells and RAW-N Cells to Differentiate to Osteoclasts The RAW-D cells and RAW-N cells were examined for their responses to stimulation with osteoclast-inducing substances such as RANKL and TNF-α. The RAW-D, RAW-N and RAW264 cells were prepared at $4.5 \times 10^4$ cells/ml in α-MEM medium containing 10% fetal calf serum, respectively. Each preparation was plated on a 96-well plate at 150 µl/well, and the following were added: human TNF-α (from PeproTech Inc.) to a final concentration of 1 ng/ml and human RANKL (from PeproTech Inc.) to a final concentration of 10, 20, 40 or 80 ng/ml. The cells were cultured for 3 days and then stained for TRAP with a Leukocyte Acid Phosphatase kit (from Sigma Co.) according to the protocol provided therewith to count the number of TRAP positive osteoclasts formed. As a result, the RAW-D cells formed TRAP positive multinuclear osteoclasts depending on the concentration of the RANKL added (FIG. 1). In contrast, the RAW-N and RAW264 cells, i.e., the parent strain, were not observed to form TRAP positive osteoclasts in response to addition of the RANKL.

EXAMPLE 1

Expression of mRNA for murine DC-STAMP in RAW-D or RAW-N (northern blot analysis)
a) Extraction of Total RNA RAW-D and RAW-N were prepared at $7 \times 10^4$ cells/ml in α-MEM medium containing 10% fetal calf serum, respectively. Each preparation was plated on a 24-well plate at 500 µl/well, and the following were added: human RANKL (from PeproTech Inc.) to a final concentration of 20 ng/ml, human TNF-α (from PeproTech Inc.) to a final concentration of 2 ng/ml and murine MIP-1α (from PeproTech Inc.) to a final concentration of 1 ng/ml, and cultured for 3 days. In parallel, each preparation was also cultured in the absence of human RANKL (from PeproTech Inc.), human TNF-α and murine MIP-1α.

Afterwards, the total RNA was extracted from RAW-D or RAW-N, cultured under the conditions described above, using a total RNA extraction reagent (TRIZol reagent from Invitrogen Corporation) according to the protocol provided therewith. The total RNA recovered was stored at −80° C.

b) Electrophoresis and Blotting of Total RNA

The recovered total RNA was prepared at 0.5 µg/µl in RNA sample buffer (1×MOPS buffer-containing 20 mM MOPS, 8 mM sodium acetate and 1 mM EDTA), 50% formamide, 18 µg/ml bromophenol blue, 5.8% formaldehyde, 5% glycerol), kept at 65° C. for 15 minutes, and cooled rapidly on ice for 5 minutes. A 20 µl aliquot of the sample solution was dispensed into a well on a 1% agarose gel including formaldehyde for electrophoresis (1×MOPS buffer, 1.2% agarose (from Sigma Co.), 6% formaldehyde) and was subjected to electrophoresis. Electrophoresis was carried out by applying electric current through a submarine electrophoretic bed containing 1×MOPS buffer at 100 V for about 3 hours.

After electrophoresis, the RNA in the agarose gel was transferred to a nylon membrane (Hibond N+ from Amersham Pharmacia Biotech) overnight by the capillary transfer technique (Maniatis, T. et al., in "Molecular Cloning A Laboratory Manual", Cold Spring Harbor Laboratory, NY, (1982))(a solution for transfer was 20×SSC). The membrane was washed with 2×SSC for 5 minutes, air-dried, and exposed to UV light (300 mJ/cm$^2$) on a crosslinking black light (Stratalinker 2400 from Stratagene Corporation) to immobilize the RNA.

c) Preparation of Probes

A plasmid DNA, which was prepared by inserting a nucleotide sequence represented by the nucleotide sequence at positions 457 to 1208 of the murine DC-STAMP ΔT7 cDNA (SEQ ID NO: 5 in the Sequence Listing; GenBank Accession No: AB109561) into the TA cloned site of pGEM-T Easy vector (from Promega Corporation), was digested with NcoI (from Takara Shuzo Co., Ltd.) at the NcoI site near the TA cloned site to make a linear DNA. An antisense RNA probe labeled with DIG (digoxigenin) was prepared by using DIG RNA labeling mix (from Roche Diagnostics K.K.) and SP6 RNA polymerase (from Roche Diagnostics K.K.) according to the protocols provided therewith. This liquid probe preparation was mixed with 20 units of RNase-free DNase I (from Roche Diagnostics K.K.) to digest the template DNA. The RNA probe thus prepared can detect mRNAs for both DC-STAMP and DC-STAMP ΔT7, since the probe corresponds to the nucleotide sequences represented by positions 457 to 1078 and 1247 to 1376 in the SEQ ID NO: 3 (murine DC-STAMP cDNA) in the Sequence Listing.

d) Hybridization

The membrane prepared in b) was placed in a 6 ml hybridization solution (a solution of DIG Easy Hyb Granules from Roche Diagnostics K.K. in redistilled water prepared according to the protocol provided therewith), incubated at 65° C. for 15 minutes (pre-hybridization), and then incubated at 65° C. for 16 hours in a 6 ml hybridization solution containing the DIG-labeled RNA probe. Thereafter, the membrane was washed twice in a solution of 2×SSC containing 0.1% SDS at ambient temperature for 5 minutes, and further washed twice in a solution of 0.5×SSC containing 0.1% SDS at 65° C. for 30 minutes. Next, the membrane was treated with a blocking solution (a solution of a blocking reagent from Roche Diagnostics K.K. in a maleate buffer prepared according to the protocol provided therewith) for 30 minutes and with a blocking solution containing alkaline phosphatase-labeled anti-digoxigenin Fab fragments (0.075 units/ml) (from Roche Diagnostics K.K.) for 30 minutes. Further, the membrane was washed three times with a wash buffer (5 mM maleate buffer, pH 7.5, 150 mM NaCl, 0.3% Tween 20) for 15 minutes, CDP-Star (from Roche Diagnostics K.K.) was added as the luminescent substrate, and analyzed with a Luminoimage Analyzer (LAS-1000 plus from Fuji Photo Film Co., Ltd.).

Figure 2:
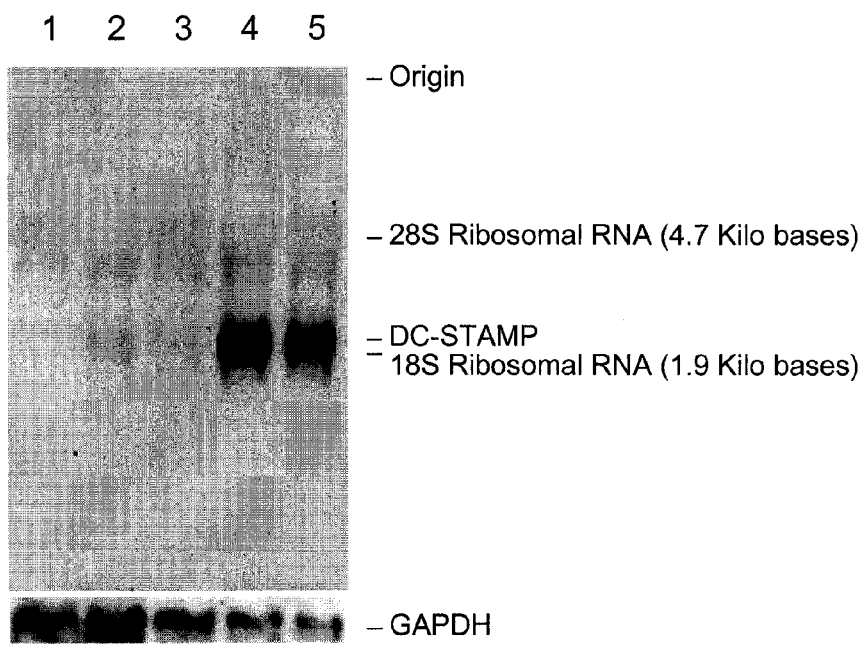
FIG. 2 is a diagram showing expression of DC-STAMP mRNA associated with differentiation of RAW-D cells into osteoclasts.

As a result, RAW-D was shown to have little expression of the murine DC-STAMP in the absence of RANKL and TNF-α, but a significantly increased expression of the murine DC-STAMP in the presence of RANKL and TNF-α (FIG. 2). The expression of the murine DC-STAMP was not further increased by addition of MIP-1α.

On the other hand, RAW-N had little or no expression of the DC-STAMP either in the absence or in the presence of RANKL and TNF-α. It should be added that the expression of the murine glyceraldehyde-3-phosphate dehydrogenase (GAPDH) was also determined as a control.

EXAMPLE 2

Expression of mRNA for Murine DC-STAMP in RAW-D (RT-PCR Analysis)

RAW-D was prepared at 7×10$^4$ cells/ml in α-MEM medium containing 10% fetal calf serum. The preparation was plated on a 24-well plate at 500 μl/well, and the following were added: human RANKL (from PeproTech Inc.) to a final concentration of 20 ng/ml, human TNF-α (from PeproTech Inc.) to a final concentration of 2 ng/ml and murine MIP-1α (from PeproTech Inc.) to a final concentration of 1 ng/ml, and cultured for 0, 4, 8, 16, 32, 48 or 72 hours.

Thereafter, at each time point of culture total RNA was extracted from RAW-D using a total RNA extraction reagent (TRIZol reagent from Invitrogen Corporation) according to the protocol provided therewith. The total RNA recovered was stored at −80° C. until it was used. The total RNA (1 μg) and 1 μl of oligo(dT) 18 primer (0.5 μg/μl) were added to H$_2$O to make a 11 μl solution, which was then heated at 70° C. for 10 minutes and then stored at 4° C. To the solution were added: 4 μl of 5×1st Strand Buffer (from Invitrogen Corporation), 1 μl of 10 mM dNTPs, 2 μl of 0.1 M dithiothreitol, 1 μl of Superscript II reverse transcriptase (200 U/μl from Invitrogen Corporation), and 1 μl of H$_2$O to make a total 20 μl solution, which underwent a reaction at 42° C. for 1 hour, and was then heated at 70° C. for 10 minutes and stored at 4° C.

The resultant single-stranded cDNA was amplified with each pair of primers as described below.

PCR conditions:

```
Primers for amplifying murine DC-STAMP and murine
DC-STAMP ΔT7:
5'-aaaacccttg ggctgttctt-3'
(mDC-STAMP-F: SEQ ID NO: 7 in the Sequence
Listing)
and 5'-cttcgcatgc aggtattcaa-3'
(mDC-STAMP-R: SEQ ID NO: 8 in the Sequence
Listing)

Primers for amplifying murine cathepsin K:
5'-gagggccaac tcaagaagaa-3'
(mcatK-F: SEQ ID NO: 9 in the Sequence Listing)
and 5'-gccgtggcgt tatacataca-3'
(mcatK-R: SEQ ID NO: 10 in the Sequence Listing)

Primers for amplifying murine TRAP:
5'-cagctgtcct ggctcaaaa-3'
(mTRAP-F: SEQ ID NO: 11 in the Sequence Listing)
and 5'-acatagccca caccgttctc-3'
(mTRAP-R: SEQ ID NO: 12 in the Sequence Listing)

Primers for amplifying murine GAPDH:
5'-aaaccatca ccatcttcca-3'
(mGAPDH-F: SEQ ID NO: 13 in the Sequence Listing)
and 5'-gtggttcaca cccatcacaa-3'
(mGAPDH-R: SEQ ID NO: 14 in the Sequence Listing)
```

PCR was conducted under the conditions described below using a thermal cycler (GeneAmp PCR System 9700 from Applied Biosystems Division, Perkin Elmer Japan Co., Ltd.). Platinum Taq DNA Polymerase (from Invitrogen Corporation) was used for the reaction. To distilled water were added 8 pmol of each primer, 20 ng of the single-stranded cDNA, 0.5 μl of 10× reaction buffer, 0.2 μl of 50 mM MgCl$_2$, 0.4 μl of each 2.5 mM dNTP, and 0.05 μl of Taq DNA polymerase (5 units/μl) to make 5 μl of a reaction solution. The reaction solution was heated at 94° C. for 2 minutes, treated repeatedly 30 times with a temperature cycle of 94° C. for 0.5 minutes, 65° C. for 1 minute, and 72° C. for 1 minute, then heated at 72° C. for 10 minutes and kept at 4° C. The whole reaction solution was subjected to electrophoresis on a 2.0% agarose gel.

Figure 3:
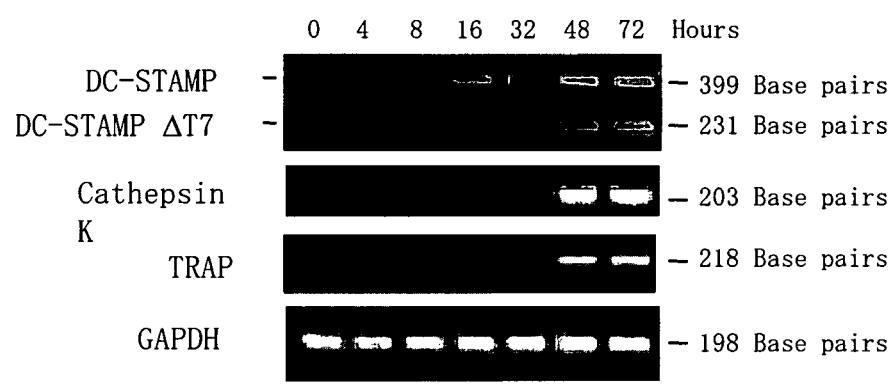
FIG. 3 is a diagram showing expression of DC-STAMP mRNA in RAW-D cells stimulated with RANKL, TNFα and MIP-1α, respectively.

The DC-STAMP gene began to be expressed 8 hours after RANKL, TNF-α and MIP-1α were added, and its expression level continued to increase until 72 hours (FIG. 3). The DC-STAMP ΔT7, which is a splice variant having a short third exon, was also observed to be expressed at a higher level 16 hours after RANKL, TNF-α and MIP-1α were added, and subsequently. Furthermore, genes for cathepsin K and TRAP, which are molecular markers for osteoclasts, were observed to be expressed at higher levels after 16 hours and subsequently. In FIG. 3, the upper-side numbers indicate the lapses of time, by hour, after RANKL, TNF-α and MIP-1α were added, and on the right hand side, the size of each gene product amplified in a PCR reaction is indicated by the number of base pairs.

EXAMPLE 3

Expression of mRNA for Murine DC-STAMP in Murine Bone Marrow-Derived Primary Culture Cells (RT-PCR Analysis)

When murine bone marrow-derived primary culture cells are cultured in the presence of activated vitamin $D_3$, a large number of TRAP-positive multinuclear osteoclasts appear (Takahashi et al., Endocrinology, (1988) 122, 1373-1382).

A male DDY mouse aged 6 weeks was euthanized by cervical dislocation under ether anesthesia to remove femur and tibia. The femur and tibia were stripped of soft tissues and cut on both ends, respectively. A serum-free α-MEM medium was infused into the bone marrow using a syringe with a 25-gauge needle to collect bone marrow cells. The cell number was counted, and the cells were prepared at $2 \times 10^6$ cells/ml in α-MEM medium containing 15% fetal calf serum. The preparation was plated on a 24-well plate at 500 μl/well, and activated vitamin $D_3$ was added (Biomol International LP) to a final concentration of $1 \times 10^{-8}$ M. The cells were cultured for 1, 3, 5 or 6 days.

Thereafter, at each time point of culture total RNA was extracted from the cells using a total RNA extraction reagent (TRIZol reagent from Invitrogen Corporation) according to the protocol provided therewith. The total RNA recovered was stored at −80° C. until it was used.

An RT-PCR reaction was conducted using a RNA LA PCR kit (AMV) Ver1.1 (Takara Biochemicals Inc.). First, the following were mixed to make a 10 μl reaction solution: 2 μl of 25 mM $MgCl_2$, 1 μl of 10×RNA PCR Buffer, 1 μl of dNTP Mix (10 mM each), 0.25 μl of RNase Inhibitor (40 U/μl), 0.5 μl of reverse transcriptase (5 U/μl), 0.5 μl of Oligo dT-Adapter primer (2.5 pmol/μl), 1 μg of the total RNA and RNase-free $dH_2O$. Then, the reaction solution was heated at 50° C. for 25 minutes, then heated at 99° C. for 5 minutes and then stored at 4° C. The resulting single-stranded cDNA was amplified with each pair of the primers described in Example 2.

PCR was conducted under the conditions described below using a thermal cycler (GeneAmp PCR System 9700). To 5 μl of the reaction solution containing cDNA the following were added: 1.5 μl of 25 mM $MgCl_2$, 2 μl of 10×LA PCR Buffer II ($Mg^{2+}$ free), 0.125 μl of Takara LA Taq (5 U/μl), a primer set (1 μM each of final concentration), and redistilled water to make a 25 μl reaction solution. The reaction solution was heated at 94° C. for 2 minutes, treated repeatedly 25 times with a temperature cycle of 94° C. for 30 seconds, 60° C. for 30 seconds, and 72° C. for 30 seconds, and then stored at 4° C. A 9 μl aliquot of the reaction solution was subjected to electrophoresis on a 2.0% agarose gel.

Figure 4:
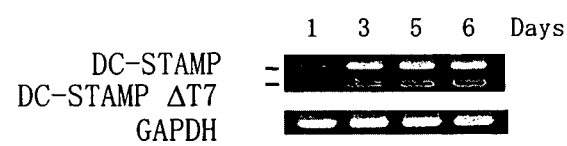
FIG. 4 is a diagram showing expression of DC-STAMP mRNA in primary bone marrow cells stimulated with activated vitamin D3.

As a result, the DC-STAMP gene was expressed slightly 1 day after activated vitamin $D_3$ was added, but expressed pronouncedly after 3 days when mononuclear osteoclastic precursor cells were formed, and still expressed pronouncedly after 5 and 6 days when multinucleation occurred actively (FIG. 4).

DC-STAMP ΔT7 was expressed at a lower level than DC-STAMP, but the time course of its expression was similar to that of DC-STAMP. In FIG. 4, the upper-side numbers indicate elapses of time, by day, after activated vitamin $D_3$ was added.

EXAMPLE 4

Preparation of Rabbit Anti-Mouse DC-STAMP Polyclonal Antibody

From the murine DC-STAMP amino acid sequence (SEQ ID NO: 4 in the Sequence Listing; GenBank Accession No: AB109560), preparation of a partial peptide of the murine DC-STAMP protein was attempted based on a peptide comprising an amino acid sequence which is located between the 6th and 7th transmembrane domains and represented by amino acids of positions 330 to 343. A partial peptide having the above-described sequence plus a cysteine residue bound on its N-terminus:

Cys Ser Leu Pro Gly Leu Glu Val His Leu Lys Leu

Arg Gly Glu (SEQ ID NO: 15 in the Sequence Listing)

was synthesized. This peptide was conjugated to KLH (keyhole limpet hemocyanin), which is an antigen-stimulating carrier protein, by the MBS (maleimidebenzoyloxysuccinimide) process. A rabbit was immunized with the conjugate to obtain rabbit antiserum as usual. The antiserum was purified by passing it through a peptide affinity column onto which the partial peptide used for immunization was immobilized to provide rabbit anti-mouse DC-STAMP polyclonal antibody. Since DC-STAMP ΔT7 (GenBank Accession No: AB109561) also contains this peptide sequence, the antibody was considered to bind to both DC-STAMP and DC-STAMP ΔT7. This peptide sequence was further compared with a sequence represented by amino acids of positions 330 to 343 in the human DC-STAMP amino acid sequence (SEQ ID NO: 2 in the Sequence Listing; GenBank Accession No: NM_030788). As a result, both sequences were found to be identical except that Leu (mouse) at position 334 was replaced by Phe (human) and Arg (mouse) at position 341 was replaced by His (human), and thus the antibody was very likely to bind also to the human DC-STAMP.

EXAMPLE 5

Immunostaining in Neonatal Mouse Tibia-Derived Osteoclasts a) Sampling of Neonatal Mouse Tibia-Derived Osteoclasts Tibia was removed from a DDY mouse aged 1 day and stripped of the soft tissue. The tibia was minced with postmortem scissors in A-MEM medium containing 15% fetal calf serum and then pipetted a little harder to disperse and suspend the cells. The cell suspension was plated on a chamber slide (from Nalge Nunc International) and cultured for 1 hour to provide multinuclear cells adhering to the slide as osteoclasts.

b) Development of DC-STAMP Protein with Immunostaining

The osteoclasts obtained in a) were fixed with a 4% paraformaldehyde solution at ambient temperature for 20 minutes, washed four times with phosphate-buffered saline (pH 7.4), and blocked with phosphate-buffered saline (pH 7.4) containing 3% goat serum at ambient temperature for 30 minutes. After the blocking solution was removed, the following solution was added to the osteoclasts phosphate-buffered saline (with 1% horse serum) containing the rabbit anti-mouse DC-STAMP polyclonal antibody (10 μg/ml), which was prepared in Example 4, and allowed to react at ambient temperature for 30 minutes. As a negative control, an IgG antibody (from DAKO Japan Co., Ltd.) from a rabbit which was not immunized was provided and subjected to the same procedure. The osteoclast sample was then washed four times with phosphate-buffered saline containing 1% horse serum, and reacted with a biotinylated goat anti-rabbit IgG antibody (from Vector Laboratories Inc.) used as a secondary antibody at ambient temperature for 30 minutes. It was washed four times with phosphate-buffered saline, and underwent a staining reaction using an ABC-AP kit (from Vector Laboratories Inc.) according to the protocol provided. As a result, the osteoclasts exposed to the anti-DC-STAMP antibody were observed to be stained intensely, which demonstrated that the DC-STAMP was expressed in the neonatal mouse tibia-derived osteoclasts. In contrast, the osteoclasts were not stained at all for the antibody of the negative control.

EXAMPLE 6

Immunostaining in Neonatal Mouse Mandibular Tissue
a) Preparation of Test Sample from Neonatal Mouse Mandibular Tissue A DDY mouse aged 1 day was anesthetized with ether and injected with phosphate-buffered saline (pH 7.4) containing 4% paraformaldehyde into the left ventricle to fix it under perfusion. The mandibule was removed, soaked in phosphate-buffered saline (pH 7.4) containing 4% paraformaldehyde as described above, fixed therein at 4° C. for 12 hours, washed three times with phosphate-buffered saline, and washed further in phosphate-buffered saline at 4° C. overnight. Thereafter, it was decalcified with 10% EDTA (ethylenediaminetetraacetic acid) at 4° C. for a week. It was washed in phosphate-buffered saline containing 30% sucrose at 4° C. overnight, embedded in an OCT compound (from Sakura Finetek Japan Co., Ltd.) and frozen in isopentane containing dry ice. The resultant embedded block was sliced at a 10 μm thickness with a cryomicrotome (Leica Microsystems GmbH) to prepare a mandibular tissue section.

b) Development of DC-STAMP Protein with Immunostaining

The mandibular tissue section prepared in a) was dried in air to remove moisture, and reacted with methanol containing 0.3% hydrogen peroxide at ambient temperature for 30 minutes to eliminate endogenous peroxidase activity. The section was washed three times with phosphate-buffered saline (at ambient temperature for 5 minutes each), and blocked with phosphate-buffered saline containing 10% donkey serum at ambient temperature for 30 minutes. After the blocking solution was removed, the section was immersed in phosphate-buffered saline (with 2% donkey serum) containing the rabbit anti-mouse DC-STAMP polyclonal antibody (10 μg/ml), which was prepared in Example 4, and reacted in a wet chamber at 4° C. overnight. As a negative control, an IgG antibody (from DAKO Japan Co., Ltd.) from a rabbit which was not immunized was provided and subjected to the same procedure. The section was then washed three times with phosphate-buffered saline (at ambient temperature for 5 minutes each), and reacted with a 200-fold dilution with phosphate-buffered saline of a biotinylated donkey anti-rabbit IgG antibody (from Jackson ImmunoResearch Laboratories Inc.) used as a secondary antibody at ambient temperature for 1 hour. It was washed three times with phosphate-buffered saline (at ambient temperature for 5 minutes each), and reacted with a 300-fold dilution with distilled water of a peroxidase-labeled streptavidin conjugate (from DAKO Japan Co., Ltd.) at ambient temperature for 30 minutes. It was washed three times with phosphate-buffered saline (at ambient temperature for 5 minutes each), and underwent a staining reaction by using a DAB substrate kit (from Vector Laboratories Inc.) according to the protocol provided therewith. As a result, the mandibular tissue section that was reacted with the anti-DC-STAMP antibody was observed to be intensely stained only on the osteoclasts, which demonstrated that the DC-STAMP was expressed in the neonatal mouse mandibular-derived osteoclasts. In contrast, none of the cells were stained at all when the antibody of the negative control was used.

EXAMPLE 7

Suppression of Differentiation of RAW-D Cells into Osteoclasts by Using siRNA
a) Preparation of siRNAs Against the Murine DC-STAMP Gene Murine DC-STAMP siRNAs with two uridine units (UU) added on the respective 3'-terminus of sense and antisense chains were prepared by transcription using a Silencer siRNA Construction kit (from Ambion Inc.) according to the protocol provided therewith. Sets of template oligoDNAs needed for preparation of siRNA are described below.

Firstly, a siRNA for the 5' side (corresponding to the 7th transmembrane region in the amino acid sequence predicted from the human DC-STAMP cDNA sequence) of the third exon and a variant siRNA thereof were prepared using the following respective combinations of template oligoDNAs.

siRNA #135 templates:
5'-aatactagga ttgttgtctt ccctgtctc-3' (mDC-STAMP-#135-AS; SEQ ID NO: 16 in the Sequence Listing)
and
5'-aagaagacaa caatcctagt acctgtctc-3' (mDC-STAMP-#135-S; SEQ ID NO: 17 in the Sequence Listing)
variant siRNA #135 templates:
5'-aatactagga gcgttgtctt ccctgtctc-3' (mDC-STAMP-#135-Mut-AS; SEQ ID NO: 18 in the Sequence Listing, where t is mutated to g at nucleotide position 11, and t is mutated to c at nucleotide position 12)
and
5'-aagaagacaa cgctcctagt acctgtctc-3' (mDC-STAMP-#135-Mut-S; SEQ ID NO: 19 in the Sequence Listing, where a is mutated to g at nucleotide position 12, and a is mutated to c at nucleotide position 13)

Secondly, a siRNA for the cDNA sequence portion characteristic of the murine DC-STAMP, which is located on the 3' side of the above siRNA (#135) portion in the third exon, and a variant siRNA thereof were prepared using the following respective combinations of template oligoDNAs.

siRNA *6 templates:
5'-aattctcgtg tcagtctcct tcctgtctc-3' (mDC-STAMP-*6-AS; SEQ ID NO: 20 in the Sequence Listing)
and
5'-aaaaggagac tgacacgaga acctgtctc-3' (mDC-STAMP-*6-S; SEQ ID NO: 21 in the Sequence Listing)
variant siRNA *6 templates:
5'-aattctcgta ccagtctcct tcctgtctc-3' (mDC-STAMP-*6-Mut-AS; SEQ ID NO: 22 in the Sequence Listing, where g is mutated to a at nucleotide position 9, and t is mutated to c at nucleotide position 10)
and
5'-aaaaggagac tggtacgaga acctgtctc-3' (mDC-STAMP-*6-Mut-S; SEQ ID NO: 23 in the Sequence Listing, where a is mutated to g at nucleotide position 13, and c is mutated to t at nucleotide position 14)

b) Suppression of Differentiation of RAW-D Cells into Osteoclasts Using siRNA

Figure 5:
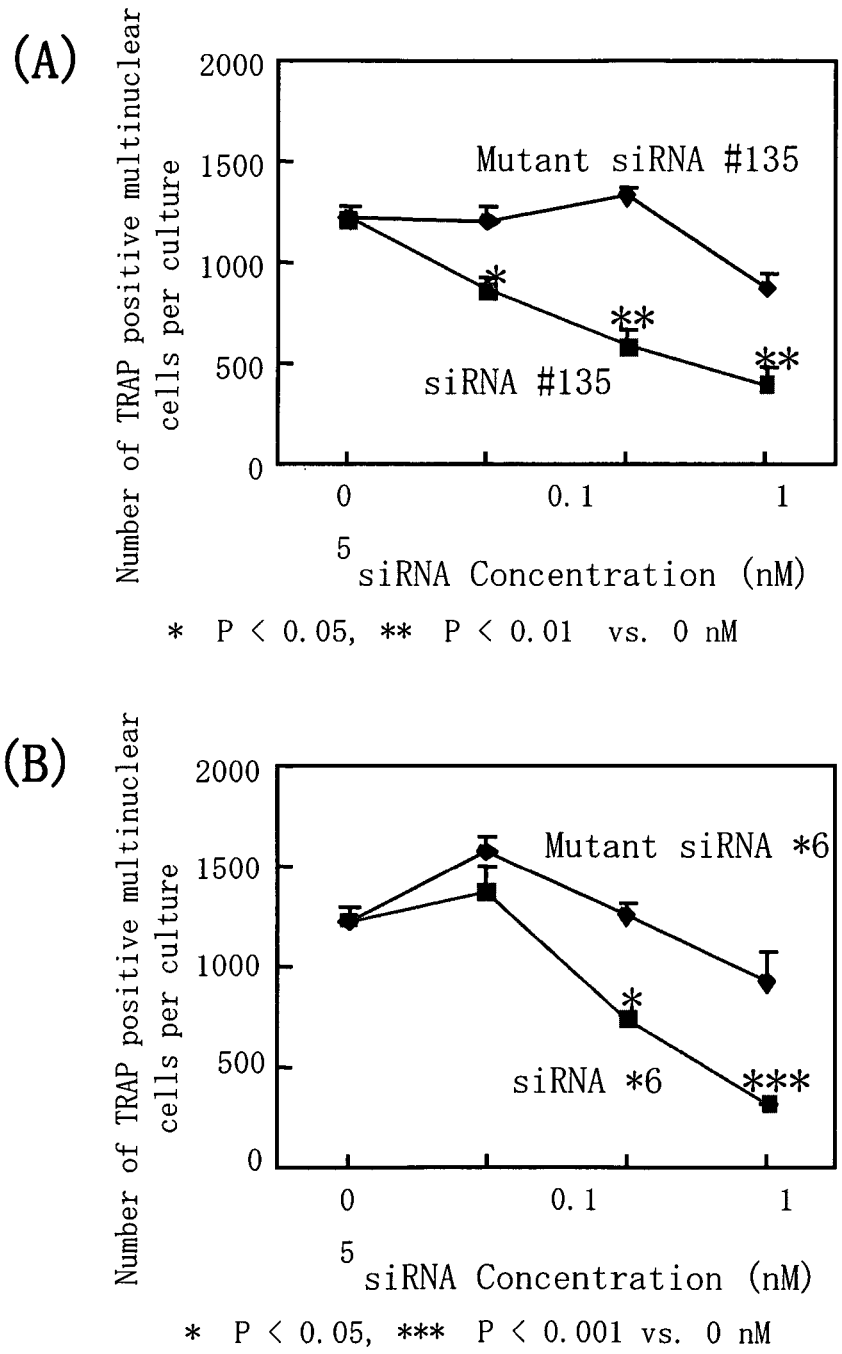
FIG. 5 provides graphs showing lower levels of differentiation of RAW-D cells into osteoclasts caused by siRNAs against DC-STAMP.

RAW-D was prepared at $4.5 \times 10^4$ cells/ml in α-MEM medium containing 10% fetal calf serum. The preparation was plated on a 96-well plate at 80 μl/well. On the next day, the medium was replaced with 80 µl of OPTI-MEM I medium (from Invitrogen Corporation), to which was added the DC-STAMP siRNA or variant siRNA prepared in a) to a final concentration of 0.1, 1 or 5 nM, and the cells were transfected using a transfection reagent, siPORT Lipid (from Ambion Inc.) according to the protocol provided therewith (20 µl added). A control (mock) free of siRNA but containing the transfection reagent was also provided. The cells were transfected in a $CO_2$ incubator for 4 hours, and then the following were added: 100 µl of α-MEM medium containing the human RANKL (from PeproTech Inc.) at 40 ng/ml, the human TNF-α (from PeproTech Inc.) at 2 ng/ml and 20% fetal calf serum. The cells were cultured for 3 days and then stained for TRAP with a Leukocyte Acid Phosphatase kit (from Sigma Co.) according to the protocol provided to count the number of TRAP positive multinuclear osteoclasts formed from the cells. The DC-STAMP siRNA #135 at a concentrations of 0.1, 1 or 5 nM was observed to suppress significantly the formation of osteoclasts, this was not the case when the variant siRNA #135 was added. The variant siRNA at a concentration of 5 nM was observed to suppress slightly the formation of osteoclasts, but no suppression of osteoclastic formation was observed at a concentration of 0.1 or 1 nM. From the results, the DC-STAMP siRNA suppressed formation of TRAP positive multinuclear osteoclasts which may be induced in RAW-D by RANKL and TNF-α depending on its concentration, in contrast to the mock control (siRNA level=0 nM) and a negative control, i.e., the variant siRNA (FIGS. 5A and 5B). As described above, when expression of the DC-STAMP gene was suppressed by the siRNA, differentiation of RAW-D into osteoclasts was suppressed, which suggested that DC-STAMP is an essential factor for differentiation into osteoclasts.

EXAMPLE 8

Isolation of an Open Reading Frame (ORF) cDNA Clone for Murine DC-STAMP a) Extraction of Total RNA from RAW-D RAW-D was prepared at $7 \times 10^4$ cells/ml in α-MEM medium containing 10% fetal calf serum. The preparation was plated on a 24-well plate at 500 µl/well, and the following were added: human RANKL (from PeproTech Inc.) to a final concentration of 20 ng/ml, human TNF-α (from PeproTech Inc.) to a final concentration of 2 ng/ml and murine MIP-1α (from PeproTech Inc.) to a final concentration of 1 ng/ml, and then cultured for 3 days.

Then, the total RNA was extracted from RAW-D using a total RNA extraction reagent (TRIZol reagent from Invitrogen Corporation) according to the protocol provided therewith. The total RNA recovered was stored at −80° C.

b) Synthesis of the First Strand cDNA

The total RNA (1 µg) and 1 µl of oligo(dT) 18 primer (0.5 µg/µl) were added to $H_2O$ to make a 11 µl solution, which was then heated at 70° C. for 10 minutes and stored at 4° C. To the solution were added: 4 µl of 5×1st Strand Buffer (from Invitrogen Corporation), 1 µl of 10 mM dNTPs, 2 µl of 0.1 M dithiothreitol, 1 µl of Superscript II reverse transcriptase (200 U/µl from Invitrogen Corporation), and 1 µl of $H_2O$ to make a total 20 µl solution, which underwent the reaction at 42° C. for 1 hour, was then heated at 70° C. for 10 minutes and stored at 4° C.

c) PCR Reaction

Oligonucleotides, as primers for amplifying the ORF cDNAs of murine DC-STAMP and murine DC-STAMP ΔT7 by PCR, and having the sequences:

5'-tttgtcgaca tgaggctctg gaccttgggc accagtattt t-3'
(mDC-STAMP-cDNA-F: SEQ ID NO: 24 in the Sequence Listing)

and

5'-tttgcggccg ctcatagatc atcttcattt gcagggattg t-3'
(mDC-STAMP-cDNA-R: SEQ ID NO: 25 in the Sequence Listing)

were synthesized as usual. This combination of the primers was used for PCR, which was conducted under the conditions described below using a thermal cycler (GeneAmp PCR System 9700). To redistilled water were added primers (final concentration of 1.0 µM each), 5 µl of 10× Pyrobest PCR buffer (from Takara Shuzo Co., Ltd.), 4 µl of 2.5 mM dNTPs, and 1 µl of cDNA (prepared in b)) to make a 50 µl solution. Further, 0.5 µl of a Pyrobest DNA polymerase (5 U/µl) (from Takara Shuzo Co., Ltd.) was added to make the reaction solution. The reaction solution was heated at 94° C. for 2 minutes, treated repeatedly 30 times with a temperature cycle of 94° C. for 0.5 minutes, 60° C. for 0.5 minutes, and 72° C. for 5 minutes, then heated at 72° C. for 10 minutes and stored at 4° C.

d) Cloning into the pCI-neo Vector

The whole PCR reaction solution obtained in c) was purified using a QIAquick PCR Purification Kit (from Qiagen Inc.) according to the protocol provided therewith. The resultant fragment was digested with restriction enzymes SalI and NotI, ligated to pCI-neo (from Promega Corporation) preliminarily digested also with SalI and NotI using a DNA Ligation Kit Ver. 1 (from Takara Shuzo Co., Ltd.), and transformed into *E. coli* XL1-Blue MRF'(from Stratagene Corporation). Transformed *E. coli* having the plasmid pCI-neo-murine DC-STAMP were isolated from the *E. coli* colonies thus obtained.

Analysis of the entire nucleotide sequence of the ORF cDNA inserted in the resulting plasmid using a DNA sequencer (ABI Prism 310 DNA sequencer from Applied Biosystems Division, PerkinElmer Japan Co., Ltd.) revealed that the sequence was a sequence shown in SEQ ID NO: 26 in the Sequence Listing. This nucleotide sequence was identical to the ORF coding region in the sequence registered as "murine DC-STAMP" (Accession No. AB109560) with the NCBI GeneBank data base, and the amino acid sequence (SEQ ID NO: 27 in the Sequence Listing) encoded by the nucleotide sequence was 100% identical to the amino acid sequence of the murine DC-STAMP.

EXAMPLE 9

Effect of Over-Expression of Murine DC-STAMP Protein on Differentiation of RAW-D Cells into Osteoclasts In the pCI-neo-murine DC-STAMP plasmid obtained in Example 8, the open reading frame sequence for the murine DC-STAMP is integrated under the control of the CMV promoter derived from pCI-neo. Therefore, transfer of the plasmid into a host may induce the expression of the murine DC-STAMP protein.

The gene transfer (transient transfection) of this expression plasmid into RAW-D was carried out by the DEAE-dextran process.

This pCI-neo-murine DC-STAMP vector (3 µg) or a pCI-neo vector (3 µg) without any the DNA insert was combined with a mixture of 50 µl of a DEAE-dextran solution (from Promega Corporation) at 10 mg/ml and 950 µl of OPTI-MEMI (from Invitrogen Corporation) to make a transfection solution.

Figure 6:
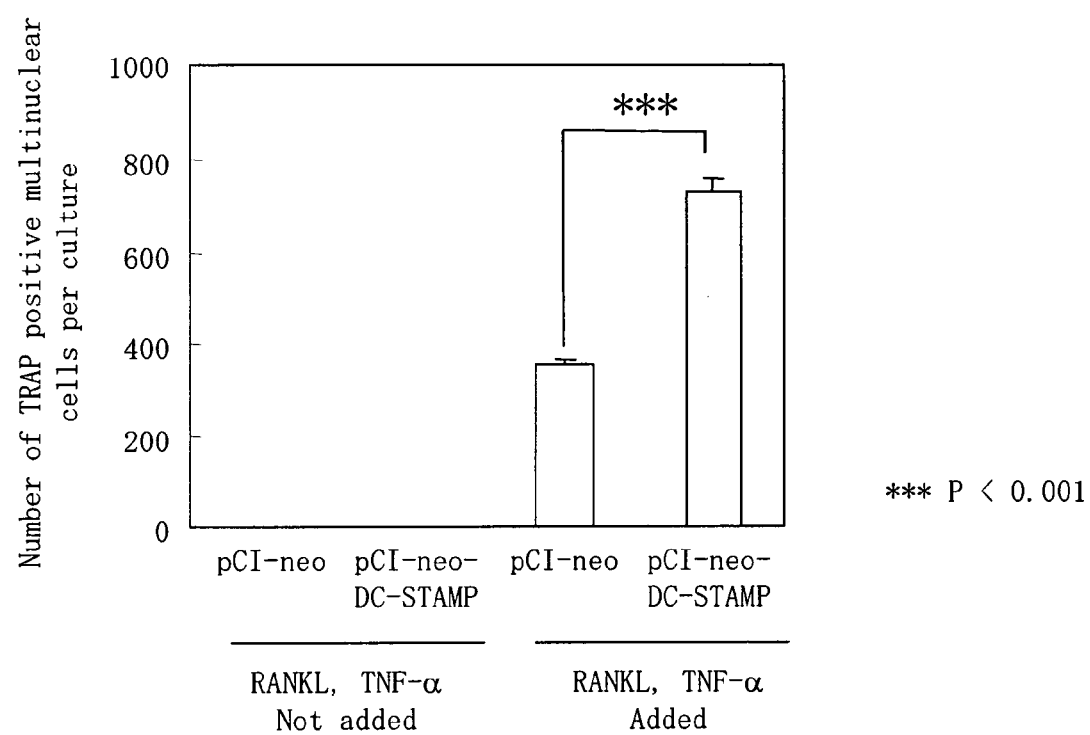
FIG. 6 is a graph showing enhanced formation of osteoclasts from RAW-D cells due to forced expression of DC-STAMP protein.

RAW-D ($3.0 \times 10^6$ cells) were washed (centrifuged at 200×g for 5 minutes) twice with serum-free α-MEM (10 ml) and suspended in the transfection solution (1 ml) described above. The suspension was kept at a constant temperature in a $CO_2$ incubator (at 37° C.) for 30 minutes, washed (centrifuged under 200×g for 5 minutes) once with serum-free α-MEM (10 ml), and further washed once with α-MEM containing 5% fetal calf serum (10 ml). The suspended wash was centrifuged at 200×g for 10 minutes to precipitate the cells, which were then re-suspended in A-MEM containing 10% fetal calf serum (2 ml). The cell density was measured with a hemocytometer and adjusted to $4.5 \times 10^4$ cells/ml. The resultant suspension was plated on a 96-well plate at 0.15 ml/well, and the following were added: human RANKL (from PeproTech Inc.) to a final concentration of 20 ng/ml and human TNF-α (from PeproTech Inc.) to a final concentration of 1 ng/ml, or, alternatively, neither of these were added. The cells were cultured for 3 days and then stained for TRAP with a Leukocyte Acid Phosphatase kit (from Sigma Co.) according to the protocol provided herewith to count the number of TRAP positive multinuclear osteoclasts derived therefrom. As a result, in the absence of RANKL and TNF-α, no formation of TRAP positive multinuclear osteoclasts was induced, even when the murine DC-STAMP protein was over-expressed, but, in the presence of RANKL and TNF-α, over-expression of the murine DC-STAMP protein enhanced significantly formation of the TRAP positive multinuclear osteoclasts, compared with the control, i.e., when RAW-D was transfected with the pCI-neo vector without the DNA insert (FIG. 6). Consequently, DC-STAMP was suggested to be a factor for enhancing differentiation into osteoclasts.

EXAMPLE 10

Effect of Addition of Anti-Murine DC-STAMP Polyclonal Antibody on Differentiation of RAW-D Cells into Osteoclasts The rabbit anti-murine DC-STAMP polyclonal antibody prepared in Example 4 was used to examine its effect on differentiation of RAW-D cells into osteoclasts.

Figure 7:
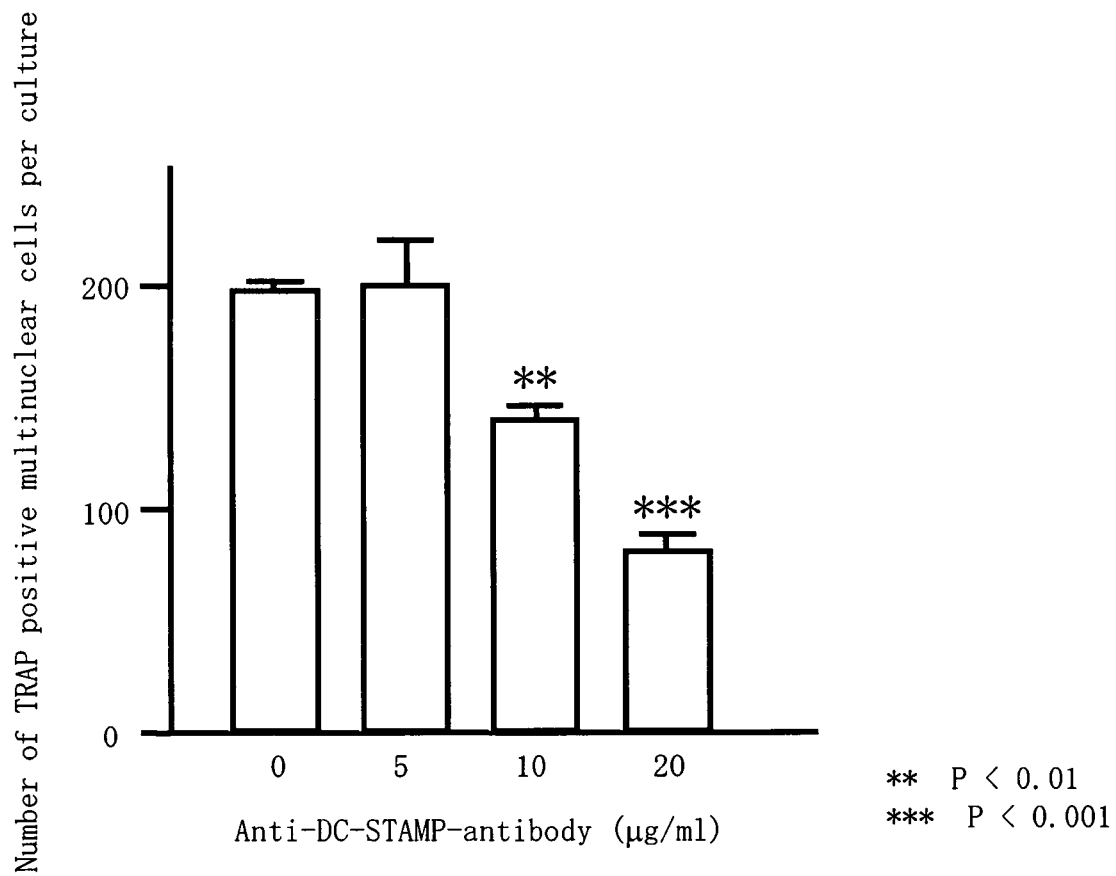
FIG. 7 is a graph showing suppressed formation of osteoclasts from RAW-D cells due to an anti-DC-STAMP antibody.

RAW-D was prepared at $4.5 \times 10^4$ cells/ml in α-MEM medium containing 10% fetal calf serum. The suspension was plated on a 96-well plate at 150 µL/well, and the following were added: human RANKL (from PeproTech Inc.) to a final concentration of 20 ng/ml and human TNF-α (from PeproTech Inc.) to a final concentration of 1 ng/ml. To the cell culture supernatant, the rabbit anti-murine DC-STAMP polyclonal antibody prepared in Example 4 was added to a final concentration of 0, 5, 10 or 20 µg/ml. The cells were cultured for 3 days and then stained for TRAP with a Leukocyte Acid Phosphatase kit (from Sigma Co.) according to the protocol provided therewith to count the number of TRAP positive multinuclear osteoclasts derived therefrom. As a result, formation of the TRAP positive multinuclear osteoclasts was suppressed by addition of anti-murine DC-STAMP polyclonal antibody in a dose-dependent manner (FIG. 7). Addition of anti-murine DC-STAMP polyclonal antibody at a level of 10 µg/ml or more suppressed significantly formation of the osteoclasts compared with the case when no antibody was added.

The results indicate that the antibody potentially capable of specifically binding to DC-STAMP and DC-STAMP ΔT7 suppressed formation of the TRAP positive multinuclear osteoclasts from RAW-D, and thus DC-STAMP and DC-STAMP ΔT7 were suggested to be very important in differentiation into osteoclasts.

EXAMPLE 11

Figure 8:
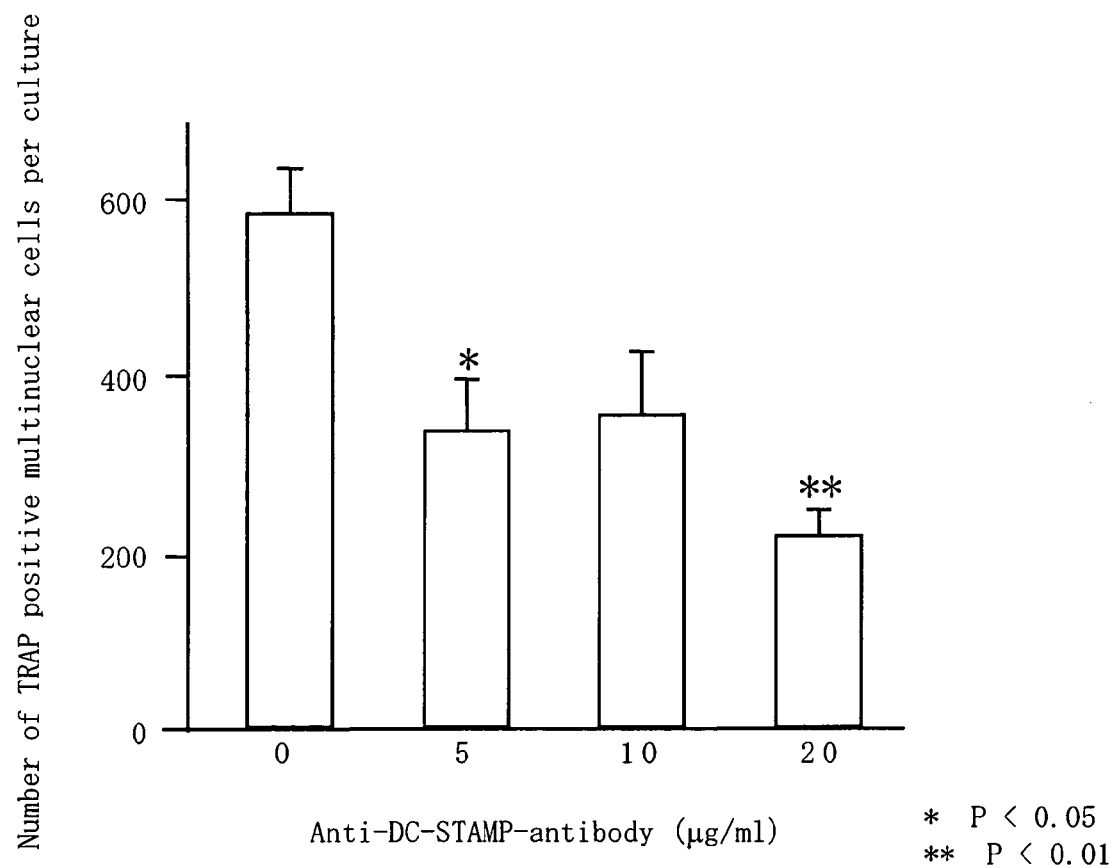
FIG. 8 is a graph showing suppressed formation of osteoclasts from murine bone marrow cells due to an anti-DC-STAMP antibody.

Effect of Addition of Anti-Murine DC-STAMP Polyclonal Antibody on Differentiation of Murine Bone Marrow-Derived Primary Culture Cells into Osteoclasts A male DDY mouse aged 6 weeks was euthanized by cervical dislocation under ether anesthesia to remove the femur and tibia. The femur and tibia were stripped of soft tissues and cut on both ends, respectively. A serum-free α-MEM medium was infused into the bone marrow using a syringe with a 25-gauge needle to collect bone marrow cells. The cell number was counted, and the cells were prepared at $2 \times 10^6$ cells/ml in α-MEM medium containing 15% fetal calf serum. The cell suspension was plated on a 24-well plate at 500 µl/well, and activated vitamin $D_3$ was added (from Biomol Corporation) to a final concentration of $1 \times 10^{-8}$ M. To the cell culture supernatant, the rabbit anti-murine DC-STAMP polyclonal antibody prepared in Example 4 was added to a final concentration of 0, 5, 10 or 20 µg/ml. The cells were cultured for 6 days and then stained for TRAP with a Leukocyte Acid Phosphatase kit (from Sigma Co.) according to the protocol provided therewith to count the number of TRAP positive multinuclear osteoclasts derived therefrom. As a result, formation of the TRAP positive multinuclear osteoclasts was suppressed by addition of the anti-murine DC-STAMP polyclonal antibody in a dose-dependent manner (FIG. 8). Addition of the anti-murine DC-STAMP polyclonal antibody at a level of 5 µg/ml or 20 µg/ml suppressed significantly osteoclastic formation compared with the case in which there was no addition of the antibody. The results indicate that the antibody capable of specifically binding to DC-STAMP and DC-STAMP ΔT7 suppressed formation of the TRAP positive multinuclear osteoclasts from murine bone marrow cells, and it has been thus demonstrated that DC-STAMP and DC-STAMP ΔT7 are involved in differentiation of primary culture cells, which are more analogous to those of the living body, as well as cell strains such as RAW-D into osteoclasts.

EXAMPLE 12

Effect of Addition of Anti-Murine DC-STAMP Polyclonal Antibody on Formation of Bone Resorption Pit When cells derived from murine femur and tibia are cultured on an ivory section in the presence of activated vitamin $D_3$, osteoclasts are observed to erode the ivory surface with many pits of bone resorption widely distributed (Takada et al., Bone and Mineral, 17, 347-359 (1992)).

Figure 9:
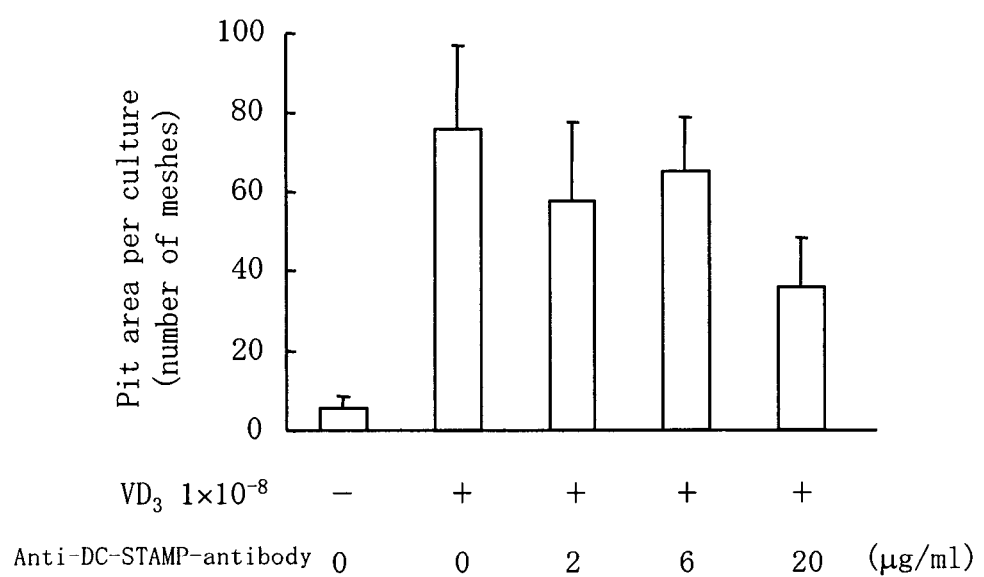
FIG. 9 is a graph showing suppressed formation of resorption cavities due to an anti-DC-STAMP antibody.

An ICR mouse aged 14 days (either sex may be used) was euthanized by cervical dislocation under ether anesthesia to remove femur and tibia. The femur and tibia were stripped of soft tissues and minced finely using scissors in a dish 60 mm in diameter containing 1 ml of DMEM medium with 10% fetal calf serum. The minced sample was transferred into a 15-ml centrifuge tube, to which was added 10 ml of DMEM medium containing 10% fetal calf serum, agitated for 30 seconds in a vortex mixer (from M & S Instruments Inc.) and left to stand for 2 minutes. The supernatant was recovered and the cell number was counted. A cell suspension was prepared at $1 \times 10^7$ cells/ml in DMEM medium containing 10% fetal calf serum. The suspension was plated on a 96-well plate at 100 μl/well on which ivory sections of 150-200 μm in thickness and 6 mm in diameter (prepared in Kureha Chemical Industry Co., Ltd.) were laid, and cultured for 4 hours in a $CO_2$ incubator. Thereafter, the medium was replaced by 200 μl of DMEM medium containing 10% fetal calf serum, to which activated vitamin $D_3$ was added to a final concentration of $1\times10^{-8}$ M (a group without the vitamin was also provided). To the cell culture supernatant, the rabbit anti-murine DC-STAMP polyclonal antibody prepared in Example 4 was added to a final concentration of 0, 2, 6 or 20 μg/ml. The cells were cultured for 4 days. After the culture was finished, the culture supernatant was removed from the plate containing the ivories. The plate was washed once with distilled water, and another portion of distilled water was added. The cells attached on each ivory section were removed with a polishing brush (from Tagaya Seisakusho Co., Ltd.) connected to a hand motor (from Tokyo Nakai Co., Ltd.). The ivory section was washed twice with distilled water, stained with acid hematoxylin solution (from Sigma Co.) for 13 minutes on the pits formed on its surface, and washed twice with distilled water. The ivory section was reversed and the area of the pits was measured microscopically. To measure the total area of the pits, a micrometer (10×10 squares) attached to the eye lens of the microscope was used to count the total number of squares (meshes) where pits were located and convert the number to the pit area. As a result, addition of activated vitamin $D_3$ induced formation of many pits on the ivory section, but when the anti-murine DC-STAMP polyclonal antibody was added at the same time, pit formation was suppressed by the antibody in a dose-dependent manner (FIG. 9). The results indicate that the antibody potentially capable of specifically binding to DC-STAMP and DC-STAMP ΔT7 suppressed pit formation induced by osteoclasts from murine femur and tibia, and thus DC-STAMP and DC-STAMP ΔT7 were suggested to be involved also in regulation of bone resorption by osteoclasts.

EXAMPLE 13

Expression of Human DC-STAMP Gene in Giant Cell Tumor Tissue

Giant cell tumor (GCT) is a bone tumor, characterized by osteolytic bone destruction as a clinical symptom, in which a large number of multinuclear giant cells occur that are osteoclastic histologically, (Bullough et al., Atlas of Orthopedic Pathology 2nd edition, 17.6-17.8, Lippincott Williams & Wilkins Publishers (1992)). The EST probe (Affymetrix Genechip HG-U133 probe 221266_s_at, made by Affymetrix), which has a nucleotide sequence partially overlapping with the human DC-STAMP gene, was analyzed for expression profile in GCT tissues using the data base (Genesis 2003 Release 2.0) made by GeneLogic. EST probes for RANK (Affymetrix Genechip HG-U133 probe 207037_at, made by Affymetrix) and RANKL (Affymetrix Genechip HG-U133 probe 210643_at, made by Affymetrix) which play a key role in differentiation into osteoclasts, and for cathepsin K (Affymetrix Genechip HG-U133 probe 202450_s_at, made by Affymetrix) and TRAP (Affymetrix Genechip HG-U133 probe 204638_at, made by Affymetrix) which are markers for differentiation into osteoclasts, were also analyzed for expression profile in GCT tissues.

Figure 11:
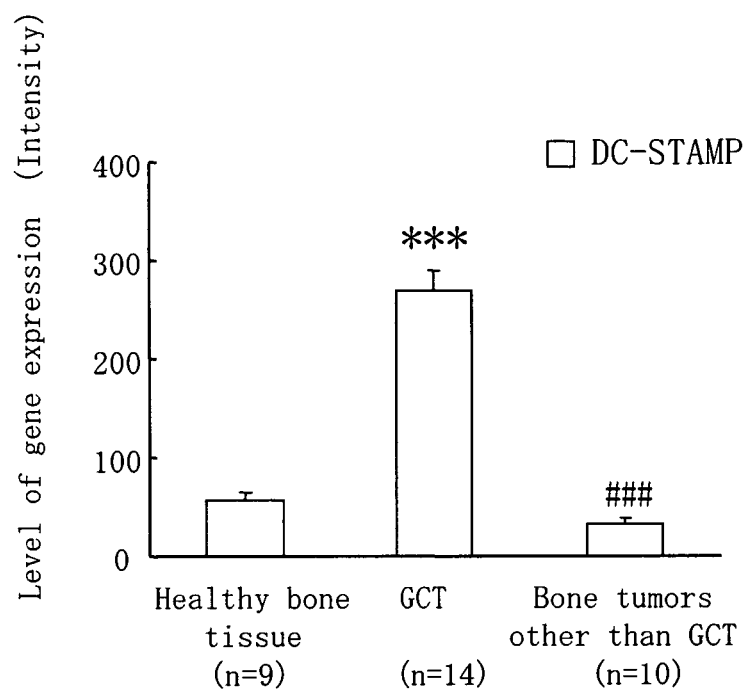
FIG. 11 is a graph showing an expression profile of human DC-STAMP gene in giant cell tumor.

A comparison of the expression levels was made among 9 cases of healthy bone tissues, 14 cases of GCT tissues and 10 cases of bone tumor tissues other than GCT: this revealed that the GCT tissues specifically had a higher level of transcription of RANK and RANKL than the healthy bone tissues (FIG. 10A). In contrast, the bone tumor tissues other than GCT, which may not always enhance bone resorption, had a significantly lower level of transcription of RANK and RANKL than the GCT, and a comparable level of the expression to that of the healthy bone tissues. Accordingly, GCT was suggested to provide an environment which may enhance formation and activation of osteoclasts. Comparison of the expression levels of cathepsin K and TRAP revealed that transcription of these factors was significantly higher in the GCT (FIG. 10B), which suggested that many bone-resorbing osteoclasts might appear in the GCT. A similar comparison of the expression level of DC-STAMP revealed that DC-STAMP was specifically transcribed at a higher level in the GCT than RANK, RANKL, cathepsin K and TRAP (FIG. 11). From these findings, DC-STAMP was suggested to be involved also in human conditions such as GCT which enhance bone resorption.

EXAMPLE 14

Figure 12:
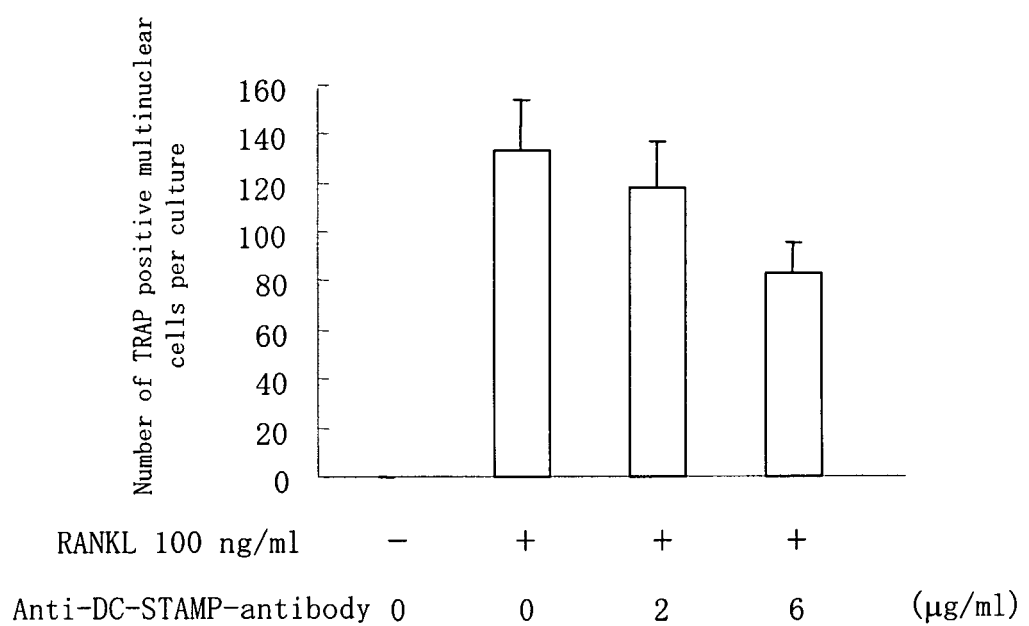
FIG. 12 is a graph showing suppressed formation of osteoclasts from human peripheral blood mononuclear cells due to an anti-DC-STAMP antibody.

Effect of Addition of Anti-murine DC-STAMP Polyclonal Antibody on Formation of Human Osteoclasts When human peripheral blood mononuclear cells (HPBMC) are stimulated with RANKL in the presence of M-CSF and dexamethasone, TRAP positive multinuclear osteoclasts are formed (Matsuzaki et al., Biochem. Biophys. Res. Commun., (1998) 246, 199-204). HPBMCs purchased from Takara Bio Inc. were prepared at $5\times10^6$ cells/ml in α-MEM medium containing 10% fetal calf serum. The cells were plated on a 96-well plate at 100 μl/well, and to which was added a medium containing human M-CSF (from R & D Systems Inc.) to a final concentration of 200 ng/ml, dexamethasone (from Wako Pure Chemical Industries, Ltd.) to a final concentration of $1\times10^{-7}$ M and human RANKL (from PeproTech Inc.) to a final concentration of 100 ng/ml to 200 μl/well. A non-RANKL group of the cell suspensions was also provided. To the cell culture supernatant, the rabbit anti-murine DC-STAMP polyclonal antibody prepared in Example 4 was added to a final concentration of 0, 2 or 6 μg/ml. After the culture was initiated, on days 4, 7 and 11, the medium was replaced and a test sample was added, and on day 13, the cells were stained for TRAP with a Leukocyte Acid Phosphatase kit (from Sigma Co.) according to the protocol provided therewith to count the number of TRAP positive multinuclear osteoclasts formed. As a result, a large number of osteoclasts were formed by stimulation with RANKL, but addition of the anti-murine DC-STAMP polyclonal antibody suppressed formation of the TRAP positive multinuclear osteoclasts in a dose-dependent manner (FIG. 12). The results indicate that the anti-murine DC-STAMP antibody suppressed formation of the TRAP positive multinuclear osteoclasts from HPBMC, and thus DC-STAMP was strongly suggested to be involved in differentiation into osteoclasts in humans as well as in mice.

Industrial Applicability

According to the present invention, preventive and/or therapeutic agents for metabolic bone disorders can be obtained through the mechanism of action of inhibiting osteoclastic activity.

The invention claimed is:

1. A purified monoclonal antibody capable of binding to at least one human or murine dendritic cell specific transmembrane protein (DC-STAMP) selected from the group consisting of: a protein comprising the amino acid sequence of SEQ ID NO: 2, and a protein comprising the amino acid sequence of SEQ ID NO: 4, and suppressing formation of osteoclasts derived from murine bone marrow cells or suppressing formation of osteoclasts derived from human peripheral blood mononuclear cells, wherein the monoclonal antibody binds in the region of amino acid residues 330-343 of SEQ ID NO: 2 or in the region of amino acid residues 330-343 of SEQ ID NO: 4.

2. The purified antibody according to claim 1, wherein the antibody is humanized.

3. The purified antibody according to claim 1, wherein the antibody is a complete human antibody.

4. The purified antibody according to claim 1, wherein the antibody is an IgG antibody.

5. The purified antibody according to claim 1, wherein the antibody suppresses formation of osteoclasts derived from murine bone marrow cells at a concentration between 5 and 20 μg/ml.

6. The purified antibody according to claim 1, wherein the antibody suppresses formation of osteoclasts derived from human peripheral blood mononuclear cells at a concentration between 2 and 6 μg/ml.

7. A kit for detecting a metabolic bone disorder associated with an abnormal level of the DC-STAMP, comprising: (1)

the purified antibody according to claim 1; and (2) a secondary antibody capable of binding to the antibody of (1).

8. A pharmaceutical composition for treatment of a metabolic bone disorder associated with an increased level of DC-STAMP, wherein the pharmaceutical composition comprises an antibody according to claim 1.

9. The pharmaceutical composition according to claim 8, wherein the metabolic bone disorder is osteoporosis, rheumatoid arthritis or cancerous hypercalcemia.

10. The pharmaceutical composition according to claim 8, wherein the metabolic bone disorder is osteoporosis.

11. The pharmaceutical composition according to claim 8, wherein the metabolic bone disorder is rheumatoid arthritis.

12. The pharmaceutical composition according to claim 8, wherein the metabolic bone disorder is cancerous hypercalcemia.

13. A pharmaceutical composition for treatment of a metabolic bone disorder associated with an increased level of DC-STAMP, wherein the pharmaceutical composition comprises an antibody according to claim 1 and at least one component selected from the group consisting of: bisphosphonates, activated vitamin $D_3$, calcitonin and its derivatives, estradiol, SERMs (selective estrogen receptor modulators), ipriflavone, vitamin $K_2$ (menatetrenone), calcium preparations, PTH (parathyroid hormone) preparations, non-steroidal anti-inflammatory agents, anti-TNFα (tumor necrosis factor α) antibodies, anti-PTHrP (parathyroid hormone-related protein) antibodies, IL-1 (interleukin 1) receptor antagonists, anti-RANKL (receptor activator of nuclear factor kappa-B ligand) antibodies and OCIF (osteoclastogenesis inhibitory factor).

\* \* \* \* \*

SEQUENCE LISTING

<160> NUMBER OF SEQ ID NOS: 27

<210> SEQ ID NO 1
<211> LENGTH: 1952
<212> TYPE: DNA
<213> ORGANISM: Homo sapiens
<220> FEATURE:
<221> NAME/KEY: CDS
<222> LOCATION: (50)..(1462)

<400> SEQUENCE: 1

```
gcatttctgc attcgaagaa gaatctgaga gaaacctgac gcagggagc atg ggt atc      58
                                                    Met Gly Ile
                                                      1 tgg acc tca ggc act gat atc ttc cta agt ctt tgg gag att tac gtg     106
Trp Thr Ser Gly Thr Asp Ile Phe Leu Ser Leu Trp Glu Ile Tyr Val
  5                  10                  15 tct cca aga agc ccc gga tgg atg gac ttt atc cag cat ttg gga gtt     154
Ser Pro Arg Ser Pro Gly Trp Met Asp Phe Ile Gln His Leu Gly Val
 20                  25                  30                  35 tgc tgt ttg gtt gct ctt att tca gtg ggc ctc ctg tct gtg gcc gcc     202
Cys Cys Leu Val Ala Leu Ile Ser Val Gly Leu Leu Ser Val Ala Ala
                 40                  45                  50 tgc tgg ttt ctg cca tca atc ata gcg gcc gct gcc tcc tgg att atc     250
Cys Trp Phe Leu Pro Ser Ile Ile Ala Ala Ala Ala Ser Trp Ile Ile
         55                  60                  65 acg tgt gtt ctg ctg tgt tgc tcc aag cat gca cga tgt ttt att ctt     298
Thr Cys Val Leu Leu Cys Cys Ser Lys His Ala Arg Cys Phe Ile Leu
 70                  75                  80 ctt gtc ttt ctc tct tgt ggc ctg cgt gaa ggc agg aat gct ttg att     346
Leu Val Phe Leu Ser Cys Gly Leu Arg Glu Gly Arg Asn Ala Leu Ile
         85                  90                  95 gca gct ggc aca ggg atc gtc atc ttg gga cac gta gaa aat att ttt     394
Ala Ala Gly Thr Gly Ile Val Ile Leu Gly His Val Glu Asn Ile Phe
100                 105                 110                 115 cac aac ttt aaa ggt ctc cta gat ggt atg act tgc aac cta agg gca     442
His Asn Phe Lys Gly Leu Leu Asp Gly Met Thr Cys Asn Leu Arg Ala
                120                 125                 130 aag agc ttt tcc ata cat ttt cca ctt ttg aaa aaa tat att gag gca     490
Lys Ser Phe Ser Ile His Phe Pro Leu Leu Lys Lys Tyr Ile Glu Ala
        135                 140                 145 att cag tgg att tat ggc ctt gcc act cca cta agt gta ttt gat gac     538
Ile Gln Trp Ile Tyr Gly Leu Ala Thr Pro Leu Ser Val Phe Asp Asp
    150                 155                 160 ctt gtt tct tgg aac cag acc ctg gca gtc tct ctt ttc agt ccc agc     586
Leu Val Ser Trp Asn Gln Thr Leu Ala Val Ser Leu Phe Ser Pro Ser
165                 170                 175 cat gtc ctg gag gca cag cta aat gac agc aaa ggg gaa gtc ctg agc     634
His Val Leu Glu Ala Gln Leu Asn Asp Ser Lys Gly Glu Val Leu Ser
180                 185                 190                 195 gtc ttg tac cag atg gca aca acc aca gag gtg ttg tcc tcc ctg ggt     682
Val Leu Tyr Gln Met Ala Thr Thr Thr Glu Val Leu Ser Ser Leu Gly
                200                 205                 210 cag aag cta ctt gcc ttt gca ggg ctt tcg ctc gtc ctg ctt ggc act     730
Gln Lys Leu Leu Ala Phe Ala Gly Leu Ser Leu Val Leu Leu Gly Thr
        215                 220                 225 ggc ctc ttc atg aag cga ttt ttg ggc cct tgt ggt tgg aag tat gaa     778
Gly Leu Phe Met Lys Arg Phe Leu Gly Pro Cys Gly Trp Lys Tyr Glu
    230                 235                 240 aac atc tac atc acc aga caa ttt gtt cag ttt gat gaa agg gag aga     826
Asn Ile Tyr Ile Thr Arg Gln Phe Val Gln Phe Asp Glu Arg Glu Arg
```

```
cat caa cag agg ccc tgt gtg ctc ccg ctg aat aag gag gaa agg agg      874
His Gln Gln Arg Pro Cys Val Leu Pro Leu Asn Lys Glu Glu Arg Arg
260                 265                 270                 275 aag tat gtc atc atc ccg act ttc tgg ccg act cct aaa gaa agg aaa      922
Lys Tyr Val Ile Ile Pro Thr Phe Trp Pro Thr Pro Lys Glu Arg Lys
                280                 285                 290 aac ctg ggg ctg ttt ttc ctc ccc ata ctt atc cat ctc tgc atc tgg      970
Asn Leu Gly Leu Phe Phe Leu Pro Ile Leu Ile His Leu Cys Ile Trp
            295                 300                 305 gtg ctg ttt gca gct gta gat tat ctg ctg tat cgg ctc att ttc tca     1018
Val Leu Phe Ala Ala Val Asp Tyr Leu Leu Tyr Arg Leu Ile Phe Ser
        310                 315                 320 gtg agc aag cag ttt caa agc ttg cca ggg ttt gag gtt cac ttg aaa     1066
Val Ser Lys Gln Phe Gln Ser Leu Pro Gly Phe Glu Val His Leu Lys
    325                 330                 335 ctg cac gga gag aaa caa gga act caa gat att atc cat gat tct tcc     1114
Leu His Gly Glu Lys Gln Gly Thr Gln Asp Ile Ile His Asp Ser Ser
340                 345                 350                 355 ttt aat ata tct gtg ttt gaa ccc aac tgt atc cca aaa cca aaa ttc     1162
Phe Asn Ile Ser Val Phe Glu Pro Asn Cys Ile Pro Lys Pro Lys Phe
                360                 365                 370 ctt cta tct gag acc tgg gtt cct ctc agt gtt att ctt ttg ata tta     1210
Leu Leu Ser Glu Thr Trp Val Pro Leu Ser Val Ile Leu Leu Ile Leu
            375                 380                 385 gtg atg ctg gga ctg ttg tcc tct atc ctt atg caa ctt aaa atc ctg     1258
Val Met Leu Gly Leu Leu Ser Ser Ile Leu Met Gln Leu Lys Ile Leu
        390                 395                 400 gtg tca gca tct ttc tac ccc agc gtg gag agg aag cgc atc caa tat     1306
Val Ser Ala Ser Phe Tyr Pro Ser Val Glu Arg Lys Arg Ile Gln Tyr
    405                 410                 415 ctg cat gca aag ctg ctt aaa aaa aga tca aag cag ccg ctg gga gaa     1354
Leu His Ala Lys Leu Leu Lys Lys Arg Ser Lys Gln Pro Leu Gly Glu
420                 425                 430                 435 gtc aaa aga cgg ctg agt ctc tat ctt aca aag att cat ttc tgg ctt     1402
Val Lys Arg Arg Leu Ser Leu Tyr Leu Thr Lys Ile His Phe Trp Leu
                440                 445                 450 cca gtc ctg aaa atg att agg aag aag caa atg gac atg gca agt gca     1450
Pro Val Leu Lys Met Ile Arg Lys Lys Gln Met Asp Met Ala Ser Ala
            455                 460                 465 gac aag tca tga gagaccccga ctactcctca gccacatcgc accaacaatt        1502
Asp Lys Ser
        470 ctcttcaggt ctaggatggc agtcactatt catgccggat aatagagaac tatgtgacgc   1562 agtcctctca ggagtctgag tttacagagc aacttgcag cacctggtta tgcctccttt    1622 catctcaaag ccaaagagct gccaggtaaa tggttatgtg gtctatgttc caaacaaacc   1682 acatgatctt gcctgtgtca caatgtaaca agactctagc tgggtcccct ggtgatgagt   1742 ttcagcatag aataatgttc aaggaaaaga aaacgaaaac agtttaaatc tctaccacag   1802 cctcacaagc aaatgctaag gggaacatac atgtaaaaag ccagcaaact atcttcaaac   1862 tcttccgtcc ttaatgtctt ccatggctat tgcccccaca atggtctctt ttctccctgc   1922 tcccttatta aagaactctt tctgaaaccc                                    1952

<210> SEQ ID NO 2
<211> LENGTH: 470
<212> TYPE: PRT
<213> ORGANISM: Homo sapiens
```

<400> SEQUENCE: 2

```
Met Gly Ile Trp Thr Ser Gly Thr Asp Ile Phe Leu Ser Leu Trp Glu
1               5                   10                  15

Ile Tyr Val Ser Pro Arg Ser Pro Gly Trp Met Asp Phe Ile Gln His
            20                  25                  30

Leu Gly Val Cys Cys Leu Val Ala Leu Ile Ser Val Gly Leu Leu Ser
        35                  40                  45

Val Ala Ala Cys Trp Phe Leu Pro Ser Ile Ile Ala Ala Ala Ala Ser
    50                  55                  60

Trp Ile Ile Thr Cys Val Leu Cys Cys Ser Lys His Ala Arg Cys
65                  70                  75                  80

Phe Ile Leu Leu Val Phe Leu Ser Cys Gly Leu Arg Glu Gly Arg Asn
                85                  90                  95

Ala Leu Ile Ala Ala Gly Thr Gly Ile Val Ile Leu Gly His Val Glu
            100                 105                 110

Asn Ile Phe His Asn Phe Lys Gly Leu Leu Asp Gly Met Thr Cys Asn
        115                 120                 125

Leu Arg Ala Lys Ser Phe Ser Ile His Phe Pro Leu Leu Lys Lys Tyr
    130                 135                 140

Ile Glu Ala Ile Gln Trp Ile Tyr Gly Leu Ala Thr Pro Leu Ser Val
145                 150                 155                 160

Phe Asp Asp Leu Val Ser Trp Asn Gln Thr Leu Ala Val Ser Leu Phe
                165                 170                 175

Ser Pro Ser His Val Leu Glu Ala Gln Leu Asn Asp Ser Lys Gly Glu
            180                 185                 190

Val Leu Ser Val Leu Tyr Gln Met Ala Thr Thr Glu Val Leu Ser
        195                 200                 205

Ser Leu Gly Gln Lys Leu Leu Ala Phe Ala Gly Leu Ser Leu Val Leu
    210                 215                 220

Leu Gly Thr Gly Leu Phe Met Lys Arg Phe Leu Gly Pro Cys Gly Trp
225                 230                 235                 240

Lys Tyr Glu Asn Ile Tyr Ile Thr Arg Gln Phe Val Gln Phe Asp Glu
                245                 250                 255

Arg Glu Arg His Gln Gln Arg Pro Cys Val Leu Pro Leu Asn Lys Glu
            260                 265                 270

Glu Arg Arg Lys Tyr Val Ile Pro Thr Phe Trp Pro Thr Pro Lys
        275                 280                 285

Glu Arg Lys Asn Leu Gly Leu Phe Phe Leu Pro Ile Leu Ile His Leu
    290                 295                 300

Cys Ile Trp Val Leu Phe Ala Ala Val Asp Tyr Leu Leu Tyr Arg Leu
305                 310                 315                 320

Ile Phe Ser Val Ser Lys Gln Phe Gln Ser Leu Pro Gly Phe Glu Val
                325                 330                 335

His Leu Lys Leu His Gly Glu Lys Gln Gly Thr Gln Asp Ile Ile His
            340                 345                 350

Asp Ser Ser Phe Asn Ile Ser Val Phe Glu Pro Asn Cys Ile Pro Lys
        355                 360                 365

Pro Lys Phe Leu Leu Ser Glu Thr Trp Val Pro Leu Ser Val Ile Leu
    370                 375                 380

Leu Ile Leu Val Met Leu Gly Leu Leu Ser Ser Ile Leu Met Gln Leu
385                 390                 395                 400

Lys Ile Leu Val Ser Ala Ser Phe Tyr Pro Ser Val Glu Arg Lys Arg
```

```
                      405                 410                 415
Ile Gln Tyr Leu His Ala Lys Leu Leu Lys Lys Arg Ser Lys Gln Pro
                420                 425                 430

Leu Gly Glu Val Lys Arg Arg Leu Ser Leu Tyr Leu Thr Lys Ile His
            435                 440                 445

Phe Trp Leu Pro Val Leu Lys Met Ile Arg Lys Lys Gln Met Asp Met
450                 455                 460

Ala Ser Ala Asp Lys Ser
465                 470

<210> SEQ ID NO 3
<211> LENGTH: 1993
<212> TYPE: DNA
<213> ORGANISM: Mus musculus
<220> FEATURE:
<221> NAME/KEY: CDS
<222> LOCATION: (50)..(1462)

<400> SEQUENCE: 3
gtgctttgtg cttgtggagg aacctaagcg gaacttagac acagggaga atg agg ctc     58
                                                     Met Arg Leu
                                                     1 tgg acc ttg ggc acc agt att ttc ctg agg ctt tgg gga act tat gtg    106
Trp Thr Leu Gly Thr Ser Ile Phe Leu Arg Leu Trp Gly Thr Tyr Val
    5                  10                  15 ttt cca cga agc cct agc tgg ctg gac ttc atc cag cat ttg gga gtc    154
Phe Pro Arg Ser Pro Ser Trp Leu Asp Phe Ile Gln His Leu Gly Val
20                  25                  30                  35 tgt tgc ttt gtg gcc ttc ctt tcg gtg agc ctc ttc tct gca gcc ttt    202
Cys Cys Phe Val Ala Phe Leu Ser Val Ser Leu Phe Ser Ala Ala Phe
                40                  45                  50 tac tgg atc ctg cca ccc gtt gcc ctg ctc tct tct gtc tgg atg atc    250
Tyr Trp Ile Leu Pro Pro Val Ala Leu Leu Ser Ser Val Trp Met Ile
            55                  60                  65 acc tgt gtt ttc cta tgc tgt tcc aag cgc gca cga tgc ttc att ctt    298
Thr Cys Val Phe Leu Cys Cys Ser Lys Arg Ala Arg Cys Phe Ile Leu
        70                  75                  80 ctg gcc gtt ctg tcg tgt ggc ctc cgt gaa ggt agg aac gct ttg att    346
Leu Ala Val Leu Ser Cys Gly Leu Arg Glu Gly Arg Asn Ala Leu Ile
    85                  90                  95 gcg gct ggc act ggg gta gtg atc ttt gga cat gtg gaa aat att ttt    394
Ala Ala Gly Thr Gly Val Val Ile Phe Gly His Val Glu Asn Ile Phe
100                 105                 110                 115 tat aac ttc aga ggt ctc cta gac agc atg act tgc aac cta agg gca    442
Tyr Asn Phe Arg Gly Leu Leu Asp Ser Met Thr Cys Asn Leu Arg Ala
                120                 125                 130 aag agc ttt tca gta cat ttc cca ctt tta aaa cgg tat act gaa gcc    490
Lys Ser Phe Ser Val His Phe Pro Leu Leu Lys Arg Tyr Thr Glu Ala
            135                 140                 145 atc cag tgg att tac ggc ctt gcc act ccg ctg aat cta ttt gat gac    538
Ile Gln Trp Ile Tyr Gly Leu Ala Thr Pro Leu Asn Leu Phe Asp Asp
        150                 155                 160 ctt gtt tct tgg aac cag act ctg gtg gtc tct ctt ttt agt ccc agc    586
Leu Val Ser Trp Asn Gln Thr Leu Val Val Ser Leu Phe Ser Pro Ser
    165                 170                 175 cat gcc ctg gag gct cat atg aat gac act aga gga gaa gtc ctg gga    634
His Ala Leu Glu Ala His Met Asn Asp Thr Arg Gly Glu Val Leu Gly
180                 185                 190                 195 gtc ctg cac cat atg gtg gtc acg aca gag ctg ttg act tcc gtg ggc    682
Val Leu His His Met Val Val Thr Thr Glu Leu Leu Thr Ser Val Gly
```

|  |  | 200 |  |  |  | 205 |  |  |  | 210 |  |  |  |  |
|---|---|---|---|---|---|---|---|---|---|---|---|---|---|---|

```
cag aag ttg ctt gcc ctt gcc ggg ctt ctg ctc atc cta gtc agc act      730
Gln Lys Leu Leu Ala Leu Ala Gly Leu Leu Leu Ile Leu Val Ser Thr
            215                 220                 225 ggc ctc ttc ctg aag cga ttc ctg ggc cct tgt ggc tgg aag tat gag      778
Gly Leu Phe Leu Lys Arg Phe Leu Gly Pro Cys Gly Trp Lys Tyr Glu
            230                 235                 240 aat gtc tac atc acc aaa caa ttt gtt cgg ttt gat gaa aag gag agg      826
Asn Val Tyr Ile Thr Lys Gln Phe Val Arg Phe Asp Glu Lys Glu Arg
            245                 250                 255 cac caa cag cgg ccc tgt gtc ctc ccg ctg aat aag aag gaa agg aag      874
His Gln Gln Arg Pro Cys Val Leu Pro Leu Asn Lys Lys Glu Arg Lys
260                 265                 270                 275 aaa tat gtc atc gtc cca tct ttg cag ctg act cct aag gag aag aaa      922
Lys Tyr Val Ile Val Pro Ser Leu Gln Leu Thr Pro Lys Glu Lys Lys
                280                 285                 290 acc ctt ggg ctg ttc ttc ctt cct gtc ctg acc tat ctc tac atg tgg      970
Thr Leu Gly Leu Phe Phe Leu Pro Val Leu Thr Tyr Leu Tyr Met Trp
            295                 300                 305 gtg ctg ttt gcc gct gtg gac tat ctg ctg tat cgg ctc atc tcc tcc     1018
Val Leu Phe Ala Ala Val Asp Tyr Leu Leu Tyr Arg Leu Ile Ser Ser
            310                 315                 320 atg aac aaa cag ttc caa agc ttg cca ggg ctg gaa gtt cac ttg aaa     1066
Met Asn Lys Gln Phe Gln Ser Leu Pro Gly Leu Glu Val His Leu Lys
325                 330                 335 cta cgt gga gag aag caa gga acc caa gga gtc gtc cat gat tct gcc     1114
Leu Arg Gly Glu Lys Gln Gly Thr Gln Gly Val Val His Asp Ser Ala
340                 345                 350                 355 ttt aat ata tct atg ttt gaa ccg agc tgc att cct aaa cca cgt ctc     1162
Phe Asn Ile Ser Met Phe Glu Pro Ser Cys Ile Pro Lys Pro Arg Leu
                360                 365                 370 agt gtg tct gag act tgg gtt cct ctc agt att att ctg tta aca cta     1210
Ser Val Ser Glu Thr Trp Val Pro Leu Ser Ile Ile Leu Leu Thr Leu
            375                 380                 385 ata ata cta gga ttg ttg tct tct atg ctg atg cag ctt aaa att ctc     1258
Ile Ile Leu Gly Leu Leu Ser Ser Met Leu Met Gln Leu Lys Ile Leu
            390                 395                 400 gtg tca gtc tcc ttc tac ccc aaa gtg gag agg gag aga att gaa tac     1306
Val Ser Val Ser Phe Tyr Pro Lys Val Glu Arg Glu Arg Ile Glu Tyr
            405                 410                 415 ctg cat gcg aag ctc ctt gag aaa cga tca aag cag cca ttg aga gag     1354
Leu His Ala Lys Leu Leu Glu Lys Arg Ser Lys Gln Pro Leu Arg Glu
420                 425                 430                 435 gct gac ggg aaa ccg agc ctg tac ttt aaa aag att cat ttc tgg ttt     1402
Ala Asp Gly Lys Pro Ser Leu Tyr Phe Lys Lys Ile His Phe Trp Phe
                440                 445                 450 cca gtc ctg aaa atg att agg aag aag cag aca atc cct gca aat gaa     1450
Pro Val Leu Lys Met Ile Arg Lys Lys Gln Thr Ile Pro Ala Asn Glu
            455                 460                 465 gat gat cta tga gcaacacagt ccctctttct gggccaactg ctgcttctgt         1502
Asp Asp Leu
        470 ctactcaaca agagggggct atctgagaag gtctacagat gtttgagttt gcaaggctgc   1562 cttctctttt ggtgatcctt caagatacat gtcgatcata atgccaaata gcccctaggt   1622 aaatagtttc agagtctgtc ttccaaacaa aacacagtat ctaaactgtg tcatagttaa   1682 agctatggtg atggctggca tggaaatgtc ctccaaaggc ttagatattt gaaaacttgg   1742 tccccagtta gtgcatcttg ggggaggctt ataaggtgtc atgttgctgg acaaagtgtg   1802
```

-continued

```
actccagagg agtgttttgc agttttaaaa gtcatgtgct actcctgttc actctactca    1862
gcctgtggct ggagatgtgg gctctcagct gtccctgcct ccatgtctgt ctgtaataga    1922
gttcccaact gtgatattga tggagtctta cctctctgaa accttaagcc caaataaatc    1982
cttccttcta t                                                         1993

<210> SEQ ID NO 4
<211> LENGTH: 470
<212> TYPE: PRT
<213> ORGANISM: Mus musculus

<400> SEQUENCE: 4

Met Arg Leu Trp Thr Leu Gly Thr Ser Ile Phe Leu Arg Leu Trp Gly
1               5                   10                  15

Thr Tyr Val Phe Pro Arg Ser Pro Ser Trp Leu Asp Phe Ile Gln His
                20                  25                  30

Leu Gly Val Cys Cys Phe Val Ala Phe Leu Ser Val Ser Leu Phe Ser
            35                  40                  45

Ala Ala Phe Tyr Trp Ile Leu Pro Pro Val Ala Leu Leu Ser Ser Val
        50                  55                  60

Trp Met Ile Thr Cys Val Phe Leu Cys Cys Ser Lys Arg Ala Arg Cys
65                  70                  75                  80

Phe Ile Leu Leu Ala Val Leu Ser Cys Gly Leu Arg Glu Gly Arg Asn
                85                  90                  95

Ala Leu Ile Ala Ala Gly Thr Gly Val Val Ile Phe Gly His Val Glu
            100                 105                 110

Asn Ile Phe Tyr Asn Phe Arg Gly Leu Leu Asp Ser Met Thr Cys Asn
        115                 120                 125

Leu Arg Ala Lys Ser Phe Ser Val His Phe Pro Leu Lys Arg Tyr
130                 135                 140

Thr Glu Ala Ile Gln Trp Ile Tyr Gly Leu Ala Thr Pro Leu Asn Leu
145                 150                 155                 160

Phe Asp Asp Leu Val Ser Trp Asn Gln Thr Leu Val Val Ser Leu Phe
                165                 170                 175

Ser Pro Ser His Ala Leu Glu Ala His Met Asn Asp Thr Arg Gly Glu
            180                 185                 190

Val Leu Gly Val Leu His His Met Val Val Thr Thr Glu Leu Leu Thr
        195                 200                 205

Ser Val Gly Gln Lys Leu Leu Ala Leu Ala Gly Leu Leu Ile Leu
210                 215                 220

Val Ser Thr Gly Leu Phe Leu Lys Arg Phe Leu Gly Pro Cys Gly Trp
225                 230                 235                 240

Lys Tyr Glu Asn Val Tyr Ile Thr Lys Gln Phe Val Arg Phe Asp Glu
                245                 250                 255

Lys Glu Arg His Gln Gln Arg Pro Cys Val Leu Pro Leu Asn Lys Lys
            260                 265                 270

Glu Arg Lys Lys Tyr Val Ile Val Pro Ser Leu Gln Leu Thr Pro Lys
        275                 280                 285

Glu Lys Lys Thr Leu Gly Leu Phe Phe Leu Pro Val Leu Thr Tyr Leu
    290                 295                 300

Tyr Met Trp Val Leu Phe Ala Ala Val Asp Tyr Leu Leu Tyr Arg Leu
305                 310                 315                 320

Ile Ser Ser Met Asn Lys Gln Phe Gln Ser Leu Pro Gly Leu Glu Val
                325                 330                 335
```

```
His Leu Lys Leu Arg Gly Glu Lys Gln Gly Thr Gln Gly Val Val His
            340                 345                 350

Asp Ser Ala Phe Asn Ile Ser Met Phe Glu Pro Ser Cys Ile Pro Lys
            355                 360                 365

Pro Arg Leu Ser Val Ser Glu Thr Trp Val Pro Leu Ser Ile Ile Leu
        370                 375                 380

Leu Thr Leu Ile Ile Leu Gly Leu Leu Ser Ser Met Leu Met Gln Leu
385                 390                 395                 400

Lys Ile Leu Val Ser Val Ser Phe Tyr Pro Lys Val Glu Arg Glu Arg
                405                 410                 415

Ile Glu Tyr Leu His Ala Lys Leu Leu Glu Lys Arg Ser Lys Gln Pro
            420                 425                 430

Leu Arg Glu Ala Asp Gly Lys Pro Ser Leu Tyr Phe Lys Lys Ile His
        435                 440                 445

Phe Trp Phe Pro Val Leu Lys Met Ile Arg Lys Lys Gln Thr Ile Pro
    450                 455                 460

Ala Asn Glu Asp Asp Leu
465             470

<210> SEQ ID NO 5
<211> LENGTH: 1825
<212> TYPE: DNA
<213> ORGANISM: Mus musculus
<220> FEATURE:
<221> NAME/KEY: CDS
<222> LOCATION: (50)..(1294)

<400> SEQUENCE: 5
gtgctttgtg cttgtggagg aacctaagcg gaacttagac acagggaga atg agg ctc      58
                                                     Met Arg Leu
                                                       1 tgg acc ttg ggc acc agt att ttc ctg agg ctt tgg ggg act tat gtg       106
Trp Thr Leu Gly Thr Ser Ile Phe Leu Arg Leu Trp Gly Thr Tyr Val
    5                  10                  15 ttt cca cga agc cct agc tgg ctg gac ttc atc cag cat ttg gga gtc       154
Phe Pro Arg Ser Pro Ser Trp Leu Asp Phe Ile Gln His Leu Gly Val
 20                  25                  30                  35 tgt tgc ttt gtg gcc ttc ctt tcg gtg agc ctc ttc tct gca gcc ttt       202
Cys Cys Phe Val Ala Phe Leu Ser Val Ser Leu Phe Ser Ala Ala Phe
             40                  45                  50 tac tgg atc ctg cca ccc gtt gcc ctg ctc tct tct gtc tgg atg atc       250
Tyr Trp Ile Leu Pro Pro Val Ala Leu Leu Ser Ser Val Trp Met Ile
         55                  60                  65 acc tgt gtt ttc cta tgc tgt tcc aag cgc gca cga tgc ttc att ctt       298
Thr Cys Val Phe Leu Cys Cys Ser Lys Arg Ala Arg Cys Phe Ile Leu
     70                  75                  80 ctg gcc gtt ctg tcg tgt ggc ctc cgt gaa ggt agg aac gct ttg att       346
Leu Ala Val Leu Ser Cys Gly Leu Arg Glu Gly Arg Asn Ala Leu Ile
 85                  90                  95 gcg gct ggc act ggg gta gtg atc ttt gga cat gtg gaa aat att ttt       394
Ala Ala Gly Thr Gly Val Val Ile Phe Gly His Val Glu Asn Ile Phe
100                 105                 110                 115 tat aac ttc aga ggt ctc cta gac agc atg act tgc aac cta agg gca       442
Tyr Asn Phe Arg Gly Leu Leu Asp Ser Met Thr Cys Asn Leu Arg Ala
                120                 125                 130 aag agc ttt tca gta cat ttc cca ctt tta aaa cgg tat act gaa gcc       490
Lys Ser Phe Ser Val His Phe Pro Leu Leu Lys Arg Tyr Thr Glu Ala
            135                 140                 145
```

| | | |
|---|---|---|
| atc cag tgg att tac ggc ctt gcc act ccg ctg aat cta ttt gat gac<br>Ile Gln Trp Ile Tyr Gly Leu Ala Thr Pro Leu Asn Leu Phe Asp Asp<br>150                            155                        160 | | 538 |
| ctt gtt tct tgg aac cag act ctg gtg gtc tct ctt ttt agt ccc agc<br>Leu Val Ser Trp Asn Gln Thr Leu Val Val Ser Leu Phe Ser Pro Ser<br>165                            170                       175 | | 586 |
| cat gcc ctg gag gct cat atg aat gac act aga gga gaa gtc ctg gga<br>His Ala Leu Glu Ala His Met Asn Asp Thr Arg Gly Glu Val Leu Gly<br>180                            185                       190                195 | | 634 |
| gtc ctg cac cat atg gtg gtc acg aca gag ctg ttg act tcc gtg ggc<br>Val Leu His His Met Val Val Thr Thr Glu Leu Leu Thr Ser Val Gly<br>                    200                       205                       210 | | 682 |
| cag aag ttg ctt gcc ctt gcc ggg ctt ctg ctc atc cta gtc agc act<br>Gln Lys Leu Leu Ala Leu Ala Gly Leu Leu Leu Ile Leu Val Ser Thr<br>               215                       220                       225 | | 730 |
| ggc ctc ttc ctg aag cga ttc ctg ggc cct tgt ggc tgg aag tat gag<br>Gly Leu Phe Leu Lys Arg Phe Leu Gly Pro Cys Gly Trp Lys Tyr Glu<br>       230                       235                       240 | | 778 |
| aat gtc tac atc acc aaa caa ttt gtt cgg ttt gat gaa aag gag agg<br>Asn Val Tyr Ile Thr Lys Gln Phe Val Arg Phe Asp Glu Lys Glu Arg<br>245                            250                       255 | | 826 |
| cac caa cag cgg ccc tgt gtc ctc ccg ctg aat aag aag gaa agg aag<br>His Gln Gln Arg Pro Cys Val Leu Pro Leu Asn Lys Lys Glu Arg Lys<br>260                            265                       270                275 | | 874 |
| aaa tat gtc atc gtc cca tct ttg cag ctg act cct aag gag aag aaa<br>Lys Tyr Val Ile Val Pro Ser Leu Gln Leu Thr Pro Lys Glu Lys Lys<br>                    280                       285                       290 | | 922 |
| acc ctt ggg ctg ttc ttc ctt cct gtc ctg acc tat ctc tac atg tgg<br>Thr Leu Gly Leu Phe Phe Leu Pro Val Leu Thr Tyr Leu Tyr Met Trp<br>               295                       300                       305 | | 970 |
| gtg ctg ttt gcc gct gtg gac tat ctg ctg tat cgg ctc atc tcc tcc<br>Val Leu Phe Ala Ala Val Asp Tyr Leu Leu Tyr Arg Leu Ile Ser Ser<br>       310                       315                       320 | | 1018 |
| atg aac aaa cag ttc caa agc ttg cca ggg ctg gaa gtt cac ttg aaa<br>Met Asn Lys Gln Phe Gln Ser Leu Pro Gly Leu Glu Val His Leu Lys<br>325                            330                       335 | | 1066 |
| cta cgt gga gag ctt aaa att ctc gtg tca gtc tcc ttc tac ccc aaa<br>Leu Arg Gly Glu Leu Lys Ile Leu Val Ser Val Ser Phe Tyr Pro Lys<br>340                            345                       350                355 | | 1114 |
| gtg gag agg gag aga att gaa tac ctg cat gcg aag ctc ctt gag aaa<br>Val Glu Arg Glu Arg Ile Glu Tyr Leu His Ala Lys Leu Leu Glu Lys<br>                    360                       365                       370 | | 1162 |
| cga tca aag cag cca ttg aga gag gct gac ggg aaa ccg agc ctg tac<br>Arg Ser Lys Gln Pro Leu Arg Glu Ala Asp Gly Lys Pro Ser Leu Tyr<br>       375                       380                       385 | | 1210 |
| ttt aaa aag att cat ttc tgg ttt cca gtc ctg aaa atg att agg aag<br>Phe Lys Lys Ile His Phe Trp Phe Pro Val Leu Lys Met Ile Arg Lys<br>390                            395                       400 | | 1258 |
| aag cag aca atc cct gca aat gaa gat gat cta tga gcaacacagt<br>Lys Gln Thr Ile Pro Ala Asn Glu Asp Asp Leu<br>       405                       410 | | 1304 |
| ccctctttct gggccaactg ctgcttctgt ctactcaaca agaggggct atctgagaag | | 1364 |
| gtctacagat gtttgagttt gcaaggctgc ctttctcttt ggtgatcctt caagatacat | | 1424 |
| gtcgatcata atgccaaata gcccctaggt aaatagtttc agagtctgtc ttccaaacaa | | 1484 |
| aacacagtat ctaaactgtg tcatagttaa agctatggtg atggctggca tggaaatgtc | | 1544 |
| ctccaaaggc ttagatattt gaaaacttgg tccccagtta gtgcatcttg ggggaggctt | | 1604 |
| ataaggtgtc atgttgctgg acaaagtgtg actccagagg agtgttttgc agttttaaaa | | 1664 |

```
gtcatgtgct actcctgttc actctactca gcctgtggct ggagatgtgg gctctcagct    1724
gtccctgcct ccatgtctgt ctgtaataga gttcccaact gtgatattga tggagtctta    1784
cctctctgaa accttaagcc caaataaatc cttccttcta t                        1825
```

<210> SEQ ID NO 6
<211> LENGTH: 414
<212> TYPE: PRT
<213> ORGANISM: Mus musculus

<400> SEQUENCE: 6

Met Arg Leu Trp Thr Leu Gly Thr Ser Ile Phe Leu Arg Leu Trp Gly
1               5                   10                  15

Thr Tyr Val Phe Pro Arg Ser Pro Ser Trp Leu Asp Phe Ile Gln His
            20                  25                  30

Leu Gly Val Cys Cys Phe Val Ala Phe Leu Ser Val Ser Leu Phe Ser
        35                  40                  45

Ala Ala Phe Tyr Trp Ile Leu Pro Pro Val Ala Leu Leu Ser Ser Val
    50                  55                  60

Trp Met Ile Thr Cys Val Phe Leu Cys Cys Ser Lys Arg Ala Arg Cys
65                  70                  75                  80

Phe Ile Leu Leu Ala Val Leu Ser Cys Gly Leu Arg Glu Gly Arg Asn
                85                  90                  95

Ala Leu Ile Ala Ala Gly Thr Gly Val Val Ile Phe Gly His Val Glu
            100                 105                 110

Asn Ile Phe Tyr Asn Phe Arg Gly Leu Leu Asp Ser Met Thr Cys Asn
        115                 120                 125

Leu Arg Ala Lys Ser Phe Ser Val His Phe Pro Leu Leu Lys Arg Tyr
    130                 135                 140

Thr Glu Ala Ile Gln Trp Ile Tyr Gly Leu Ala Thr Pro Leu Asn Leu
145                 150                 155                 160

Phe Asp Asp Leu Val Ser Trp Asn Gln Thr Leu Val Val Ser Leu Phe
                165                 170                 175

Ser Pro Ser His Ala Leu Glu Ala His Met Asn Asp Thr Arg Gly Glu
            180                 185                 190

Val Leu Gly Val Leu His His Met Val Val Thr Thr Glu Leu Leu Thr
        195                 200                 205

Ser Val Gly Gln Lys Leu Leu Ala Leu Ala Gly Leu Leu Ile Leu
    210                 215                 220

Val Ser Thr Gly Leu Phe Leu Lys Arg Phe Leu Gly Pro Cys Gly Trp
225                 230                 235                 240

Lys Tyr Glu Asn Val Tyr Ile Thr Lys Gln Phe Val Arg Phe Asp Glu
                245                 250                 255

Lys Glu Arg His Gln Gln Arg Pro Cys Val Leu Pro Leu Asn Lys Lys
            260                 265                 270

Glu Arg Lys Lys Tyr Val Ile Val Pro Ser Leu Gln Leu Thr Pro Lys
        275                 280                 285

Glu Lys Lys Thr Leu Gly Leu Phe Phe Leu Pro Val Leu Thr Tyr Leu
    290                 295                 300

Tyr Met Trp Val Leu Phe Ala Ala Val Asp Tyr Leu Leu Tyr Arg Leu
305                 310                 315                 320

Ile Ser Ser Met Asn Lys Gln Phe Gln Ser Leu Pro Gly Leu Glu Val
                325                 330                 335

His Leu Lys Leu Arg Gly Glu Leu Lys Ile Leu Val Ser Val Ser Phe

```
                340             345             350
Tyr Pro Lys Val Glu Arg Glu Arg Ile Glu Tyr Leu His Ala Lys Leu
            355             360             365

Leu Glu Lys Arg Ser Lys Gln Pro Leu Arg Glu Ala Asp Gly Lys Pro
            370             375             380

Ser Leu Tyr Phe Lys Lys Ile His Phe Trp Phe Pro Val Leu Lys Met
385             390             395             400

Ile Arg Lys Lys Gln Thr Ile Pro Ala Asn Glu Asp Leu
            405             410

<210> SEQ ID NO 7
<211> LENGTH: 20
<212> TYPE: DNA
<213> ORGANISM: Mus musculus

<400> SEQUENCE: 7
aaaacccttg ggctgttctt                                               20

<210> SEQ ID NO 8
<211> LENGTH: 20
<212> TYPE: DNA
<213> ORGANISM: Mus musculus

<400> SEQUENCE: 8
cttcgcatgc aggtattcaa                                               20

<210> SEQ ID NO 9
<211> LENGTH: 20
<212> TYPE: DNA
<213> ORGANISM: Mus musculus

<400> SEQUENCE: 9
gagggccaac tcaagaagaa                                               20

<210> SEQ ID NO 10
<211> LENGTH: 20
<212> TYPE: DNA
<213> ORGANISM: Mus musculus

<400> SEQUENCE: 10
gccgtggcgt tatacataca                                               20

<210> SEQ ID NO 11
<211> LENGTH: 19
<212> TYPE: DNA
<213> ORGANISM: Mus musculus

<400> SEQUENCE: 11
cagctgtcct ggctcaaaa                                                19

<210> SEQ ID NO 12
<211> LENGTH: 20
<212> TYPE: DNA
<213> ORGANISM: Mus musculus

<400> SEQUENCE: 12
acatagccca caccgttctc                                               20

<210> SEQ ID NO 13
<211> LENGTH: 20
<212> TYPE: DNA
<213> ORGANISM: Mus musculus
```

```
<400> SEQUENCE: 13
aaacccatca ccatcttcca                                              20

<210> SEQ ID NO 14
<211> LENGTH: 20
<212> TYPE: DNA
<213> ORGANISM: Mus musculus

<400> SEQUENCE: 14
gtggttcaca cccatcacaa                                              20

<210> SEQ ID NO 15
<211> LENGTH: 15
<212> TYPE: PRT
<213> ORGANISM: Artificial Sequence
<220> FEATURE:
<223> OTHER INFORMATION: Synthetic partial peptide of mouse DC-STAMP

<400> SEQUENCE: 15

Cys Ser Leu Pro Gly Leu Glu Val His Leu Lys Leu Arg Gly Glu
1               5                   10                  15

<210> SEQ ID NO 16
<211> LENGTH: 29
<212> TYPE: DNA
<213> ORGANISM: Artificial Sequence
<220> FEATURE:
<223> OTHER INFORMATION: DNA template 1 for mouse DC-STAMP

<400> SEQUENCE: 16
aatactagga ttgttgtctt ccctgtctc                                    29

<210> SEQ ID NO 17
<211> LENGTH: 29
<212> TYPE: DNA
<213> ORGANISM: Artificial Sequence
<220> FEATURE:
<223> OTHER INFORMATION: DNA template 2 for mouse DC-STAMP

<400> SEQUENCE: 17
aagaagacaa caatcctagt acctgtctc                                    29

<210> SEQ ID NO 18
<211> LENGTH: 29
<212> TYPE: DNA
<213> ORGANISM: Artificial Sequence
<220> FEATURE:
<223> OTHER INFORMATION: DNA template 3 for mouse DC-STAMP

<400> SEQUENCE: 18
aatactagga gcgttgtctt ccctgtctc                                    29

<210> SEQ ID NO 19
<211> LENGTH: 29
<212> TYPE: DNA
<213> ORGANISM: Artificial Sequence
<220> FEATURE:
<223> OTHER INFORMATION: DNA template 4 for mouse DC-STAMP

<400> SEQUENCE: 19
aagaagacaa cgctcctagt acctgtctc                                    29

<210> SEQ ID NO 20
<211> LENGTH: 29
```

```
<212> TYPE: DNA
<213> ORGANISM: Artificial Sequence
<220> FEATURE:
<223> OTHER INFORMATION: DNA template 5 for mouse DC-STAMP

<400> SEQUENCE: 20
aattctcgtg tcagtctcct tcctgtctc                                              29

<210> SEQ ID NO 21
<211> LENGTH: 29
<212> TYPE: DNA
<213> ORGANISM: Artificial Sequence
<220> FEATURE:
<223> OTHER INFORMATION: DNA template 6 for mouse DC-STAMP

<400> SEQUENCE: 21
aaaaggagac tgacacgaga acctgtctc                                              29

<210> SEQ ID NO 22
<211> LENGTH: 29
<212> TYPE: DNA
<213> ORGANISM: Artificial Sequence
<220> FEATURE:
<223> OTHER INFORMATION: DNA template 7 for mouse DC-STAMP

<400> SEQUENCE: 22
aattctcgta ccagtctcct tcctgtctc                                              29

<210> SEQ ID NO 23
<211> LENGTH: 29
<212> TYPE: DNA
<213> ORGANISM: Artificial Sequence
<220> FEATURE:
<223> OTHER INFORMATION: DNA template 8 for mouse DC-STAMP

<400> SEQUENCE: 23
aaaaggagac tggtacgaga acctgtctc                                              29

<210> SEQ ID NO 24
<211> LENGTH: 41
<212> TYPE: DNA
<213> ORGANISM: Artificial Sequence
<220> FEATURE:
<223> OTHER INFORMATION: PCR forward primer for mouse DC-STAMP

<400> SEQUENCE: 24
tttgtcgaca tgaggctctg gaccttgggc accagtattt t                                41

<210> SEQ ID NO 25
<211> LENGTH: 41
<212> TYPE: DNA
<213> ORGANISM: Artificial Sequence
<220> FEATURE:
<223> OTHER INFORMATION: PCR reverse primer for mouse DC-STAMP

<400> SEQUENCE: 25
tttgcggccg ctcatagatc atcttcattt gcagggattg t                                41

<210> SEQ ID NO 26
<211> LENGTH: 1413
<212> TYPE: DNA
<213> ORGANISM: Mus musculus
<220> FEATURE:
<221> NAME/KEY: CDS
<222> LOCATION: (1)..(1410)

<400> SEQUENCE: 26
```

-continued

| | |
|---|---|
| atg agg ctc tgg acc ttg ggc acc agt att ttc ctg agg ctt tgg ggg<br>Met Arg Leu Trp Thr Leu Gly Thr Ser Ile Phe Leu Arg Leu Trp Gly<br>1               5                   10                  15 | 48 |
| act tat gtg ttt cca cga agc cct agc tgg ctg gac ttc atc cag cat<br>Thr Tyr Val Phe Pro Arg Ser Pro Ser Trp Leu Asp Phe Ile Gln His<br>            20                  25                  30 | 96 |
| ttg gga gtc tgt tgc ttt gtg gcc ttc ctt tcg gtg agc ctc ttc tct<br>Leu Gly Val Cys Cys Phe Val Ala Phe Leu Ser Val Ser Leu Phe Ser<br>        35                  40                  45 | 144 |
| gca gcc ttt tac tgg atc ctg cca ccc gtt gcc ctc tct tct gtc<br>Ala Ala Phe Tyr Trp Ile Leu Pro Pro Val Ala Leu Ser Ser Val<br>50                  55                  60 | 192 |
| tgg atg atc acc tgt gtt ttc cta tgc tgt tcc aag cgc gca cga tgc<br>Trp Met Ile Thr Cys Val Phe Leu Cys Cys Ser Lys Arg Ala Arg Cys<br>65                  70                  75                  80 | 240 |
| ttc att ctt ctg gcc gtt ctg tcg tgt ggc ctc cgt gaa ggt agg aac<br>Phe Ile Leu Leu Ala Val Leu Ser Cys Gly Leu Arg Glu Gly Arg Asn<br>                85                  90                  95 | 288 |
| gct ttg att gcg gct ggc act ggg gta gtg atc ttt gga cat gtg gaa<br>Ala Leu Ile Ala Ala Gly Thr Gly Val Val Ile Phe Gly His Val Glu<br>            100                 105                 110 | 336 |
| aat att ttt tat aac ttc aga ggt ctc cta gac agc atg act tgc aac<br>Asn Ile Phe Tyr Asn Phe Arg Gly Leu Leu Asp Ser Met Thr Cys Asn<br>        115                 120                 125 | 384 |
| cta agg gca aag agc ttt tca gta cat ttc cca ctt tta aaa cgg tat<br>Leu Arg Ala Lys Ser Phe Ser Val His Phe Pro Leu Leu Lys Arg Tyr<br>130                 135                 140 | 432 |
| act gaa gcc atc cag tgg att tac ggc ctt gcc act ccg ctg aat cta<br>Thr Glu Ala Ile Gln Trp Ile Tyr Gly Leu Ala Thr Pro Leu Asn Leu<br>145                 150                 155                 160 | 480 |
| ttt gat gac ctt gtt tct tgg aac cag act ctg gtg gtc tct ctt ttt<br>Phe Asp Asp Leu Val Ser Trp Asn Gln Thr Leu Val Val Ser Leu Phe<br>                165                 170                 175 | 528 |
| agt ccc agc cat gcc ctg gag gct cat atg aat gac act aga gga gaa<br>Ser Pro Ser His Ala Leu Glu Ala His Met Asn Asp Thr Arg Gly Glu<br>            180                 185                 190 | 576 |
| gtc ctg gga gtc ctg cac cat atg gtg gtc acg aca gag ctg ttg act<br>Val Leu Gly Val Leu His His Met Val Val Thr Thr Glu Leu Leu Thr<br>        195                 200                 205 | 624 |
| tcc gtg ggc cag aag ttg ctt gcc ctt gcc ggg ctt ctg ctc atc cta<br>Ser Val Gly Gln Lys Leu Leu Ala Leu Ala Gly Leu Leu Leu Ile Leu<br>210                 215                 220 | 672 |
| gtc agc act ggc ctc ttc ctg aag cga ttc ctg ggc cct tgt ggc tgg<br>Val Ser Thr Gly Leu Phe Leu Lys Arg Phe Leu Gly Pro Cys Gly Trp<br>225                 230                 235                 240 | 720 |
| aag tat gag aat gtc tac atc acc aaa caa ttt gtt cgg ttt gat gaa<br>Lys Tyr Glu Asn Val Tyr Ile Thr Lys Gln Phe Val Arg Phe Asp Glu<br>                245                 250                 255 | 768 |
| aag gag agg cac caa cag cgg ccc tgt gtc ctc ccg ctg aat aag aag<br>Lys Glu Arg His Gln Gln Arg Pro Cys Val Leu Pro Leu Asn Lys Lys<br>            260                 265                 270 | 816 |
| gaa agg aag aaa tat gtc atc gtc cca tct ttg cag ctg act cct aag<br>Glu Arg Lys Lys Tyr Val Ile Val Pro Ser Leu Gln Leu Thr Pro Lys<br>        275                 280                 285 | 864 |
| gag aag aaa acc ctt ggg ctg ttc ttc ctt cct gtc ctg acc tat ctc<br>Glu Lys Lys Thr Leu Gly Leu Phe Phe Leu Pro Val Leu Thr Tyr Leu<br>290                 295                 300 | 912 |
| tac atg tgg gtg ctg ttt gcc gct gtg gac tat ctg ctg tat cgg ctc<br>Tyr Met Trp Val Leu Phe Ala Ala Val Asp Tyr Leu Leu Tyr Arg Leu | 960 |

| | | | | | | | | | | | | | | | | |
|---|---|---|---|---|---|---|---|---|---|---|---|---|---|---|---|---|
| | 305 | | | 310 | | | | 315 | | | | 320 | | | | |
| atc | tcc | tcc | atg | aac | aaa | cag | ttc | caa | agc | ttg | cca | ggg | ctg | gaa | gtt | 1008 |
| Ile | Ser | Ser | Met | Asn | Lys | Gln | Phe | Gln | Ser | Leu | Pro | Gly | Leu | Glu | Val | |
| | | | | 325 | | | | | 330 | | | | | 335 | | |
| cac | ttg | aaa | cta | cgt | gga | gag | aag | caa | gga | acc | caa | gga | gtc | gtc | cat | 1056 |
| His | Leu | Lys | Leu | Arg | Gly | Glu | Lys | Gln | Gly | Thr | Gln | Gly | Val | Val | His | |
| | | | 340 | | | | | 345 | | | | | 350 | | | |
| gat | tct | gcc | ttt | aat | ata | tct | atg | ttt | gaa | ccg | agc | tgc | att | cct | aaa | 1104 |
| Asp | Ser | Ala | Phe | Asn | Ile | Ser | Met | Phe | Glu | Pro | Ser | Cys | Ile | Pro | Lys | |
| | | | 355 | | | | | 360 | | | | | 365 | | | |
| cca | cgt | ctc | agt | gtg | tct | gag | act | tgg | gtt | cct | ctc | agt | att | att | ctg | 1152 |
| Pro | Arg | Leu | Ser | Val | Ser | Glu | Thr | Trp | Val | Pro | Leu | Ser | Ile | Ile | Leu | |
| | 370 | | | | | 375 | | | | | 380 | | | | | |
| tta | aca | cta | ata | ata | cta | gga | ttg | ttg | tct | tct | atg | ctg | atg | cag | ctt | 1200 |
| Leu | Thr | Leu | Ile | Ile | Leu | Gly | Leu | Leu | Ser | Ser | Met | Leu | Met | Gln | Leu | |
| 385 | | | | | 390 | | | | | 395 | | | | | 400 | |
| aaa | att | ctc | gtg | tca | gtc | tcc | ttc | tac | ccc | aaa | gtg | gag | agg | gag | aga | 1248 |
| Lys | Ile | Leu | Val | Ser | Val | Ser | Phe | Tyr | Pro | Lys | Val | Glu | Arg | Glu | Arg | |
| | | | | 405 | | | | | 410 | | | | | 415 | | |
| att | gaa | tac | ctg | cat | gcg | aag | ctc | ctt | gag | aaa | cga | tca | aag | cag | cca | 1296 |
| Ile | Glu | Tyr | Leu | His | Ala | Lys | Leu | Leu | Glu | Lys | Arg | Ser | Lys | Gln | Pro | |
| | | | 420 | | | | | 425 | | | | | 430 | | | |
| ttg | aga | gag | gct | gac | ggg | aaa | ccg | agc | ctg | tac | ttt | aaa | aag | att | cat | 1344 |
| Leu | Arg | Glu | Ala | Asp | Gly | Lys | Pro | Ser | Leu | Tyr | Phe | Lys | Lys | Ile | His | |
| | | 435 | | | | | 440 | | | | | 445 | | | | |
| ttc | tgg | ttt | cca | gtc | ctg | aaa | atg | att | agg | aag | aag | cag | aca | atc | cct | 1392 |
| Phe | Trp | Phe | Pro | Val | Leu | Lys | Met | Ile | Arg | Lys | Lys | Gln | Thr | Ile | Pro | |
| | 450 | | | | | 455 | | | | | 460 | | | | | |
| gca | aat | gaa | gat | gat | cta | tga | | | | | | | | | | 1413 |
| Ala | Asn | Glu | Asp | Asp | Leu | | | | | | | | | | | |
| 465 | | | | | 470 | | | | | | | | | | | |

<210> SEQ ID NO 27
<211> LENGTH: 470
<212> TYPE: PRT
<213> ORGANISM: Mus musculus

<400> SEQUENCE: 27

Met Arg Leu Trp Thr Leu Gly Thr Ser Ile Phe Leu Arg Leu Trp Gly
1               5                   10                  15

Thr Tyr Val Phe Pro Arg Ser Pro Ser Trp Leu Asp Phe Ile Gln His
                20                  25                  30

Leu Gly Val Cys Cys Phe Val Ala Phe Leu Ser Val Ser Leu Phe Ser
            35                  40                  45

Ala Ala Phe Tyr Trp Ile Leu Pro Pro Val Ala Leu Leu Ser Ser Val
        50                  55                  60

Trp Met Ile Thr Cys Val Phe Leu Cys Cys Ser Lys Arg Ala Arg Cys
65                  70                  75                  80

Phe Ile Leu Leu Ala Val Leu Ser Cys Gly Leu Arg Glu Gly Arg Asn
                85                  90                  95

Ala Leu Ile Ala Ala Gly Thr Val Val Ile Phe Gly His Val Glu
            100                 105                 110

Asn Ile Phe Tyr Asn Phe Arg Gly Leu Leu Asp Ser Met Thr Cys Asn
        115                 120                 125

Leu Arg Ala Lys Ser Phe Ser Val His Phe Pro Leu Leu Lys Arg Tyr
    130                 135                 140

Thr Glu Ala Ile Gln Trp Ile Tyr Gly Leu Ala Thr Pro Leu Asn Leu
145                 150                 155                 160

```
Phe Asp Asp Leu Val Ser Trp Asn Gln Thr Leu Val Val Ser Leu Phe
                165                 170                 175
Ser Pro Ser His Ala Leu Glu Ala His Met Asn Asp Thr Arg Gly Glu
                180                 185                 190
Val Leu Gly Val Leu His His Met Val Val Thr Thr Glu Leu Leu Thr
                195                 200                 205
Ser Val Gly Gln Lys Leu Leu Ala Leu Ala Gly Leu Leu Leu Ile Leu
                210                 215                 220
Val Ser Thr Gly Leu Phe Leu Lys Arg Phe Leu Gly Pro Cys Gly Trp
225                             230                 235         240
Lys Tyr Glu Asn Val Tyr Ile Thr Lys Gln Phe Val Arg Phe Asp Glu
                245                 250                 255
Lys Glu Arg His Gln Gln Arg Pro Cys Val Leu Pro Leu Asn Lys Lys
                260                 265                 270
Glu Arg Lys Lys Tyr Val Ile Val Pro Ser Leu Gln Leu Thr Pro Lys
                275                 280                 285
Glu Lys Lys Thr Leu Gly Leu Phe Phe Leu Pro Val Leu Thr Tyr Leu
                290                 295                 300
Tyr Met Trp Val Leu Phe Ala Ala Val Asp Tyr Leu Leu Tyr Arg Leu
305                             310                 315             320
Ile Ser Ser Met Asn Lys Gln Phe Gln Ser Leu Pro Gly Leu Glu Val
                325                 330                 335
His Leu Lys Leu Arg Gly Glu Lys Gln Gly Thr Gln Gly Val Val His
                340                 345                 350
Asp Ser Ala Phe Asn Ile Ser Met Phe Glu Pro Ser Cys Ile Pro Lys
                355                 360                 365
Pro Arg Leu Ser Val Ser Glu Thr Trp Val Pro Leu Ser Ile Ile Leu
370                             375                 380
Leu Thr Leu Ile Ile Leu Gly Leu Leu Ser Ser Met Leu Met Gln Leu
385                             390                 395             400
Lys Ile Leu Val Ser Val Ser Phe Tyr Pro Lys Val Glu Arg Glu Arg
                405                 410                 415
Ile Glu Tyr Leu His Ala Lys Leu Leu Glu Lys Arg Ser Lys Gln Pro
                420                 425                 430
Leu Arg Glu Ala Asp Gly Lys Pro Ser Leu Tyr Phe Lys Lys Ile His
                435                 440                 445
Phe Trp Phe Pro Val Leu Lys Met Ile Arg Lys Lys Gln Thr Ile Pro
    450                 455                 460
Ala Asn Glu Asp Asp Leu
465             470
```